(12) United States Patent
Ebens, Jr. et al.

(10) Patent No.: US 8,536,161 B2
(45) Date of Patent: *Sep. 17, 2013

(54) COMBINATIONS OF PHOSPHOINOSITIDE 3-KINASE INHIBITOR COMPOUNDS AND CHEMOTHERAPEUTIC AGENTS FOR THE TREATMENT OF HEMATOPOIETIC MALIGNANCIES

(75) Inventors: Allen J. Ebens, Jr., San Carlos, CA (US); Lori Friedman, San Carlos, CA (US)

(73) Assignee: Genentech, Inc., South San Francisco, CA (US)

(*) Notice: Subject to any disclaimer, the term of this patent is extended or adjusted under 35 U.S.C. 154(b) by 556 days.

This patent is subject to a terminal disclaimer.

(21) Appl. No.: 12/721,645

(22) Filed: Mar. 11, 2010

(65) Prior Publication Data

US 2010/0233164 A1 Sep. 16, 2010

Related U.S. Application Data

(60) Provisional application No. 61/159,622, filed on Mar. 12, 2009.

(51) Int. Cl.
*A61K 31/33* (2006.01)
*A61K 31/535* (2006.01)
*A61K 31/70* (2006.01)

(52) U.S. Cl.
USPC ............ 514/183; 514/234.2; 514/49; 514/34

(58) Field of Classification Search
USPC .................................. 514/234.2, 49, 34, 183
See application file for complete search history.

(56) References Cited

U.S. PATENT DOCUMENTS

| | | | |
|---|---|---|---|
| 7,750,002 B2 | 7/2010 | Shuttleworth et al. | |
| 7,781,433 B2 | 8/2010 | Chuckowree et al. | |
| 2002/0009444 A1* | 1/2002 | Grillo-Lopez | 424/142.1 |
| 2008/0039459 A1 | 2/2008 | Folkes et al. | |
| 2008/0076758 A1 | 3/2008 | Folkes et al. | |
| 2008/0242665 A1 | 10/2008 | Bayliss et al. | |
| 2008/0269210 A1 | 10/2008 | Castanedo et al. | |
| 2009/0098135 A1 | 4/2009 | Belvin et al. | |

OTHER PUBLICATIONS

Edgar at al., "Isoform-Specific Phosphoinositide 3-Kinase Inhibitors Exert Distinct Effects in Solid Tumors" *Cancer Research* 70(3):1164-1172 (Feb. 1, 2010).
Friedman, "GDC-0941, a potent, selective, orally bioavailable inhibitor of class I PI3K" *AACR Meeting Abstracts Online* (99th AACR Annual Meeting—Apr. 12-16, 2008; San Diego, CA, Abstract LB-110).
Hoeflich at al., "In vivo Antitumor Activity of MEK and Phosphatidylinositol 3-Kinase Inhibitors in Basal-Like Breast Cancer Models" *Clinical Cancer Research* 15(14):4649-4664 (Jul. 15, 2009).
Junttila et al., "Ligand-independent HER2/HER3/PI3K complex is disrupted by trastuzumab and is effectively inhibited by the PI3K inhibitor GDC-0941" *Cancer Cell* 15:429-440 (May 5, 2009).
Ma at al., "PI3K signaling pathway activation predicts Class I PI3K inhibitor GDC-0941 sensitivity in AML" *Blood (ASH Annual Meeting Abstracts)* (114: Abstract 1057) (2009).
O'Brien at al., "Predictive Biomarkers of Sensitivity to the Phosphatidylinositol 3 Kinase Inhibitor GDC-0941 in Breast Cancer Preclinical Models" *Clin Cancer Res.* 16(14):3670-3683 (Jul. 15, 2010).
Sos at al., "Identifying genotype-dependent efficacy of single and combined PI3K- and MAPK-pathway inhibition in cancer" *Proc. Natl. Acad. Sci. USA* 106(43):18351-18356 (Oct. 27, 2009).
Sutherlin at al., "Discovery of (Thienopyrimidin-2-yl)aminopyrimidines as Potent, Selective, and Orally Available Pan-PI3-Kinase and Dual Pan-PI3-Kinase/mTOR Inhibitors for the Treatment of Cancer" *Journal of Medicinal Chemistry* 53(3):1086-1097 (2010).
Yao at al., "Suppression of HER2/HER3-Mediated Growth of Breast Cancer Cells with Combinations of GDC-0941 PI3K Inhibitor, Trastuzumab, and Pertuzumab" *Clinical Cancer Research* 15(12):4147-4156 (Jun. 15, 2009).
Munugalavadla et al., "The PI3K inhibitor GDC-0941 Combines with Existing Clinical Regimens for Superior Activity in Multiple Myeloma" submitted to Oncogene (Oct. 15, 2012).

* cited by examiner

*Primary Examiner* — Jennifer M Kim
(74) *Attorney, Agent, or Firm* — Alex Andrus; Genentech, Inc.

(57) ABSTRACT

Combinations of PI3K inhibitor compounds having Formula I and chemotherapeutic agents, including stereoisomers, geometric isomers, tautomers, metabolites and pharmaceutically acceptable salts thereof, are useful for treating hematopoietic malignancies. Methods of using such combinations for in vitro, in situ, and in vivo diagnosis, prevention or treatment of such disorders in mammalian cells, or associated pathological conditions, are disclosed.

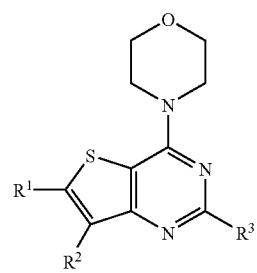

19 Claims, 19 Drawing Sheets p-Akt, clone 193H12
p-Bad, clone 185D10
p-S6RP, clone D57.2.2E
Same clones used for WB and FACS

COMBINATIONS OF PHOSPHOINOSITIDE 3-KINASE INHIBITOR COMPOUNDS AND CHEMOTHERAPEUTIC AGENTS FOR THE TREATMENT OF HEMATOPOIETIC MALIGNANCIES

CROSS REFERENCE TO RELATED APPLICATIONS

This non-provisional application filed under 37 CFR §1.53 (b), claims the benefit under 35 USC §119(e) of U.S. Provisional Application Ser. No. 61/159,622 filed on 12 Mar. 2009, which is incorporated by reference in entirety.

FIELD OF THE INVENTION

The invention relates generally to pharmaceutical combinations of compounds with activity against hematopoietic malignancies and which include compounds that inhibit PI3 kinase or mTOR activity. The invention also relates to methods of using the compounds for in vitro, in situ, and in vivo diagnosis or treatment of mammals and mammalian cells.

BACKGROUND OF THE INVENTION

Cancers which involve cells generated during hematopoiesis, a process by which cellular elements of blood, such as leukocytes, lymphocytes, natural killer cells, plasma cells, and myeloid cells such as neutrophils and monocytes are generated, are referred to as hematopoietic malignancies. Lymphocytes which can be found in blood and lymphatic tissue and are critical for immune response are categorized into two main classes of lymphocytes: B lymphocytes (B cells) and T lymphocytes (T cells), which mediate humoral and cellular immunity, respectively. B cells are lymphocytes that play a large role in the humoral immune response (as opposed to the cell-mediated immune response, which is governed by T cells). The principal functions of B cells are to make antibodies against antigens, perform the role of Antigen Presenting Cells (APCs) and eventually develop into memory B cells after activation by antigen interaction. B cells are an essential component of the adaptive immune system. B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecules of humoral immunity.

The non-Hodgkin lymphomas are a diverse group of hematopoietic malignancies which encompass any lymphoma other than Hodgkin lymphoma. Lymphoma is a type of cancer derived from lymphocytes, a type of white blood cell. Many subtypes of non-Hodgkin lymphoma have been described; these are generally grouped by their aggressiveness. Less aggressive non-Hodgkin lymphomas may be chronic diseases which exist for many years, while more aggressive non-Hodgkin lymphomas can be rapidly fatal without treatment. Non-Hodgkin lymphomas are treated by combinations of chemotherapy, monoclonal antibodies, immunotherapy, radiation, and hematopoietic stem cell transplantation.

Lymphoma is a type of neoplasm that originates in lymphocytes (a type of white blood cell in the vertebrate immune system) and in lymph nodes, presenting as an enlargement of the node (a tumor). Lymphomas are closely related to lymphoid leukemias, which also originate in lymphocytes but do not form solid tumors. There are many types of lymphomas, and in turn, lymphomas are a part of the broad group of hematopoietic malignancies called hematological neoplasms.

Acute Myeloid Leukemia (AML) comprises a heterogeneous group of malignant clonal disorders of hematopoietic stem cells committed to the myeloid linage development. There is a block in normal hematopoietic differentiation, often combined with deregulation of proliferation and apoptosis. This leads to progressive insufficiency of the normal hematopoiesis ensuing in anemia, neutropenia and thrombocytopenia. AML accounts for about 80% of all adult leukemia, and its overall incidence has been stable or slowly increasing over the past 15-20 years. The prognosis of AML remains poor, with an overall 5-year survival rate of 15-30%, while patients with AML arising out of myelodysplastic syndrome or who are aged above 60 years have an even worse prognosis with less than 10% survival at 5 years (Smith M. et al (2004) Crit. Rev. Oncol. Hematol. 50:197-222). The standard therapeutic approach for AML patients is high-dose chemotherapy, mainly consisting of cytarabine (Ara-C) and an anthracycline antibiotic such as daunorubicin or idarubicin. Usually, AML responds to initial chemotherapy, but disease relapse occurs in most patients. While results of AML treatment have improved in younger patients who can tolerate intensified treatment strategies, there have been limited changes in outcome among individuals who are above 60 years of age. The limit of acceptable toxicity for standard chemotherapeutic drugs used in AML has been reached. A significant unmet need therefore remains for new, rationally designed, minimally toxic, and effective therapies for AML (Fathi A. T. and Karp J. E. (2009) Curr. Oncol. Rep. 11:346-352; Stapnes et al (2009) Expert Opin. Investig. Drugs 18:433-455).

Combinations of anti-cancer pharmaceutical therapeutics administered simultaneously or sequentially in a dosing regimen are now common in cancer treatment. Successful combination therapy provides improved and even synergistic effect over mono-therapy, i.e. pharmaceutical treatment limited to one drug (Ouchi et al (2006) Cancer Chemother. Pharmacol. 57:693-702; Higgins et al (2004) Anti-Cancer Drugs 15:503-512). Preclinical research has been the basis for prediction of clinical stage synergy of anti-cancer pharmaceutical therapeutic combinations such as capecitabine and taxanes for the treatment of breast cancer (Sawada et al (1998) Clin. Cancer Res. 4:1013-1019). Certain doses and schedules of combination therapy can improve safety without compromising efficacy (O'Shaughnessy et al (2006) Clin. Breast Cancer April 7(1):42-50). Synergistic effects in vitro have been correlated with clinical stage synergy (Steinbach et al (2003) Clin. Inf. Dis. October 1:37 Suppl 3:S188-224).

Phosphatidylinositol 3-Kinase (PI3K) is a major signaling node for key survival and growth signals for lymphomas and is opposed by the activity of the phosphatase PTEN. The PI3K pathway is dysregulated in aggressive forms of lymphoma (Abubaker (2007) Leukemia 21:2368-2370). Eight percent of DLBCL (diffuse large B-cell lymphoma) cancers have PI3CA (phosphatidylinositol-3 kinase catalytic subunit alpha) missense mutations and 37% are PTEN negative by immunohistochemistry test.

Phosphatidylinositol is one of a number of phospholipids found in cell membranes, and which participate in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol. Chem. 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60). Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and PDK1, phosphoinositide-dependent kinase-1 (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI. A key PI3-kinase isoform in cancer is the Class I PI3-kinase, p110α as indicated by recurrent oncogenic mutations in p110α (Samuels et al (2004) Science 304:554). (U.S. Pat. No. 5,824,492; U.S. Pat. No. 5,846,824; U.S. Pat. No. 6,274,327). Other isoforms may be important in cancer and are also implicated in cardiovascular and immune-inflammatory disease (Workman P (2004) Biochem Soc Trans 32:393-396; Patel et al (2004) Proc. Am. Assoc. of Cancer Res. (Abstract LB-247) 95th Annual Meeting, March 27-31, Orlando, Fla., USA; Ahmadi K and Waterfield M D (2004) "Phosphoinositide 3-Kinase: Function and Mechanisms" Encyclopedia of Biological Chemistry (Lennarz W J, Lane M D eds) Elsevier/Academic Press), Oncogenic mutations of p110 alpha have been found at a significant frequency in colon, breast, brain, liver, ovarian, gastric, lung, and head and neck solid tumors. PTEN abnormalities are found in glioblastoma, melanoma, prostate, endometrial, ovarian, breast, lung, head and neck, hepatocellular, and thyroid cancers.

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and ω (gamma), each consisting of a distinct 110 kDa catalytic subunit and a regulatory subunit. Three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are distinct. In each of the PI3K alpha, beta, and delta subtypes, the p85 subunit acts to localize PI3 kinase to the plasma membrane by the interaction of its SH2 domain with phosphorylated tyrosine residues (present in an appropriate sequence context) in target proteins (Rameh et al (1995) Cell, 83:821-30; Volinia et al (1992) Oncogene, 7:789-93).

The PI3 kinase/Akt/PTEN pathway is an attractive target for cancer drug development since such agents would be expected to inhibit cellular proliferation, to repress signals from stromal cells that provide for survival and chemoresistance of cancer cells, to reverse the repression of apoptosis and surmount intrinsic resistance of cancer cells to cytotoxic agents. PI3 kinase inhibitors have been reported (Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070). Wortmannin analogs have PI3 kinase activity in mammals (U.S. Pat. No. 6,703,414; WO 97/15658).

Thienopyrimidine compounds of Formula I have p110 alpha binding, PI3 kinase inhibitory activity, and inhibit the growth of cancer cells (US 2008/0207611; US 2008/0039459; US 2008/0076768; US 2008/0076758; US 2008/0242665; US 2008/0269210.

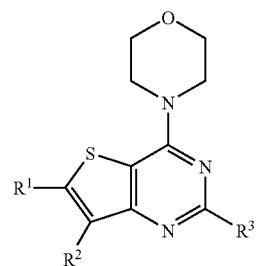

I

An exemplary Formula I compound, GDC-0941 (CAS Reg. No. 957054-30-7, Genentech Inc.), is a selective, orally bioavailable inhibitor of PI3K with promising pharmacokinetic and pharmaceutical properties (Folkes et al (2008) Jour. of Med. Chem. 51(18):5522-5532; US 2008/0076768; Belvin et al, American Association for Cancer Research Annual Meeting 2008, 99th: April 15, Abstract 4004; Folkes et al, American Association for Cancer Research Annual Meeting 2008, 99th: April 14, Abstract LB-146; Friedman et al, American Association for Cancer Research Annual Meeting 2008, 99th: April 14, Abstract LB-110). The exemplary Formula I compound, GDC-0941, shows synergistic activity in vitro and in vivo in combination with certain chemotherapeutic agents against solid tumor cell lines (U.S. Ser. No. 12/208,227, Belvin et al "Combinations Of Phosphoinositide 3-Kinase Inhibitor Compounds And Chemotherapeutic Agents, And Methods Of Use", filed 10 Sep. 2008).

SUMMARY OF THE INVENTION

The invention relates generally to thienopyrimidine compounds of Formula I with anti-cancer activity, and more specifically with PI3 kinase or mTOR inhibitory activity, administered in combination with monoclonal antibody agents or chemotherapeutic agents to inhibit the growth of hematopoietic malignancies. Certain combinations of Formula I compounds with chemotherapeutic agents show synergistic effects in inhibiting the growth of hematopoietic cancer cells in vitro and in vivo. The combinations and methods of the invention may be useful in the treatment of hematopoietic malignancies. The compositions may inhibit tumor growth in mammals and may be useful for treating human cancer patients.

In one aspect, the invention includes a method for the treatment of a hematopoietic malignancy comprising administering a therapeutic combination as a combined formulation or alternation to a mammal, wherein the therapeutic combination comprises a therapeutically effective amount of a compound having Formula I, and a therapeutically effective amount of a chemotherapeutic agent selected from dexamethasone, thioTEPA, doxorubicin, vincristine, rituximab, cyclophosphamide, prednisone, melphalan, lenalidomide, bortezomib, rapamycin, and cytarabine.

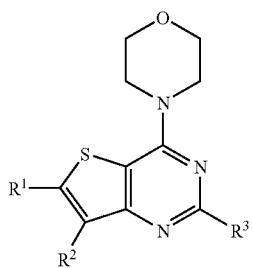

I

The invention also relates to methods of using the therapeutic combinations for in vitro, in situ, and in vivo diagnosis or treatment of mammalian cells, organisms, or associated pathological conditions related to the hematopoietic malignancies.

An aspect of the invention provides therapeutic combinations comprising 4-(2-(1H-indazol-4-yl)-6-((4-(methylsulfonyl)piperazin-1-yl)methyl)thieno[3,2-d]pyrimidin-4-yl)morpholine (US 2008/0076768; US 2008/0207611; Folkes et al (2008) Jour. of Med. Chem. 51(18):5522-5532), also known as GDC-0941 (Genentech, Inc.) and having Formula Ia and a therapeutically effective amount of a chemotherapeutic agent selected from dexamethasone, thioTEPA, doxorubicin, vincristine, rituximab, cyclophosphamide, prednisone, melphalan, lenalidomide, bortezomib, rapamycin, and cytarabine.

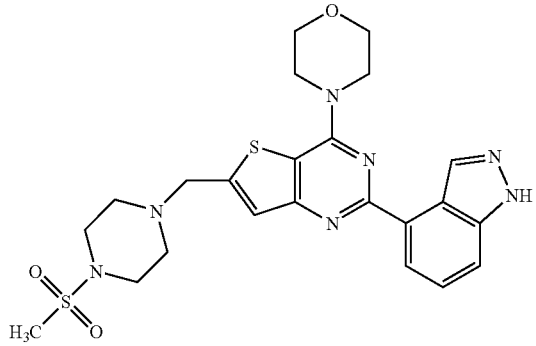

Ia

An aspect of the invention provides therapeutic combinations comprising (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (US 2008/0242665) having Formula Ib and a therapeutically effective amount of a chemotherapeutic agent selected from dexamethasone, thioTEPA, doxorubicin, vincristine, rituximab, cyclophosphamide, prednisone, melphalan, lenalidomide, bortezomib, rapamycin, and cytarabine.

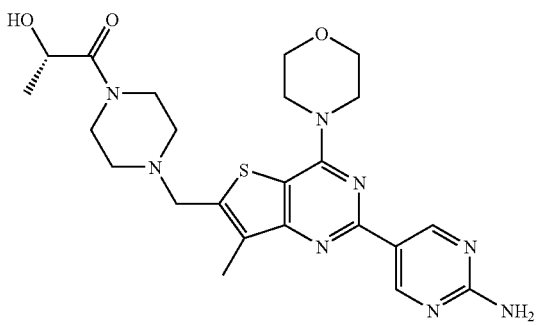

Ib

Formula I compounds include all stereoisomers, geometric isomers, tautomers, metabolites, and pharmaceutically acceptable salts thereof. Certain Formula I compounds are potent inhibitors of PI3K with drug-like physicochemical and pharmacokinetic properties. Certain Formula I compounds exhibit selectivity for class Ia PI3Ks over class Ib, in particular for the P110 alpha subtype. Formula Ia and Ib compounds are orally bioavailable and have single agent anti-tumor activity in multiple human cancer models.

Pharmaceutical compositions and therapeutic combinations of the invention comprise a chemotherapeutic agent selected from dexamethasone, thioTEPA, doxorubicin, vincristine, rituximab, cyclophosphamide, prednisone, melphalan, lenalidomide, bortezomib, rapamycin, and cytarabine.

Pharmaceutical compositions of the invention may further comprise a pharmaceutically acceptable carrier.

Another aspect of the invention provides methods of treating a hematopoietic malignancy modulated by PI3 kinases, comprising administering to a mammal in need of such treatment effective amounts of a Formula I compound and a chemotherapeutic agent. The Formula I compound and the chemotherapeutic agent may be co-formulated for administration in a combination as a pharmaceutical composition or they may be administered separately in alternation (sequentially, consecutively) as a therapeutic combination.

Another aspect of the invention provides methods of treating a hematopoietic malignancy, comprising administering to a mammal in need of such treatment effective amounts of the Formula I compound and a chemotherapeutic agent.

In a further aspect the present invention provides a method of using a pharmaceutical composition of the invention to treat a hematopoietic malignancy disease or condition modulated by PI3 kinase in a mammal.

An additional aspect of the invention is the use of a pharmaceutical composition of the invention in the preparation of a medicament for the treatment of a hematopoietic malignancy disease or condition modulated by PI3 kinase in a mammal.

Another aspect of the invention includes articles of manufacture or kits comprising a Formula I compound, a chemotherapeutic agent, a container, and optionally a package insert or label indicating a treatment for a hematopoietic malignancy.

Another aspect of the invention is a product comprising a Formula I compound, and a chemotherapeutic agent selected from dexamethasone, thioTEPA, doxorubicin, vincristine, rituximab, cyclophosphamide, prednisone, melphalan, lenalidomide, bortezomib, rapamycin, and cytarabine; as a combined preparation for separate, simultaneous or sequential use in the treatment of a hematopoietic malignancy.

Another aspect of the invention includes a method for determining compounds to be used in combination for the treatment of cancer comprising: a) administering a therapeutic combination comprising a Formula I compound, and a chemotherapeutic agent to an in vitro hematopoietic malignancy cell line with one or more mutations, and b) measuring a synergistic or non-synergistic effect.

Another aspect of the invention is methods of therapeutically treating a mammal having a hematopoietic malignancy, wherein the method comprises administering to the mammal a therapeutically effective amount of the therapeutic combination, thereby resulting in the effective therapeutic treatment of the hematopoietic malignancy, such as non-Hodgkin's lymphoma, diffuse large hematopoietic lymphoma, follicular lymphoma, mantle cell lymphoma, chronic lymphocytic leukemia, multiple myeloma, AML, and MCL. In one embodiment, the therapeutic combination inhibits one or more isoforms of PI3K. In one embodiment, the therapeutic combination inhibits mTOR.

In one aspect, the invention provides a method of inhibiting the growth of a non-Hodgkin's lymphoma comprising administering the therapeutic combination to a patient with a non-Hodgkin's lymphoma, whereby growth of the lymphoma is inhibited.

In one aspect, the invention provides a method of inhibiting the growth of a non-Hodgkin's lymphoma comprising administering the therapeutic combination to a lymphoma cell, or to a cell present in and/or adjacent to the lymphoma, whereby growth of the lymphoma is inhibited. In one embodiment, said cell is not a non-Hodgkin's lymphoma cell (e.g., it is not a T or B cell) for example, said cell may be a stromal cell.

DEFINITIONS

Figure 1A:
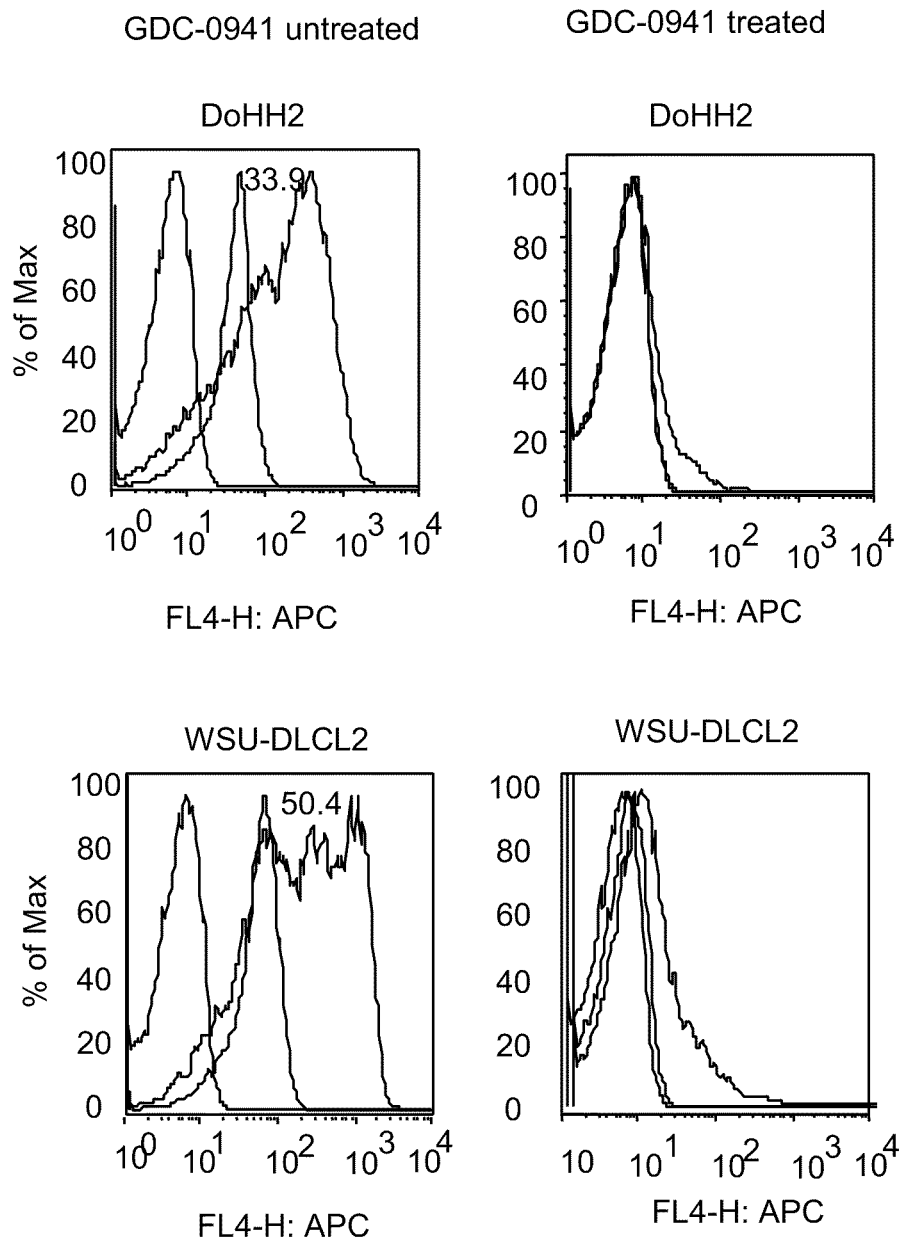
FIG. 1 shows reduction of pharmacodynamic (PD) markers measured by flow cytometry with Formula Ia (GDC-0941) treated (right column) and untreated (left column) cells, DoHH2, WSU-DLCL2, OPM2, and U266. Cells were treated in vitro with 5 µM GDC-0941 for 4 hrs.

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to both therapeutic treatment and prophylactic or preventative measures, wherein the object is to prevent or slow down (lessen) an undesired physiological change or disorder, such as the growth, development or spread of cancer. Those in need of treatment include those already with the disorder as well as those prone to have the disorder or those in whom the disorder is to be prevented. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A subject or mammal is successfully "treated" for a hematopoietic malignancy, such as non-Hodgkin's lymphoma, if after receiving a therapeutic amount of the therapeutic combination according to the methods of the invention, the patient shows one or more of: (i) observable and/or measurable reduction in the number of cancer cells or absence of the cancer cells; (ii) reduction in the tumor size; inhibition (i.e., slow to some extent and preferably stop) of cancer cell infiltration into peripheral organs including the spread of cancer into soft tissue and bone; (iii) inhibition (i.e., slow to some extent and preferably stop) of tumor metastasis; (iv) inhibition, to some extent, of tumor growth; or (v) relief to some extent, of one or more of the symptoms associated with the specific cancer, including reduced morbidity and mortality and improvement in quality of life. To the extent the therapeutic combination may prevent growth and/or kill existing cancer cells, it may be cytostatic and/or cytotoxic. Reduction of these signs or symptoms may also be felt by the patient. The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic Malignancies include the diseases listed in Table 1, the WHO classification of Human Hematopoietic Malignancies; Tumors of Hematopoietic and Lymphoid Tissues (Jaffe E. S., Harris N. L., Stein H., Vardiman J. W. (Eds.) (2001): World Health Organization Classification of Tumours. Pathology and Genetics of Tumours of Hematopoietic and Lymphoid Tissues. IARC Press: Lyon) with the morphology code of the International Classification of Diseases (ICD-O). Behavior is coded /3 for malignant tumors and /1 for lesions of low or uncertain malignant potential.

TABLE 1

| | |
|---|---|
| I. | CHRONIC MYELOPROLIFERATIVE DISEASES |
| | Chronic myelogenous leukemia - ICD-O 9875/3 |
| | Chronic neutrophilic leukemia - ICD-O 9963/3 |
| | Chronic eosinophilic leukemia/hypereosinophilic syndrome - ICD-O 9964/3 |
| | Polycythemia vera - ICD-O 9950/3 |
| | Chronic idiopathic myelofibrosis - ICD-O 9961/3 |
| | Essential thrombocytemia - ICD-O 9962/3 |
| | Chronic Myeloproliferative disease, unclassifiable - ICD-O 9975/3 |
| II. | MYELODYSPLASTIC/MYELOPROLIFERATIVE DISEASES |
| | Chronic myelomonocytic leukemia - ICD-O 9980/3 |
| | Atypical chronic myelogenous leukemia - ICD-O 9876/3 |
| | Juvenile myelomonocytic leukemia - ICD-O 9946/3 |
| | Myelodysplastic/myeloproliferative diseases, unclassifiable - ICD-O 9975/3 |
| III. | MYELODYSPLASTIC SYNDROMES |
| | Refractory anemia - ICD-O 9980/3 |
| | Refractory anemia with ringed sideroblasts - ICD-O 9982/3 |
| | Refractory cytopenia with multilineage dysplasia - ICD-O 9985/3 |
| | Refractory anemia with excess blasts - ICD-O 9983/3 |
| | Myelodysplastic syndrome associated with isolated del(5q) chromosome abnormality - ICD-O 9986/3 |
| | Myelodysplastic syndrome, unclassifiable 9989/3 |
| IV. | ACUTE MYELOID LEUKEMIAS |
| | Acute myeloid leukemias with recurrent cytogenetic abnormalities |
| | AML with t(8; 21)(q22; q22), AML1/ETO - ICD-O 9896/3 |
| | AML with inv(16)(p13q22) or t(16; 16)(p13; q22), CBFb/MYH11 - ICD-O 9871/3 |
| | Acute promyelocytic leukemia (AML with t(15; 17)(q22; q12), PML-RARa and variants) - ICD-O 9866/3 |
| | AML with 11q23 (MLL) abnormalities - ICD-O 9897/3 |
| | Acute myeloid leukemia multilineage dysplasia- ICD-O 9895/3 |
| | Acute myeloid leukemia and myelodysplastic syndrome, therapy related - ICD-O 9920/3 |
| | Acute myeloid leukemia not otherwise categorised |
| | Acute myeloid leukemia, minimally differentiated - ICD-O 9872/3 |
| | Acute myeloid leukemia, without maturation - ICD-O 9873/3 |
| | Acute myeloid leukemia, with maturation - ICD-O 9874/3 |
| | Acute myelomonocytic leukemia - ICD-O 9867/3 |
| | Acute monoblastic and monocytic leukemia - ICD-O 9891/3 |
| | Acute erythroid leukemia - ICD-O 9840/3 |
| | Acute megakaryoblastic leukemia - ICD-O 9910/3 |
| | Acute basophilic leukemia - ICD-O 9870/3 |

TABLE 1-continued

|   |   |
|---|---|
|  | Acute panmyelosis with myelofibrosis - ICD-O 9931/3 |
|  | Myeloid sarcoma - ICD-O 9930/3 |
|  | Acute leukemia of ambiguous lineage - ICD-O 9805/3 |
| V. | B-CELL NEOPLASMS |
|  | Precursor hematopoietic neoplasm |
|  | Precursor B lymphoblastic leukemia/- ICD-O 9835/3 |
|  | lymphoma - ICD-O 9728/3 |
|  | Mature hematopoietic neoplasm |
|  | Chronic lymphocytic leukemia/- ICD-O 9823/3 |
|  | small lymphocytic lymphoma - ICD-O 9670/3 |
|  | hematopoietic prolymphocytic leukemia - ICD-O 9833/3 |
|  | Lymphoplasmacytic lymphoma - ICD-O 9671/3 |
|  | Splenic marginal zone lymphoma - ICD-O 9689/3 |
|  | Hairy cell leukemia - ICD-O 9940/3 |
|  | Plasma cell myeloma - ICD-O 9732/3 |
|  | Solitary plasmacytoma of bone - ICD-O 9731/3 |
|  | Extraosseous plasmacytoma - ICD-O 9734/3 |
|  | Extranodal marginal zone hematopoietic lymphoma of mucosa-associated lymphoid tissue (MALT-lymphoma) - ICD-O 9699/3 |
|  | Nodal marginal zone hematopoietic lymphoma - ICD-O 9699/3 |
|  | Follicular lymphoma - ICD-O 9690/3 |
|  | Mantle cell lymphoma - ICD-O 9673/3 |
|  | Diffuse large hematopoietic lymphoma - ICD-O 9680/3 |
|  | Mediastinal (thymic) large cell lymphoma - ICD-O 9679/3 |
|  | Intravascular large hematopoietic lymphoma - ICD-O 9680/3 |
|  | Primary effusion lymphoma - ICD-O 9678/3 |
|  | Burkitt lymphoma/- ICD-O 9687/3 |
|  | leukemia - ICD-O 9826/3 |
|  | hematopoietic proliferations of uncertain malignant potential |
|  | Lymphomatoid granulomatosis - ICD-O 9766/1 |
|  | Post-transplant lymphoproliferative disorder, pleomorphic - ICD-O 9970/1 |
| VI. | T-CELL AND NK-CELL NEOPLASMS |
|  | Precursor T-cell neoplasms |
|  | Precursor T lymphoblastic leukemia/- ICD-O 9837/3 |
|  | lymphoma - ICD-O 9729/3 |
|  | Blastic NK cell lymphoma - ICD-O 9727/3 |
|  | Mature T-cell and NK-cell neoplasms |
|  | T-cell prolymphocytic leukemia - ICD-O 9834/3 |
|  | T-cell large granular lymphocytic leukemia - ICD-O 9831/3 |
|  | Aggressive NK cell leukemia - ICD-O 9948/3 |
|  | Adult T-cell leukemia/lymphoma - ICD-O 9827/3 |
|  | Extranodal NK/T cell lymphoma, nasal type - ICD-O 9719/3 |
|  | Enteropathy type T-cell lymphoma - ICD-O 9717/3 |
|  | Hepatosplenic T-cell lymphoma - ICD-O 9716/3 |
|  | Subcutaneous panniculitis-like T-cell lymphoma - ICD-O 9708/3 |
|  | Mycosis fungoides - ICD-O 9700/3 |
|  | Sezary Syndrome - ICD-O 9701/3 |
|  | Primary cutaneous anaplastic large cell lymphoma - ICD-O 9718/3 |
|  | Peripheral T-cell lymphoma, unspecified -ICD-O 9702/3 |
|  | Angioimmunoblastic T-cell lymphoma - ICD-O 9705/3 |
|  | Anaplastic large cell lymphoma - ICD-O 9714/3 |
|  | T-cell proliferation of uncertain malignant potential |
|  | Lymphomatoid papulosis - ICD-O 9718/1 |
| VII. | HODGKIN LYMPHOMA |
|  | Nodular lymphocyte predominant Hodgkin lymphoma - ICD-O 9659/3 |
|  | Classical Hodgkin lymphoma - ICD-O 9650/3 |
|  | Nodular sclerosis classical Hodgkin lymphoma - ICD-O 9663/3 |
|  | Lymphocyte-rich classical Hodgkin lymphoma - ICD-O 9651/3 |
|  | Mixed cellularity classical Hodgkin lymphoma - ICD-O 9652/3 |
|  | Lymphocyte-depleted classical Hodgkin lymphoma - ICD-O 9653/3 |
| VIII. | HISTIOCYTIC AND DENDRITIC-CELL NEOPLASMS |
|  | Macrophage/histiocytic neoplasm |
|  | Histiocytic sarcoma - ICD-O 9755/3 |
|  | Dendritic cell neoplasms |
|  | Langerhans cell histiocytosis - ICD-O 9751/1 |
|  | Langerhans cell sarcoma - ICD-O 9756/3 |
|  | Interdigitating dendritic cell sarcoma/tumor - ICD-O 9757/3/1 |
|  | Follicular dendritic cell sarcoma/tumor - ICD-O 9758/3/1 |
|  | Dendritic cell sarcoma, not otherwise specified - ICD-O 9757/3 |
| IX. | MASTOCYTOSIS |
|  | Cutaneous mastocytosis |
|  | Indolent systemic mastocytosis - ICD-O 9741/1 |
|  | Systemic mastocytosis with associated clonal, hematological non-mast cell lineage disease - ICD-O 9741/3 |
|  | Aggressive systemic mastocytosis - ICD-O 9741/3 |
|  | Mast cell leukemia - ICD-O 9742/3 |
|  | Mast cell sarcoma - ICD-O 9740/3 |
|  | Extracutaneous mastocytoma - ICD-O 9740/1 |

A "B cell" is a lymphocyte that matures within the bone marrow, and includes a naïve B cell, memory B cell, or effector B cell (plasma cell). The B cell herein is a normal or non-malignant B cell.

The term "antibody" herein is used in the broadest sense and specifically covers monoclonal antibodies, polyclonal antibodies, multispecific antibodies (e.g. bispecific antibodies) formed from at least two intact antibodies, and antibody fragments, so long as they exhibit the desired biological activity.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic, as measured by TTP and/or response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive (alternation) administration in any order.

A "chemotherapeutic agent" is a biological (large molecule) or chemical (small molecule) compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted, conventional chemotherapy.

Examples of chemotherapeutic agents include: dexamethasone, thioTEPA, doxorubicin, vincristine, rituximab, cyclophosphamide, prednisone, melphalan, lenalidomide, bortezomib, rapamycin, and cytarabine.

Examples of chemotherapeutic agents also include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), doxorubicin (ADRIAMYCIN®), Akti-1/2, HPPD, rapamycin, and lapatinib (TYKERB®, Glaxo SmithKline).

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEX®, AstraZeneca), leucovorin (folinic acid), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), capecitabine (XELODA®, Roche), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thioTepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega I1, dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thioTepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKINO rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, rhuMab 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

The term "mammal" includes, but is not limited to, humans, mice, rats, guinea pigs, monkeys, dogs, cats, horses, cows, pigs, and sheep, and poultry.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—C (CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, biphenyl, indenyl, indanyl, 1,2-dihydronapthalene, 1,2,3,4-tetrahydronapthyl, and the like. Aryl groups are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), nitrogen (nitrogen-linked) or oxygen (oxygen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Carbon linked monocyclic heteroaryl" refers to a five- or six-membered, unsubstituted or substituted, monocyclic heteroaryl radical which contains 1, 2, 3 or 4 ring heteroatoms independently selected from N, O and S. The carbon linked monocyclic heteroaryl is attached to the C-2 position of the pyrimidine ring according to Formulas I at any carbon atom of the monocyclic heteroaryl $R^3$ group. Carbon linked monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Carbon linked monocyclic heteroaryls are optionally substituted independently with one or more substituents described herein.

"Carbon linked fused bicyclic $C_3$-$C_{20}$ heterocyclyl" and "carbon linked fused bicyclic $C_1$-$C_{20}$ heteroaryl" containing one or more heteroatoms independently selected from nitrogen, oxygen, and sulfur, differ only by their aromatic character, and have two rings fused together, i.e. share a common bond. Carbon linked fused bicyclic heterocyclyl and heteroaryl radicals are attached to the C-2 position of the pyrimidine ring according to Formulas I at any carbon atom of the fused bicyclic $C_3$-$C_{20}$ heterocyclyl or fused bicyclic $C_1$-$C_{20}$ heteroaryl group $R^3$ group. Carbon linked fused bicyclic heterocyclyl and heteroaryl radicals include, but are not limited to: 1H-indazole, 1H-indole, indolin-2-one, 1-(indolin-1-yl) ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine. Fused bicyclic heterocycles and fused bicyclic heteroaryls are optionally substituted independently with one or more substituents described herein.

The substituent groups that alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with include F, Cl, Br, I, CN, $CF_3$, $-NO_2$, oxo, $R^{10}$, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nOR^{10}$, $-NR^{10}R^{11}$, $-NR^{12}C(=Y)R^{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, $-(CR^{14}R^{15})_r-NR^{12}C(=O)(CR^{14}R^{15})NR^{10}R^{11}$, and $(CR^4R^5)_r-NR^{10}R^{11}$ A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

The term "synergistic" as used herein refers to a therapeutic combination which is more effective than the additive effects of the two or more single agents. Determination of a synergistic interaction between a Formula I compound, and one or more chemotherapeutic agent may be based on the results obtained from the assays described herein. The results of these assays are analyzed using the Chou and Talalay combination method and Dose-Effect Analysis with CalcuSyn software in order to obtain a Combination Index (Chou. and Talalay, Trends Pharmacol. Sci. 4:450-454; Chou, T. C. (2006) Pharmacological Reviews 68(3):621-681; Chou and Talalay, 1984, Adv. Enzyme Regul. 22:27-55). The combinations provided by this invention have been evaluated in several assay systems, and the data can be analyzed utilizing a standard program for quantifying synergism, additivism, and antagonism among anticancer agents. An exemplary program utilized is described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®., polyethylene glycol (PEG), and PLURONICS®.

The term "therapeutically effective amount" refers to an amount of the therapeutic combination effective to "treat" a disease or disorder in a subject or mammal. In the case of cancer, the therapeutically effective amount of the antagonist may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the antagonist may prevent growth and/or kill existing cancer cells, it may be cytostatic and/or cytotoxic.

A "growth inhibitory amount" of the therapeutic combination is an amount capable of inhibiting the growth of a cell, especially tumor, e.g., cancer cell, either in vitro or in vivo. A "growth inhibitory amount" of the therapeutic combination for purposes of inhibiting neoplastic cell growth may be determined empirically and in a routine manner.

A "cytotoxic amount" of the therapeutic combination is an amount capable of causing the destruction of a cell, especially tumor, e.g., cancer cell, either in vitro or in vivo.

The terms "cancer" and "cancerous" refer to or describe the physiological condition in mammals that is typically characterized by unregulated increase in cell number (generally referred to herein as cell growth), which can be due to abnormal increase in cell proliferation, abnormal decrease of cell death, or an imbalance of amounts of cell proliferation and cell death. Examples of cancer include, but are not limited to, hematopoietic cancers or blood-related cancers, such as lymphoma, leukemia, myeloma or lymphoid malignancies, but also cancers of the spleen and cancers of the lymph nodes.

The term "hyperproliferative" refers to disorders that are associated with some degree of abnormal cell proliferation. In one embodiment, a hyperproliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology, Third Edition; A. Victor Hoffbrand and John E. Pettit (eds.) (Harcourt Publishers Limited 2000) (see, in particular FIGS. 11.57, 11.58 and/or 11.59). More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphocytic leukemia and/or prolymphocytic leukemia and/or small lymphocytic lymphoma, hematopoietic prolymphocytic lymphoma, immunocytoma and/or lymphoplasmacytic lymphoma, marginal zone B cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large hematopoietic lymphoma, aggressive NHL (including aggressive front-line NHL and aggressive relapsed NHL), NHL relapsing after or refractory to autologous stem cell transplantation, primary mediastinal large hematopoietic lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) T-cell lymphoblastic leukemia and/or lymphoma, adult T-cell lymphoma and/or leukemia, T cell chronic lymphocytic leukemia and/or prolymphocytic leukemia, large granular lymphocytic leukemia, mycosis fungoides and/or Sezary syndrome, extranodal natural killer/T-cell (nasal type) lymphoma, enteropathy type T-cell lymphoma, hepatosplenic T-cell lymphoma, subcutaneous panniculitis like T-cell lymphoma, skin (cutaneous) lymphomas, anaplastic large cell lymphoma, angiocentric lymphoma, intestinal T cell lymphoma, peripheral T-cell (not otherwise specified) lymphoma and angioimmunoblastic T-cell lymphoma.

Non-Hodgkin's lymphoma thus includes hematopoietic lymphoma, B cell lymphoma, diffuse large B cell lymphoma, follicular lymphoma, small lymphocytic lymphoma, malignant lymphoma, malignant T cell lymphoma, anaplastic large cell lymphoma, and mucosal associated lymphoid tissue lymphoma.

Formula I Compounds

The present invention includes therapeutic combinations including Formula I compounds which have the structures:

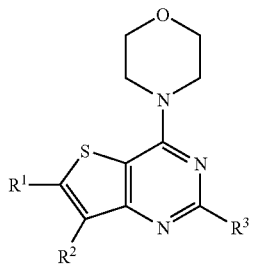

I or stereoisomers, geometric isomers, tautomers, or pharmaceutically acceptable salts thereof, where:

$R^1$ is selected from H, F, Cl, Br, I, CN, —$(CR^{14}R^{15})_m$NR$^{10}$R$^{11}$, —C$(CR^{14}R^{15})_n$NR$^{12}$C(=Y)R$^{10}$, —$(CR^{14}R^{15})_n$NR$^{12}$S(O)$_2$R$^{10}$, —$(CR^{14}R^{15})_m$OR$^{10}$, —$(CR^{14}R^{15})_n$S(O)$_2$R$^{10}$, —$(CR^{14}R^{15})_n$S(O)$_2$NR$^{10}$R$^{11}$, —C(OR$^{10}$)R$^{11}$R$^{14}$, —C(=Y)R$^{10}$, —C(=Y)OR$^{10}$, —C(=Y)NR$^{10}$R$^{11}$, —C(=Y)NR$^{12}$OR$^{10}$, —C(=O)NR$^{12}$S(O)$_2$R$^{10}$, —C(=O)NR$^{12}$(CR$^{14}$R$^{15}$)$_m$NR$^{10}$R$^{11}$, —NO$_2$, —NR$^{12}$C(=Y)R$^{11}$, —NR$^{12}$C(=Y)OR$^{11}$, —NR$^{12}$C(=Y)NR$^{10}$R$^{11}$, —NR$^{12}$S(O)$_2$R$^{10}$, —NR$^{12}$SO$_2$NR$^{10}$R$^{11}$, —SR$^{10}$, —S(O)$_2$R$^{10}$, —S(O)$_2$NR$^{10}$R$^{11}$, —SC(=Y)R$^{10}$, —SC(=Y)OR$^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —(CR$^{14}$R$^{15}$)$_n$, —NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is a carbon linked monocyclic heteroaryl, a carbon linked fused bicyclic $C_3$-$C_{20}$ heterocyclyl, or a carbon linked fused bicyclic $C_1$-$C_{20}$ heteroaryl, where the monocyclic heteroaryl, fused bicyclic $C_3$-$C_{20}$ heterocyclyl, and fused bicyclic $C_1$-$C_{20}$ heteroaryl are optionally substituted with one or more groups selected from F, Cl, Br, I, —CN, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —NR$^{12}$S(O)$_2$R$^{10}$, —C(=O)OR$^{10}$, —C(=O)NR$^{10}$R$^{11}$, $C_1$-$C_{12}$ alkyl and ($C_1$-$C_{12}$ alkyl)-OR$^{10}$;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached form a $C_2$-$C_{20}$ heterocyclic ring optionally substituted with one or more groups independently selected from oxo, (CH$_2$)$_m$OR$^{12}$, NR$^{12}$R$^{12}$, CF$_3$, F, Cl, Br, I, SO$_2$R$^{12}$, C(=O)R$^{12}$, NR$^{12}$C(=Y)R$^{12}$, NR$^{12}$S(O)$_2$R$^{12}$, C(=Y) NR$^{12}$R$^{12}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —(CH$_2$)$_n$-aryl, or $R^{14}$ and $R^{15}$ together with the atoms to which they are attached form a saturated or partially unsaturated $C_3$-$C_{12}$ carbocyclic ring;

where said alkyl, alkenyl, alkynyl, carbocyclyl, heterocyclyl, aryl, and heteroaryl, are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$^{10}$R$^{11}$, —NR$^{12}$C(=Y)R$^{10}$, —NR$^{12}$C(=Y)OR$^{11}$, —NR$^{12}$C(=Y)NR$^{10}$R$^{11}$, —(CR$^{14}$R$^{15}$)$_m$NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —SR$^{10}$, —S(O)R$^{10}$, —S(O)$_2$R$^{10}$, —S(O)$_2$NR$^{10}$R$^{11}$), —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

Y is O, S, or NR$^{12}$;

m is 0, 1, 2, 3, 4, 5 or 6; and n is 1, 2, 3, 4, 5 or 6.

Exemplary embodiments of Formula I compounds include wherein R$^1$ is —(CR$^{14}$R$^{15}$)$_m$NR$^{10}$R$^{11}$ where m is 1, and R$^{10}$ and R$^{11}$ together with the nitrogen to which they are attached form an optionally substituted $C_3$-$C_{20}$ heterocyclic ring. The $C_3$-$C_{20}$ heterocyclic ring may be piperazinyl, optionally substituted with one or more groups selected from NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, and $C_1$-$C_{12}$ alkyl.

Exemplary embodiments of Formula I compounds include wherein R$^1$ is not H.

Exemplary embodiments of Formula I compounds include wherein R$^2$ is H, CH$_3$, $C_3$-$C_{12}$ carbocyclyl, $C_2$-$C_{20}$ heterocyclyl, $C_6$-$C_{20}$ aryl, or $C_1$-$C_{20}$ heteroaryl. The $C_1$-$C_{20}$ heteroaryl may be a monocyclic heteroaryl group selected from 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl.

Exemplary embodiments of Formula I compounds include wherein R$^3$ is 2-aminopyrimidin-5-yl.

Exemplary embodiments of Formula I compounds include wherein R$^3$ is a bicyclic heteroaryl group selected from 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine.

Exemplary embodiments of Formula I compounds include wherein $R^3$ is 1H-indazol-4-yl.

An exemplary Formula I compound is named as 4-(2-(1H-indazol-4-yl)-6-((4-(methylsulfonyl)piperazin-1-yl)methyl)thieno[3,2-d]pyrimidin-4-yl)morpholine; registered as CAS Reg. No. 957054-30-7; described and claimed in US 2008/0076768; disclosed in Folkes et al (2008) Jour. of Med. Chem. 51(18):5522-5532; Belvin et al, American Association for Cancer Research Annual Meeting 2008, 99th: April 15, Abstract 4004; Folkes et al, American Association for Cancer Research Annual Meeting 2008, 99th: April 14, Abstract LB-146; Friedman et al, American Association for Cancer Research Annual Meeting 2008, 99th: April 14, Abstract LB-110; and has Formula Ia:

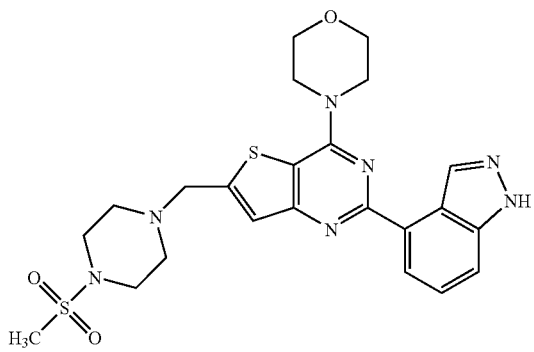

Ia

Another exemplary Formula I compound is named as (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one; disclosed and claimed in US 2008/0242665; and has Formula Ib:

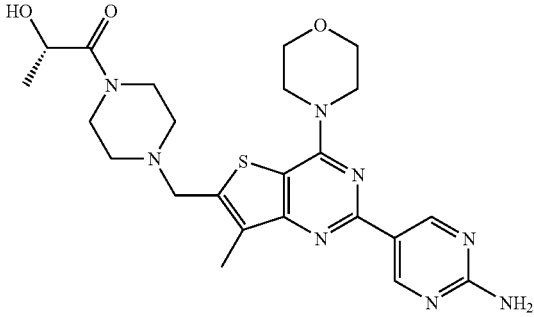

Ib

Preparation of Formula I Compounds

The Formula I compounds may be synthesized by synthetic routes that include processes analogous to those well-known in the chemical arts. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), or Beilsteins Handbuch der organischen Chemie, 4, Aufl. ed. Springer-Verlag, Berlin, including supplements (also available via the Beilstein online database).

Formula I compounds may be prepared using procedures to prepare other thiophenes and pyrimidines (U.S. Pat. No. 6,608,053; U.S. Pat. No. 6,492,383; U.S. Pat. No. 6,232,320; U.S. Pat. No. 6,187,777; U.S. Pat. No. 3,763,156; U.S. Pat. No. 3,661,908; U.S. Pat. No. 3,475,429; U.S. Pat. No. 5,075,305; US 2003/220365; GB 1393161; WO 93/13664); and other heterocycles, which are described in: Comprehensive Heterocyclic Chemistry, Editors Katritzky and Rees, Pergamon Press, 1984.

Formula I compounds may be converted into a pharmaceutically acceptable salt, and a salt may be converted into the free base compound, by conventional methods. Formula I compounds may be therapeutically effective as a free base or as a pharmaceutically acceptable salt, depending on the desired properties such as solubility, dissolution, hygroscopic nature, and pharmacokinetics. Examples of pharmaceutically acceptable salts include salts with inorganic acids such as hydrochloric acid, hydrobromic acid, hydroiodic acid, sulphuric acid, nitric acid and phosphoric acid; and organic acids such as methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid. The salt may be a mesylate, a hydrochloride, a phosphate, a benzenesulfonate or a sulfate. Salts may be mono-salts or bis-salts. For example, the mesylate salt may be the mono-mesylate or the bis-mesylate.

Formula I compounds and salts may also exist as hydrates or solvates.

Protection of functional groups (e.g., primary or secondary amine) of intermediates may be necessary in preparing Formula I compounds. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

For illustrative purposes, Schemes 1-7 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

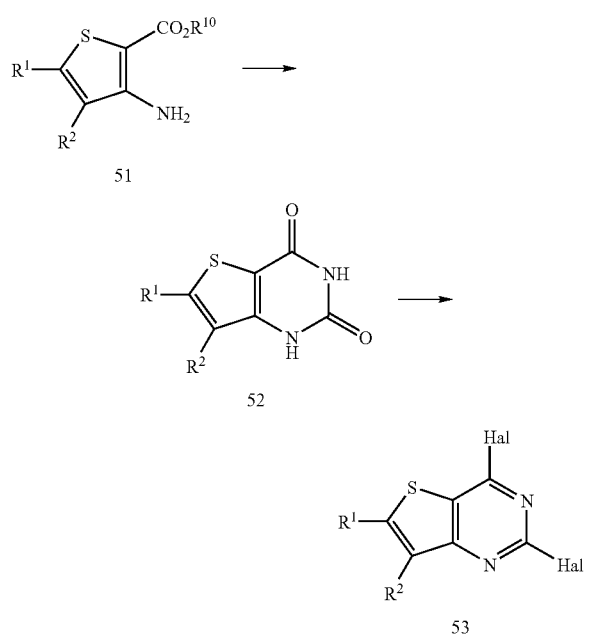

Scheme 1 shows a general method for preparation of the thienopyrimidine intermediates 53 from 2-carboxyester, 3-amino thiophene reagents 51, wherein Hal is Cl, Br, or I; and $R^1$, $R^2$, and $R^{10}$ are as defined for Formula I compounds, or precursors or prodrugs thereto.

Scheme 2

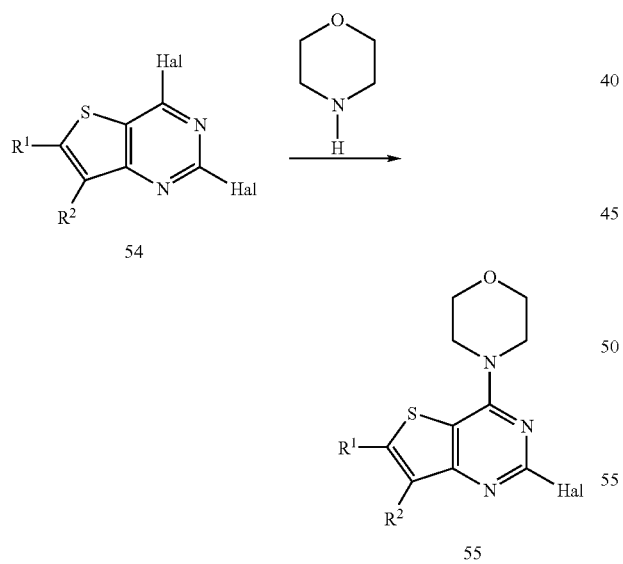

Scheme 2 shows a general method for selectively displacing a 4-halide from bis-halo thienopyrimidine intermediates 54 with morpholine under basic conditions in an organic solvent to prepare 2-halo, 4-morpholino thienopyrimidine compounds 55, wherein Hal is Cl, Br, or I; and $R^1$ and $R^2$ are as defined for Formula I compounds, or precursors or prodrugs thereto.

Scheme 3

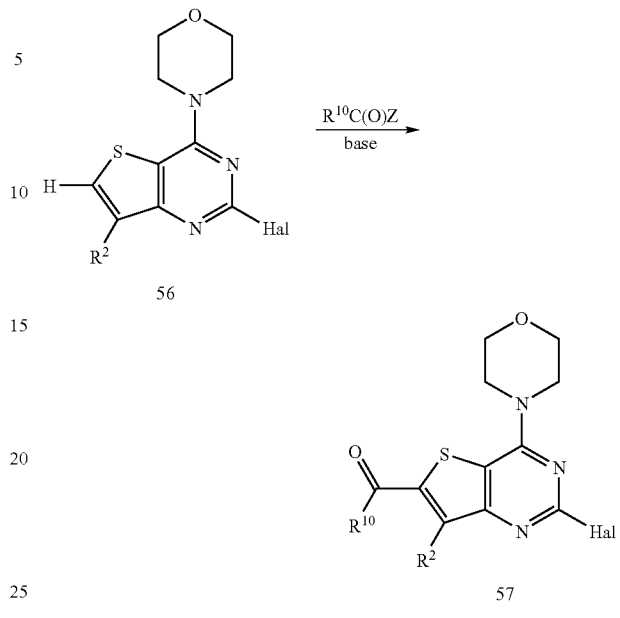

Scheme 3 shows a general method for derivatizing the 6-position of 2-halo, 4-morpholino, 6-hydrogen thienopyrimidine compounds 56 where $R^1$ is H. Treating 56 with a lithiating reagent to remove the 6 position proton, followed by adding an acylating reagent $R^{10}C(O)Z$ where Z is a leaving group, such as halide, NHS ester, carboxylate, or dialkylamino, gives 2-halo, 4-morpholino, 6-acyl thienopyrimidine compounds 57, wherein Hal is Cl, Br, or I; and $R^2$ and $R^{10}$ are as defined for Formula I compounds, or precursors or prodrugs thereto. An example of $R^{10}C(O)Z$ to prepare 6-formyl compounds ($R^{10}$=H) is N,N'-dimethylformamide (DMF).

Scheme 4

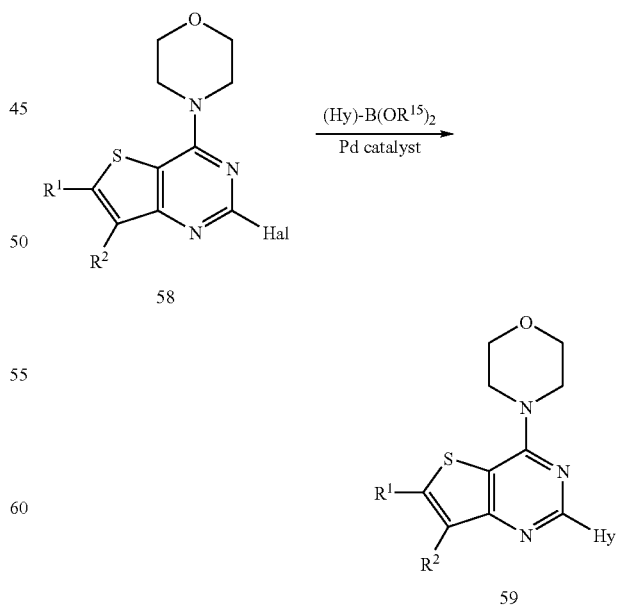

Scheme 4 shows a general method for Suzuki-type coupling of a 2-halo pyrimidine intermediates 58 with a monocyclic heteroaryl, fused bicyclic heterocyclyl or fused bicyclic heteroaryl boronate acid ($R^{15}$=H) or ester ($R^{15}$=alkyl) reagent to prepare the 2-substituted (Hy), 4-morpholino thienopyrimidine compounds 59 of Formula I wherein Hal is Cl, Br, or I; and $R^1$ and $R^2$ are as defined for Formula I compounds, or precursors or prodrugs thereto. For reviews of the Suzuki reaction, see: Miyaura et al. (1995) Chem. Rev. 95:2457-2483; Suzuki, A. (1999) J. Organomet. Chem. 576: 147-168; Suzuki, A. in Metal-Catalyzed Cross-Coupling Reactions, Diederich, F., Stang, P. J., Eds., VCH, Weinheim, Del. (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt-Bu)$_3$ (Owens et al (2003) Bioorganic & Med. Chem. Letters 13:4143-4145; Molander et al (2002) Organic Letters 4(11):1867-1870; U.S. Pat. No. 6,448,433).

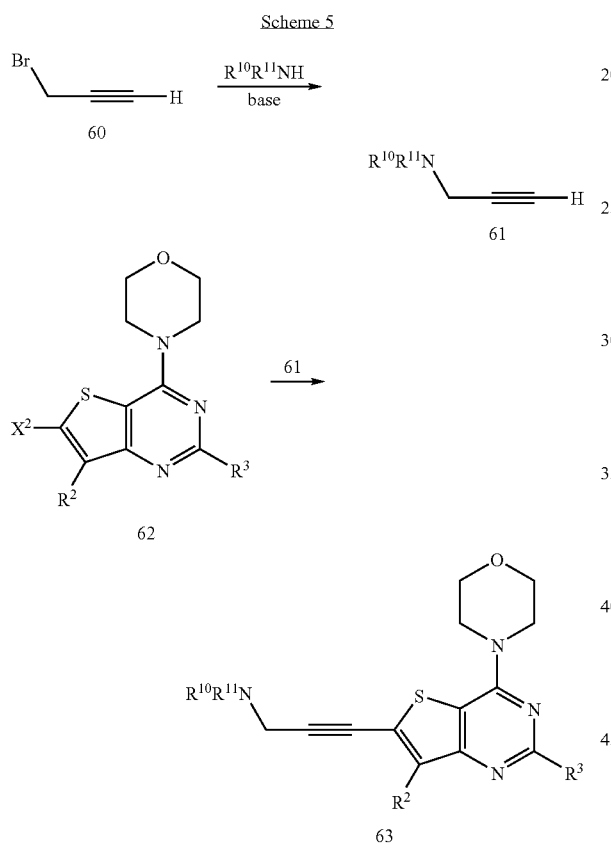

Scheme 5 shows a general method for the synthesis of alkynes 61, which can be used to prepare alkynylated derivatives of compounds 63. Propargylic amines 61 may be prepared by reaction of propargyl bromide 60 with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., *Comprehensive Organic Functional Group Transformations* (1995), 2:1039-1074; and Viehe, H. G., (1967) Angew. Chem., Int. Ed. Eng., 6(9):767-778. Alkynes 61 may subsequently be reacted with intermediates 62 ($X^2$=bromo or iodo) via Sonogashira coupling, to provide compounds 63, wherein $R^2$ and $R^3$ are as defined for Formula I compounds, or precursors or prodrugs thereto.

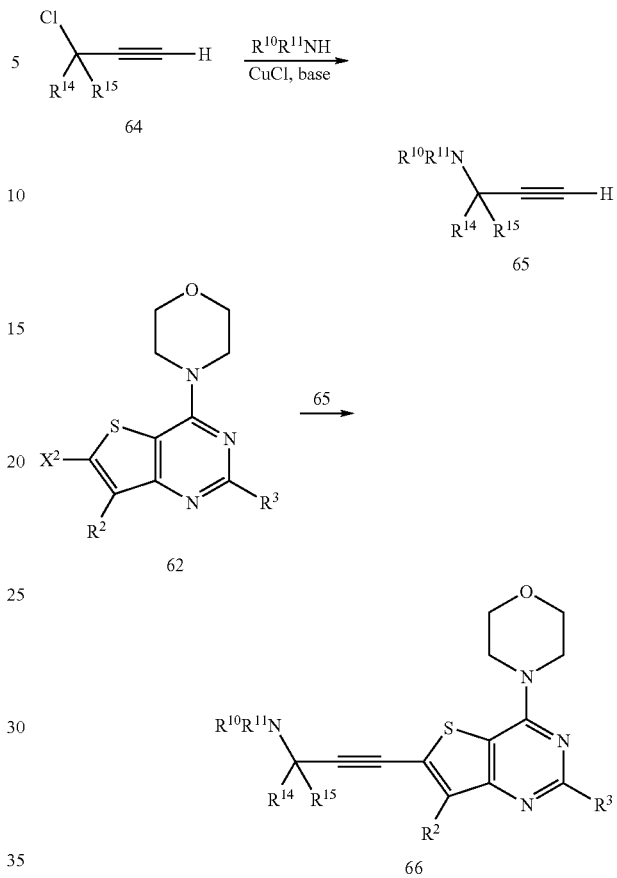

Scheme 6 shows a general method for the synthesis of alkynes 65, which can be used to prepare alkynylated derivatives of compounds 66. Gem-dialkyl propargylic amines 65 may be prepared using methods described by Zaragoza et al (2004) J. Med. Chem., 47:2833. According to Scheme 6, gem-dialkyl chloride 64 ($R^{14}$ and $R^{15}$ are independently methyl, ethyl or other alkyl group) can be reacted with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of CuCl and an appropriate base (e.g. TEA or the like) to provide the alkyne 65. Alkyne 65 can be reacted with intermediates 62 (via Sonogashira coupling) to provide compounds 66, wherein $R^2$ and $R^3$ are as defined for Formula I compounds, or precursors or prodrugs thereto.

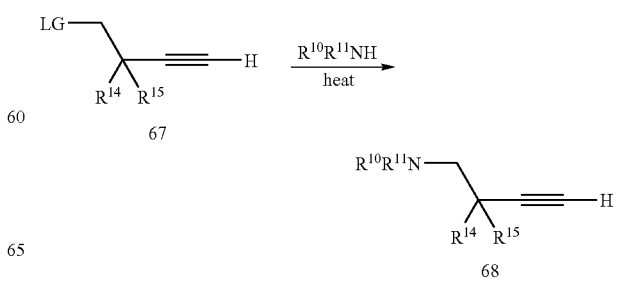

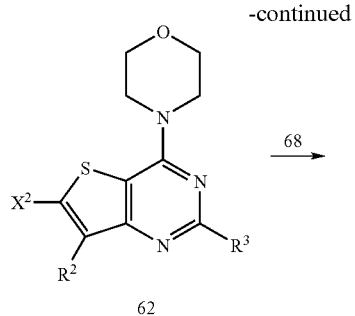

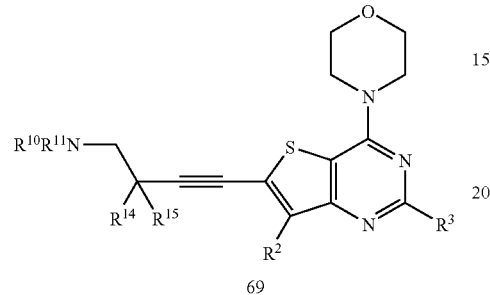

Scheme 7 shows a general scheme for the synthesis of alkynes 68, which can be used to prepare alkynylated derivatives of compounds 69. But-3-yn-1-amines 68 (wherein $R^{14}$ and $R^{15}$ are independently H, alkyl, aryl, heteroaryl, or $R^{14}$ and $R^{15}$ together with the carbon atom to which they are attached form a carbocyclic or heterocyclic ring) can be prepared from reaction of alkynes 67 (LG=tosylate or other leaving group) with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) using the protocol described by Olomucki M. et al (1960) Ann. Chim. 5:845. Alkynes 68 can subsequently be reacted with intermediates 62 via Sonogashira coupling, according to the descriptions provided for Schemes 5 and 6 to provide compounds 69, respectively, wherein $R^2$ and $R^3$ are as defined for Formula I compounds, or precursors or prodrugs thereto.

A pharmaceutically acceptable salt of a thienopyrimidine compound of Formula I may be prepared using conventional techniques. Typically the process comprises treating the thienopyrimidine of Formula I as defined above with a suitable acid in a suitable solvent.

In the process of the invention as defined above, both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, such as $NaBH(OAc)_3$, $NaBH_4$ or NaCNBH$_4$.

Chemotherapeutic Agents

Certain chemotherapeutic agents have demonstrated surprising and unexpected properties in combination with Formula I compounds in inhibiting cellular proliferation in vitro and in vivo. Such chemotherapeutic agents include: dexamethasone, thioTEPA, doxorubicin, vincristine, rituximab, cyclophosphamide, prednisone, melphalan, lenalidomide, bortezomib, rapamycin, and cytarabine.

Dexamethasone is a potent glucocorticoid steroid hormone, with anti-inflammatory and immunosuppressant activity. In oncology, dexamethasone is given to cancer patients undergoing chemotherapy, to counteract certain side-effects of their antitumor treatment. Dexamethasone can augment the antiemetic effect of 5-HT$_3$ receptor antagonists like ondansetron. Dexamethasone is also used in certain hematological malignancies, especially in the treatment of multiple myeloma, in which dexamethasone is given alone or together with thalidomide (thal-dex) or a combination of Adriamycin (doxorubicin) and vincristine (VAD). In brain tumours (primary or metastatic), dexamethasone is used to counteract the development of edema, which could eventually compress other brain structures. Dexamethasone is named as (8S,9R,10S,11S,13S,14S,16R,17R)-9-fluoro-11,17-dihydroxy-17-(2-hydroxyacetyl)-10,13,16-trimethyl-6,7,8,11,12,14,15,16-octahydrocyclopenta[a]phenanthren-3-one (CAS Reg. No. 50-02-2) and has the structure:

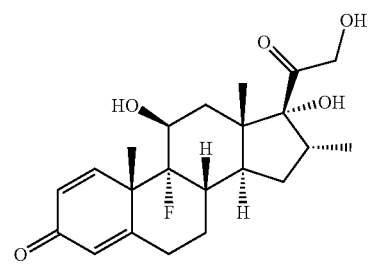

thioTEPA (tespa, thiophosphoamide, tespamin, tspa, tifosyl, THIOPLEX®) is an alkylating chemotherapeutic agent used to treat breast cancer, ovarian cancer, and bladder cancer (Maanen et al (2000) Cancer Treat Rev 26(4):257-68; U.S. Pat. No. 2,670,347). It is also used as conditioning for bone marrow transplantation ThioTEPA is named as N,N'N'-triethylenethiophosphoramide, phosphinothioylidynetrisaziridine, or 1,1',1"-phosphorothioyltriaziridine (CAS Reg. No. 52-24-4) and has the structure:

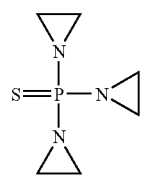 [SMILES: S=P(N1CC1)(N1CC1)N1CC1]

Doxorubicin (ADRIAMYCIN®, hydroxyldaunorubicin) is a DNA-interacting drug widely used in chemotherapy since the 1960s. It is an anthracycline antibiotic and structurally related to daunomycin, which also intercalates DNA. Doxorubicin is commonly used in the treatment of a wide range of cancers. Doxorubicin is named as (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, (CAS Reg. No. 23214-92-8) and has the structure:

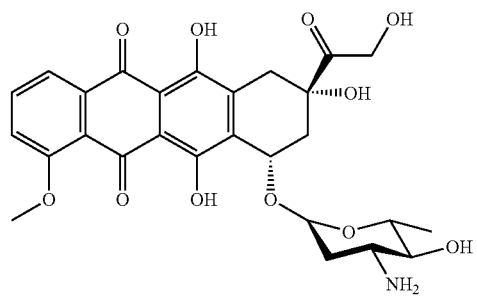

Vincristine (22-Oxovincaleukoblastine; leurocristine, VCR, LCR sulfate form: Vincristine sulfate, Kyocristine, ONCOVIN® (Lilly), Vincosid, Vincrex), is a vinca alkaloid from the Madagascar periwinkle *Catharanthus roseus*, formerly *Vinca rosea* (Johnson et al (1963) Cancer Res. 23:1390-1427; Neuss et al (1964) J. Am. Chem. Soc. 86:1440). Along with semisynthetic derivatives, vindesine and vinorelbine (NAVELBINE®, vincristine inhibits mitosis in metaphase by binding to tubulin and preventing the cell from making spindles necessary to move chromosomes as the cell divides. Vincristine is a chemotherapy drug that is given as a treatment for some types of cancer including leukemia, lymphoma, breast and lung cancer. Vincristine (leurocristine, VCR) is most effective in treating childhood leukemias and non-Hodgkin's lymphomas, where vinblastine (vincaleukoblastine, VLB) is used to treat Hodgkin's disease. Vincristine (CAS number 57-22-7) has the structure:

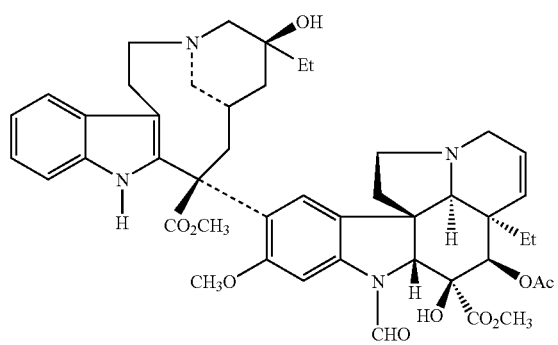

Rituximab (RITUXAN®, Genentech/Biogen Idec; MABTHERA®, Roche, REDITUX®, CAS Reg. No. 174722-31-7) is a genetically engineered chimeric murine/human monoclonal antibody directed against the CD20 antigen. Rituximab is the antibody called "C2B8" in U.S. Pat. No. 5,736,137. Rituximab is indicated for the treatment of patients with relapsed or refractory low-grade or follicular, CD20-positive, B-cell NHL. Rituximab binds to cell surface CD-20 and results in B-cell depletion (Cartron et al (2002) Blood 99: 754-758; Idusogie et al (2000) J. Immunol. 164: 4178-4184; Grillo-Lopez A J, et al (1999) Semin Oncol; 26:66-73; U.S. Pat. No. 5,736,137). RITUXAN (U.S. Pat. No. 5,677,180; U.S. Pat. No. 5,736,137) is the most widely used monoclonal antibody in hematopoietic malignancies and is established in widespread clinical practice. RITUXAN first received FDA approval in 1997 for the treatment of relapsed or refractory, low-grade or follicular, CD20-positive, B-cell non-Hodgkin's lymphoma (NHL). It was also approved in the European Union under the trade name MabThera® in June 1998. In February 2006, RITUXAN also received FDA approval in combination with methotrexate to reduce signs and symptoms in adult patients with moderately-to-severely-active rheumatoid arthritis who have had an inadequate response to one or more TNF antagonist therapies. The amino acid sequence of rituximab antibody (also designated C2B8) and exemplary methods for its production via recombinant expression in Chinese Hamster Ovary (CHO) cells are disclosed in U.S. Pat. No. 5,736,137.

Cyclophosphamide (Cytoxan, Neosar, Revimmune, cyclophosphane, B-518, Cycloblastin, Cyclostin, Endoxan, Procytox, Sendoxan, cytophosphane) is a nitrogen mustard alkylating agent, from the oxazophorines group used to treat various types of cancer and some autoimmune disorders ("A Review of Cyclophosphamide", D. L. Hill (1975) Charles C. Thomas, Springfield, 340 pp; IARC Monographs (1975) 9:135-156; Fraiser et al (1991) Drugs 42:781-795; Colvin, OmM. (1999) Curr. Pharmaceut. Design 5:555-560). Cyclophosphamide is a prodrug converted in the liver to active forms that have chemotherapeutic activity. The main use of cyclophosphamide is together with other chemotherapy agents in the treatment of lymphomas, some forms of leukemia, and some solid tumors (Shanafelt et al (2007) Cancer 109(11): 2291-8; Brock N (1996) Cancer 78(3):542-7). It is a chemotherapy drug that works by slowing or stopping cell growth and by decreasing the immune system response to various diseases.

Cyclophosphamide is named as N,N-bis(2-chloroethyl)-1,3,2-oxazaphosphinan-2-amine 2-oxide, N,N-bis(2-chloroethyl)tetrahydro-2H-1,3,2-oxazaphosphorin-2-amine-2-oxide; 1-bis(2-chloroethyl)amino-1-oxo-2-aza-5-oxaphosphoridin monohydrate; bis(2-chloroethyl)-phosphamide cyclic propanolamide ester; or N,N-bis(beta-chloroethyl)-N',O-propylenephosphoric acid ester diamide, including hydrate forms (CAS number 50-18-0), and has the structure:

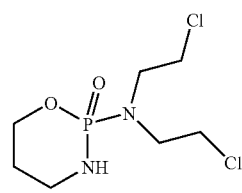 [SMILES: O=P1(N(CCCl)CCCl)NCCCO1]

Prednisone (Meticorten, Sterapred, Sterapred DS, retrocortine, Colisone, Cortancyl, Dacortin, Decortin, Deltacortene, Deltacortone, Deltasone, Deltison, Di-Adreson, Encorton, Hostacortin, Meticorten, Orasone, Rectodelt, Sone, or Ultracorten) is a synthetic corticosteroid drug (U.S. Pat. No. 2,897,216; U.S. Pat. No. 2,837,464; U.S. Pat. No. 3,134,718; U.S. Pat. No. 2,579,479). Prednisone is a prodrug converted in the liver into prednisolone (CAS Reg. No. 50-24-8), an 11-hydroxyl analog, and has a mainly glucocorticoid effect. Prednisone may be administered orally or by injection. Prednisone is particularly effective as an immunosuppressant and is used to treat autoimmune diseases, inflammatory diseases (such as severe asthma, allergies, poison ivy, dermatitis, lupus, rheumatoid arthritis, and Crohn's disease, and to prevent and treat rejection in organ transplantation. Prednisone is used to treat cancer, including acute lymphoblastic leukemia, Non-Hodgkin's lymphomas, and multiple myeloma. Prednisone is named as 17-hydroxy-17-(2-hydroxyacetyl)-10,13-dimethyl-7,8,9,10,12,13,14,15,16,17-decahydro-6H-cyclopenta[a]phenanthrene-3,11-dione; or 17,21-dihydroxypregna-1,4-diene-3,11,20-trione; 1,4-pregnadiene-17alpha,21-diol-3,11,20-trione; (CAS number 53-03-2), and has the structure:

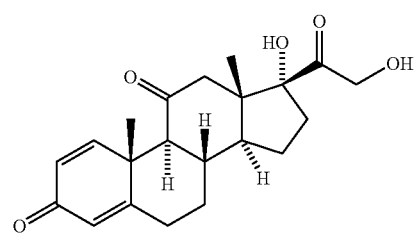

Melphalan (L-phenylalanine mustard; alanine nitrogen mustard; L-PAM; melfalan; L-sarcolysine; NSC-8806;

CB-3025; ALKERAN® (Glaxo SmithKline); Sarcoclorin) is a nitrogen mustard alkylating agent type of chemotherapeutic (U.S. Pat. No. 3,032,584; U.S. Pat. No. 3,032,585). Melphalan is used primarily to treat multiple myeloma, ovarian cancer and melanoma (IARC Monographs (1975) 9:167-180; Furner et al (1980) Cancer Treat. Rep. 64:559-574). Melphalan is named as 2-amino-3-[4-[bis(2-chloroethyl)amino]phenyl]-propanoic acid; 4-[bis(2-chloroethyl)amino]-L-phenylalanine; or p-di(2-chloroethyl)amino-L-phenylalanine (CAS Reg. No. 148-82-3) and has the structure:

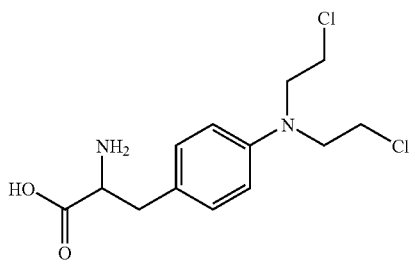 [SMILES: NC(Cc1ccc(N(CCCl)CCCl)cc1)C(=O)O]

Lenalidomide (REVLIMID®, CC5013, Revimid, Celgene Inc.) is a derivative of thalidomide and introduced in 2004 (U.S. Pat. No. 5,635,517, U.S. Pat. No. 6,281,230) to treat both inflammatory disorders and cancers. There are multiple mechanisms of action, including a direct anti-tumor effect, inhibition of the microenvironment support for tumor cells, and an immunomodulatory role. In vitro, lenalidomide induces tumor cell apoptosis directly and indirectly by inhibition of bone marrow stromal cell support, by anti-angiogenic and anti-osteoclastogenic effects, and by immunomodulatory activity. Lenalidomide was initially intended as a treatment for multiple myeloma, for which thalidomide is an accepted therapeutic modality, but has also shown efficacy in the class of hematological disorders known as myelodysplastic syndromes (Richardson et al (2002) Blood 100:3063; Bartlett et al (2004) Nature Rev. 4:314-322; Mitsiades et al (2004) Curr. Opin. Invest. Drugs 5:635-647; Armoiry et al. (2008) J of Clin Pharmacy & Therapeutics 33:219-226; List et al (2005) N. Engl. Jour. Med. 352:549-57). Lenalidomide is named as 3-(4-amino-1-oxoisoindolin-2-yl)piperidine-2,6-dione; 3-(4-amino-1,3-dihydro-1-oxo-2H-isoindol-2-yl)-2,6-piperidinedione; 1-oxo-2-(2,6-dioxopiperidin-3-yl)-4-aminoisoindoline (CAS Reg. No. 191732-72-6) and has the structure:

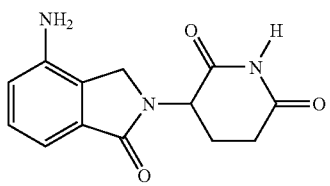 [SMILES: Nc1cccc2c1CN(C1CCC(=O)NC1=O)C2=O]

Bortezomib (MG-341, PS-341, VELCADE®, Millenium Pharm.) is a boronic acid proteasome inhibitor approved in the US for treating relapsed multiple myeloma and mantle cell lymphoma. (WO 96/13266; U.S. Pat. No. 5,780,454; U.S. Pat. No. 6,083,903; U.S. Pat. No. 6,297,217; U.S. Pat. No. 6,617,317; U.S. Pat. No. 6,713,446; U.S. Pat. No. 6,747,150; U.S. Pat. No. 6,958,319; U.S. Pat. No. 7,119,080). The boron atom in bortezomib binds the catalytic site of the 26S proteasome with high affinity and specificity. In normal cells, the proteasome regulates protein expression and function by degradation of ubiquitinylated proteins, and also cleanses the cell of abnormal or misfolded proteins. (Adams et al (2004) Cancer Invest 22(2):304-11; Bonvini (2007). Leukemia 21(4):838-42). Bortezomib is named as [(1R)-3-methyl-1-({(2S)-3-phenyl-2-[(pyrazin-2-ylcarbonyl)amino]propanoyl}amino)butyl]boronic acid; (R)-3-methyl-14(S)-3-phenyl-2-(pyrazine-2-carboxamido)propanamido) butylboronic acid; or [(1R)-3-methyl-1-[[(2S)-1-oxo-3-phenyl-2-[(pyrazinylcarbonyl)amino]propyl]amino]butyl]-boronic acid (CAS Reg. No. 179324-69-7) and has the structure:

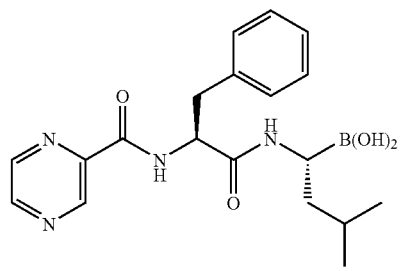 [SMILES: CC(C)C[C@H](NC(=O)[C@H](Cc1ccccc1)NC(=O)c1cnccn1)B(O)O]

Rapamycin (sirolimus, RAPAMUNE®) is an immunosuppressant drug used to prevent rejection in organ transplantation, and is especially useful in kidney transplants. Rapamycin is a macrolide antibiotic produced by the bacterium *Streptomyces hygroscopicus* in a soil sample obtained from an island called Rapa Nui, better known as Easter Island (Pritchard D I (2005). Drug Discovery Today 10 (10): 688-691). Rapamycin inhibits the response to interleukin-2 (IL-2) and thereby blocks activation of T- and hematopoietics. The mode of action of rapamycin is to bind the cytosolic protein FK-binding protein 12 (FKBP12). The rapamycin-FKBP12 complex inhibits the mammalian target of rapamycin (mTOR) pathway through directly binding the mTOR Complex1 (mTORC1). mTOR is also called FRAP (FKBP-rapamycin associated protein) or RAFT (rapamycin and FKBP target). Rapamycin analogs ("Rapalogs") include Temsirolimus (CCI-779, Wyeth), Everolimus (RAD001, Novartis), Deforolimus (AP23573, MK-8669, Ariad, Merck). Rapamycin is named as (3S,6R,7 E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone (CAS Reg. No. 53123-88-9), and has the structure:

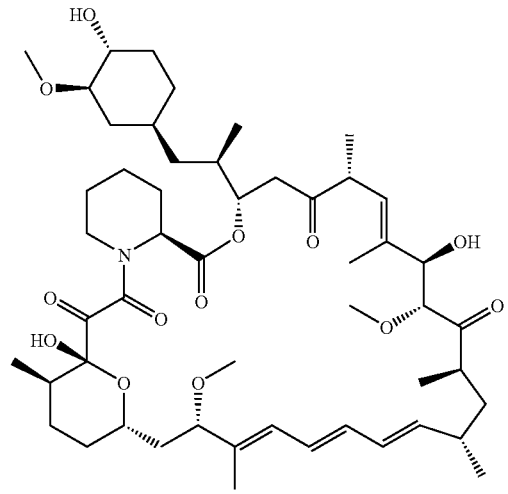 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

Cytarabine (cytosine arabinoside, Ara-C, CYTOSAR-U®, Upjohn) is used primarily in the treatment of hematological malignancies, including acute myeloid leukemia (AML) and NHL (U.S. Pat. No. 3,116,282; Shen et al (1965) J. Org. Chem. 835); Capizzi, R. L. (1996) Invest. New Drugs 14:249-256; Grant S. (1998) Adv. Cancer Res. 72:197-233). Cytarabine is named as 4-amino-1-((2R,3S,4S,5R)-3,4-dihydroxy-5-(hydroxymethyl)tetrahydrofuran-2-yl)pyrimidin-2(1H)-one; 4-amino-1-beta-D-arabinofuranosyl-2(1H)-pyrimidinone; 1-beta-D-arabinofuranosylcytosine; (CAS Reg. No. 147-94-4) and has the structure:

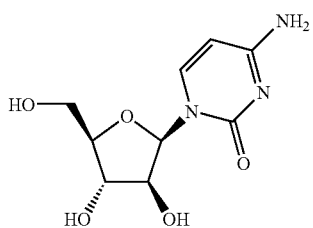 [SMILES: Nc1ccn([C@@H]2O[C@H](CO)[C@@H](O)[C@@H]2O)c(=O)n1]

CHOP is an acronym for a chemotherapy regimen used in the treatment of non-Hodgkin lymphoma comprising cyclophosphamide, doxorubicin, vincristine, and prednisone/prednisolone (Fisher et al (1993) N Engl J Med 328(14):1002-6). CHOP is commonly administered in cycles of 4 weeks. A common treatment regimen is for at least 6 cycles.

Biological Evaluation

Certain Formula I compounds bind specifically to PI3 kinase isoforms and inhibit the proliferation of tumor cells (US 2008/0207611; US 2008/0039459; US 2008/0076768; US 2008/0076758; US 2008/0242665; US 2008/0269210). Certain exemplary Formula I compounds have PI3K binding activity $IC_{50}$ values less than 10 nM. Certain Formula I compounds have tumor cell-based activity $EC_{50}$ values less than 100 nM.

Certain exemplary therapeutic combinations of Formula I compounds and chemotherapeutic agents described herein were assayed for in vitro activity against tumor cells (Example 15). Certain Formula I compounds bind the p110α isoform at IC50 less than 1 micromole and show single-agent in vivo tumor growth inhibition in mouse xenograft models. Accordingly, Formula I compounds may be used to treat a disease or disorder arising from abnormal cell growth, function or behavior as single agents or in combination therapy with one or more chemotherapeutic agents.

Mutations in KRAS, NRAS, BRAF and PIK3CA activate two of the major pathways mediating proliferation and anti-apoptotic signaling in cancer cells. As such, mutations in these genes might constitute companion diagnostic tests for targeted agents that inhibit key nodes in these pathways, since the presence of a mutation may serve as a sign of pathological activation and dependence on a given pathway in a particular tumor. The mutation status for these genes, and others, in a large panel of cell lines of diverse tissues of origin may yield a correlation with response to selective inhibitors of MEK and PI3 kinase. In addition, mutation detection may be conducted on clinical samples consisting of small amounts of heterogeneous fixed tumor tissues, which may be analyzed using allele specific Taqman assays for the most prevalent substitutions in KRAS, NRAS, BRAF and PI3 kinase.

Figure 1B:
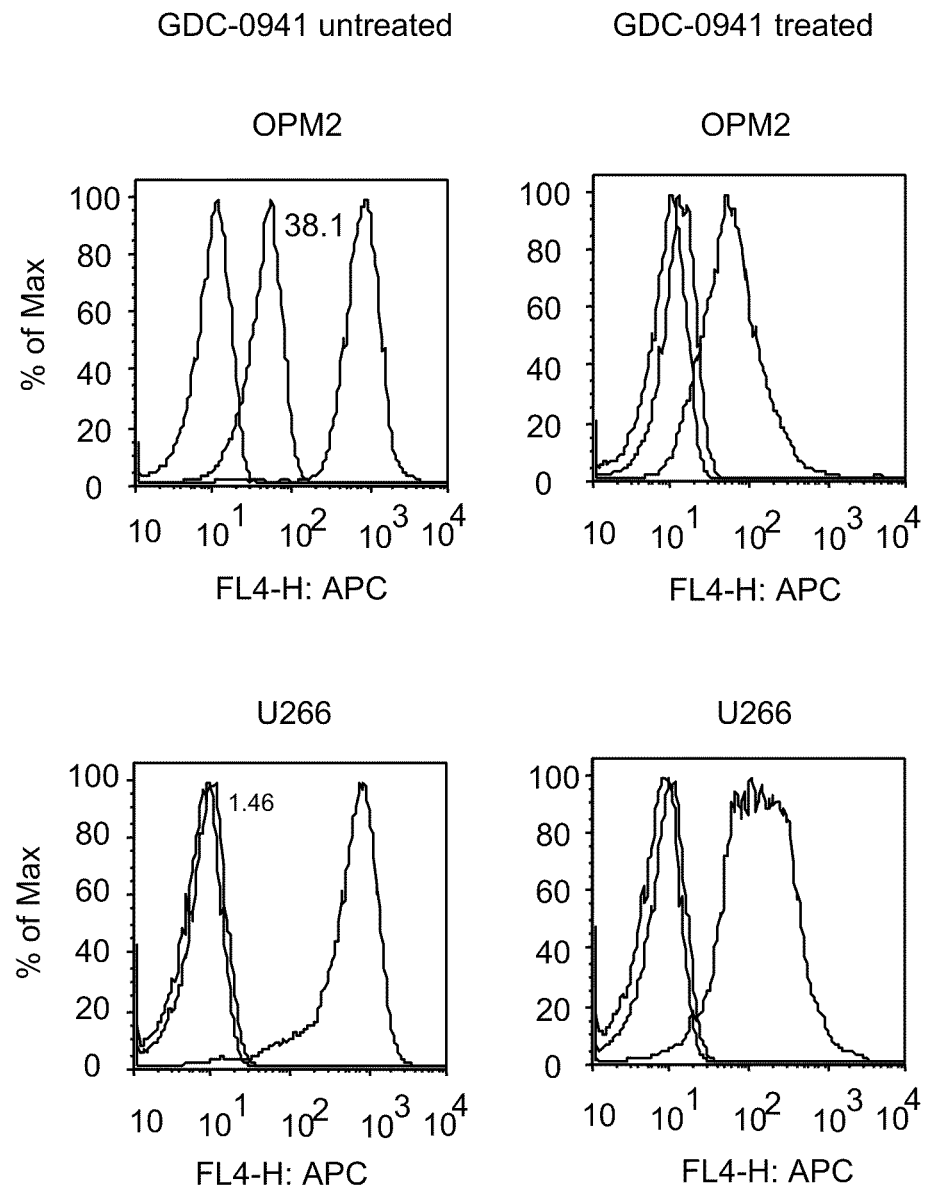

FIG. 1 shows reduction of pharmacodynamic (PD) markers measured by FACS flow cytometry with Formula Ia (GDC-0941) treated (right column) and untreated (left column) cells, DoHH2 (lymphoma cells), WSU-DLCL2 (lymphoma cells), OPM2 (multiple myeloma cells), and U266 (multiple myeloma cells). Example 18 provides a FACS protocol for intracellular detection of phospho-AKT (p-Akt) and p-S6 ribosomal protein (p-S6RP) post GDC-0941 treatment. Cells were treated in vitro with 5 µM GDC-0941 for 4 hrs. Three of the cell lines showed evidence of PI3K pathway activation as evidenced by high levels of p-AKT and all four show evidence of distal pathway activation as evidenced by high levels of phospho-S6 ribosomal protein signal in untreated cells (left columns). In the right column, cells treated with GDC-0941 have abolished p-AKT signal and reduced or abolished p-S6RP signal. The remaining signals for pS6rp are consistent with a model that PI3k activity is partly responsible for this phosphorylation event. Collectively, these data indicate that the PI3k pathway is activated in these cell types and that GDC-0941 has potent inhibitory activity on the PI3k pathway in intact cells.

Figure 2:
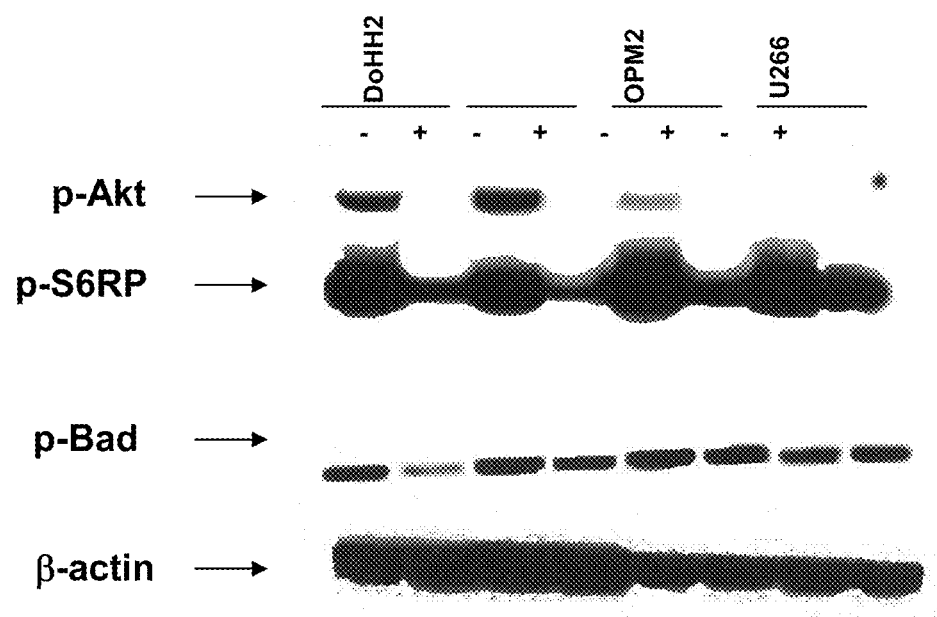
FIG. 2 shows reduction of pharmacodynamic (PD) markers p-AKT, p-S6RP, p-Bad, and beta-actin in cells DoHH2, WSU-DLCL2, OPM2, and U266 as measured by SDS-polyacrylamide gel electrophoresis and western blotting in cell lines treated in vitro with 5 µM GDC-0941 for 4 hrs.

FIG. 2 shows reduction of pharmacodynamic (PD) markers p-AKT, p-S6RP, p-Bad, and in cells DoHH2, WSU-DLCL2, OPM2, and U266 as measured by SDS-polyacrylamide gel electrophoresis and western blotting in cell lines treated in vitro with 5 µM GDC-0941 for 4 hrs. Example 17 provides a protocol for detection by Western blotting of p-Akt, p-BAD and p-S6 ribosomal protein post GDC-0941 treatment of B cell and myeloma cell lines. Cells were treated as indicated and lysates analyzed by Western Blotting. Beta Actin blotting indicates approximately equal loading of lysates in each lane. Three of the cell lines showed evidence of PI3K pathway activation as evidenced by high levels of p-AKT and all four show evidence of distal pathway activation as evidenced by high levels of p-S6RP signal in untreated cells. Signals for both p-AKT and p-S6RP were significantly reduced (where present) by treatment with GDC-0941 indicating that the PI3K pathway has been activated in these cells and that GDC-0941 has significant inhibitory activity on the pathway in intact cells. Levels of both PD markers follow the same rank order and are well correlated between FIG. 1 and FIG. 2.

Pharmacodynamic and pharmacokinetic properties of absorption, distribution, metabolism, and excretion (ADME) were measured for certain exemplary compounds by assays including: Caco-2 Permeability, Hepatocyte Clearance, Cytochrome P450 Inhibition, Cytochrome P450 Induction, Plasma Protein Binding, and hERG channel blockage.

The invention includes a method for determining compounds to be used in combination for the treatment of cancer comprising: a) administering a therapeutic combination of a compound having Formula I, and a chemotherapeutic agent to an in vitro tumor cell line and, b) measuring a synergistic or non-synergistic effect.

In Vitro Cell Proliferation Assays

The cytotoxic or cytostatic activity of Formula I exemplary compounds was measured by: establishing a proliferating mammalian tumor cell line in a cell culture medium, adding a Formula I compound, culturing the cells for a period from about 6 hours to about 5 days; and measuring cell viability (Example 15). Cell-based in vitro assays were used to measure viability, i.e. proliferation ($IC_{50}$), cytotoxicity ($EC_{50}$), and induction of apoptosis (caspase activation).

The in vitro potency of the combinations of Formula I compounds with chemotherapeutic agents was measured by the cell proliferation assay of Example 15; the CellTiter-Glo® Luminescent Cell Viability Assay, commercially available from Promega Corp., Madison, Wis. This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of Formula I exemplary compounds and combinations with chemotherapeutic agents were measured by the CellTiter-Glo® Assay (Example 15) against the tumor cell lines in FIGS. 3-6. $EC_{50}$ values were established for the tested compounds and combinations. The range of in vitro cell potency activities was about 100 nM to about 10 µM.

Figure 4:
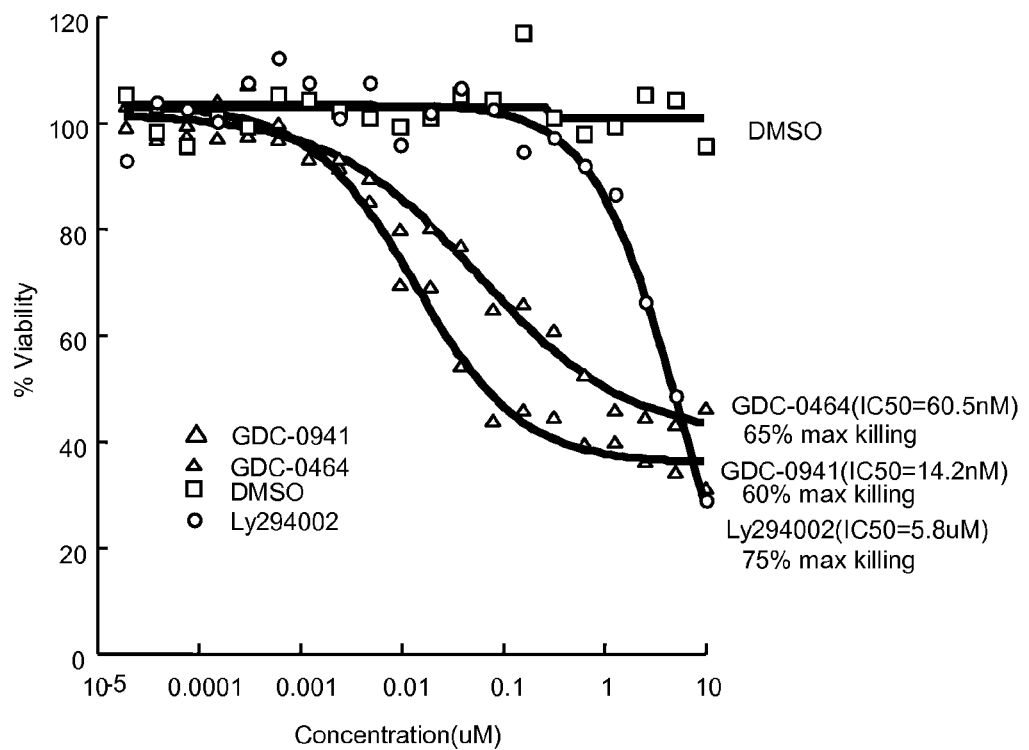
FIG. 4 shows the effect of PI3K single agent inhibitors on primary follicular lymphoma cells from patient NHL600-A876 cells by in vitro cell survival and proliferation assays (Cell-Titer Glo®, Promega Corp., Madison, Wis.) measuring viable cells over varying concentrations ($10^{-5}$ to 10 µMolar) of Formula Ia (GDC-0941), GDC-0464, and LY294002.
Figure 5:
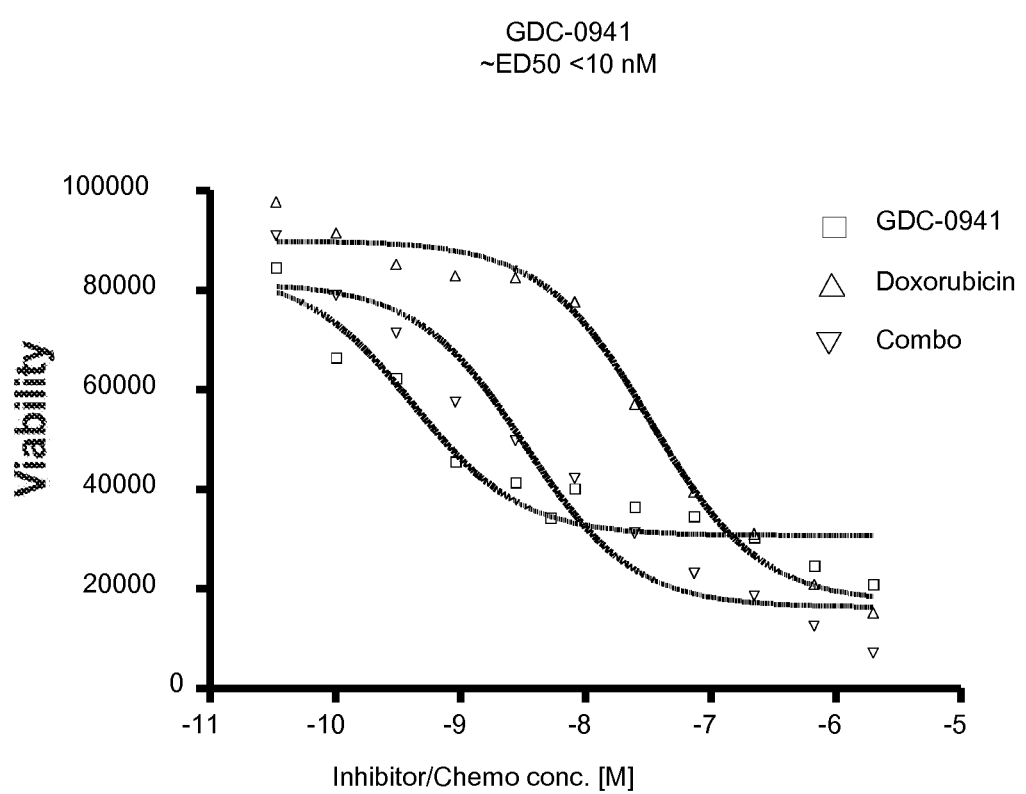
FIG. 5 shows the effect of a PI3K single agent inhibitor, Formula Ia (GDC-0941), and in combination with doxorubicin, on primary diffuse large B-cell lymphoma (DLBCL) cells from patient NHL640-A055. Cell viability was measured by in vitro cell survival and proliferation assays (Cell-Titer Glo®) over varying concentrations ($10^{-5}$ to 20 µMolar) of Formula Ia, doxorubicin, and the combination of Formula Ia and doxorubicin.
Figure 6:
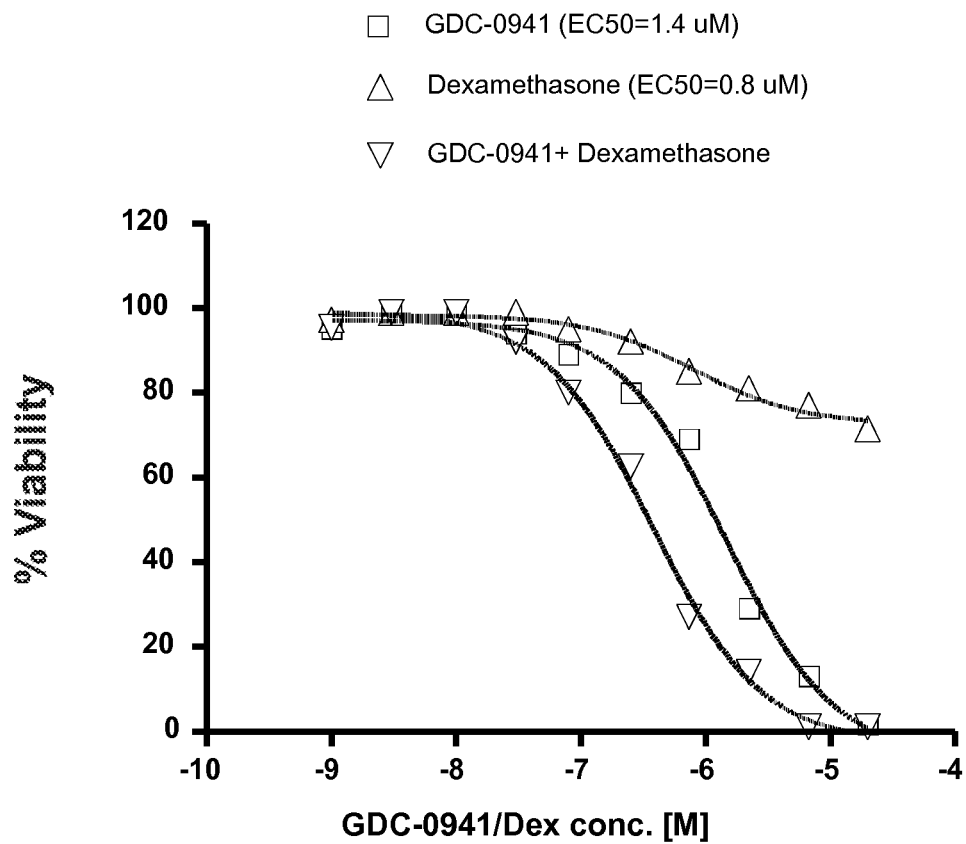
FIG. 6 shows the effect of PI3K single agent inhibitor Formula Ia (GDC-0941), and in combination with dexamethasone, on multiple myeloma OPM2 cells by in vitro cell survival and proliferation assays (Cell-Titer Glo®) measuring viable cells over varying concentrations ($10^{-5}$ to 10 µMolar) of Formula Ia, dexamethasone, and the combination of Formula Ia and dexamethasone.

The individual measured EC50 values of the Formula I compounds and of the chemotherapeutic agent against the particular cell are compared to the combination EC50 value. The combination index (CI) score is calculated by the Chou and Talalay method (Chou, T. and Talalay, P. (1984) Adv. Enzyme Regul. 22:27-55). A CI less than 0.8 indicates synergy. A CI between 0.8 and 1.2 indicates additivity. A CI greater than 1.2 indicates antagonism. The strength of synergy is assessed according to Chou and Talalay. Certain therapeutic combinations in FIGS. 4-6 show the surprising and unexpected property of synergy in the in vitro cell proliferation assays with tumor type cell lines including non-Hodgkin's lymphoma (NHL), diffuse large B-cell lymphoma (DLBCL), and multiple myeloma. Other combinations show no synergy; and only show mere additivity or antagonism. Certain combinations are synergistic with one or more tumor types, but not others. The synergy demonstrated in the in vitro cell proliferation assays provides a basis to expect a corresponding synergy in treating hematopoietic cancers including, but not limited to, lymphoma and multiple myeloma in human patients.

Figure 3:
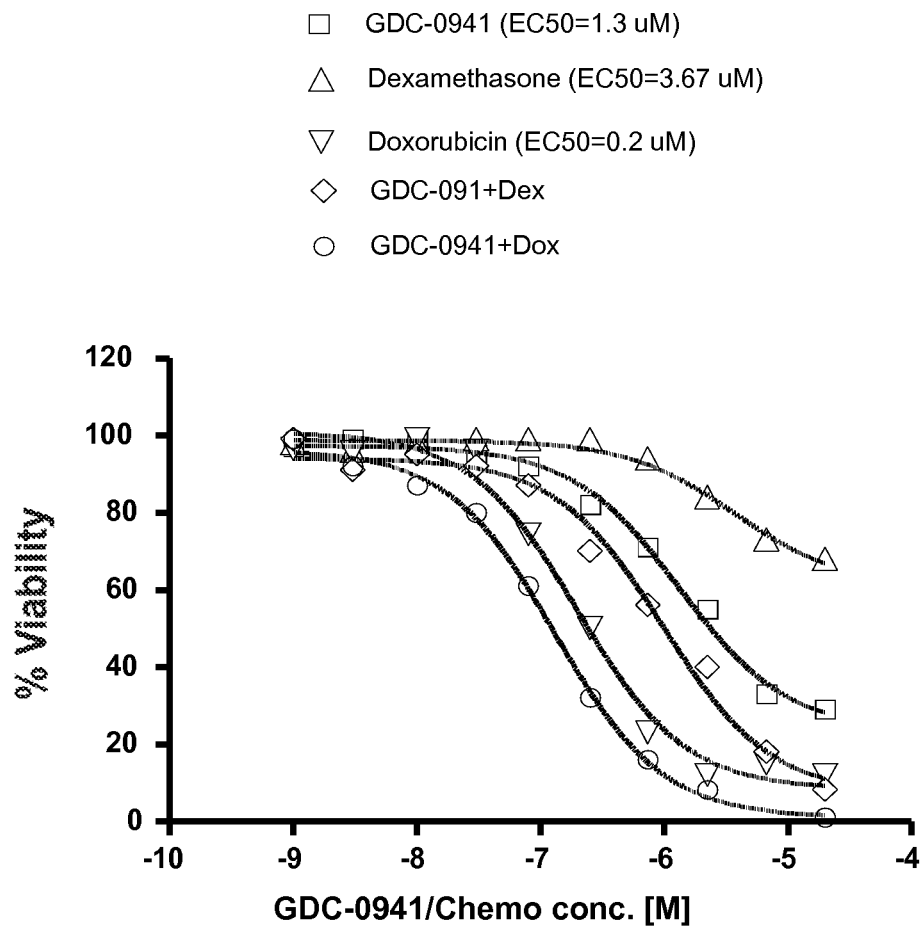
FIG. 3 shows the effect of PI3K single agent inhibitor, Formula Ia (GDC-0941), and in combinations with dexamethasone (Dex) and doxorubicin (Dox), on B-NHL cell line DoHH2. In vitro cell survival and proliferation assays (Cell-Titer Glo, Promega) measured viable cells over varying inhibitor concentrations ($10^{-5}$ to 10 Relative Units of the previously (approximately) determined IC50, Formula Ia, dexamethasone, doxorubicin and combinations of Formula Ia and dexamethasone; and Formula Ia and doxorubicin.

FIG. 3 shows the effect of PI3K single agent inhibitor, Formula Ia (GDC-0941), and in combinations with dexamethasone (Dex) and doxorubicin (Dox), on B-NHL cell line DoHH2. In vitro cell survival and proliferation assays (CellTiter Glo, Promega) measured viable cells over varying inhibitor concentrations ($10^{-5}$ to 10 Relative Units of the previously (approximately) determined IC50, Formula Ia, dexamethasone, doxorubicin and combinations of Formula Ia and dexamethasone; and Formula Ia and doxorubicin. Note that the extent of cell killing at the highest concentration of inhibitors varied from one agent to another. In the case of Doxorubicin, the addition of GDC-0941 caused a modest shift of the dose-response curve to the left, indicating an increased sensitivity of cells to the combination treatment. A combination index (CI) of ~0.75 was calculated for this combination, indicating additivity or synergy. The relatively impotent activity of dexamethasone single agent is reflected as a higher IC50 value as well as weaker extend of signal reduction in the assay, perhaps pointing to a cytostatic effect or only weak cytotoxic activity. In combination with GDC-0941 however, a surprising and highly significant leftward shift of the dose-response curve was obtained at all concentrations. The calculated CI value at the IC50 point was ~0.3, indicating an unpredicted and unexpectedly strong synergy rarely seen between test agents.

Formula Ia (GDC-0941) is cytotoxic to many B lymphoma cell lines, inducing robust apoptosis as a single agent, according to Table 2.

TABLE 2

| Cell Lines | Tumor type | EC50 (µM) |
|---|---|---|
| SUDHL6 | DLBCL | 0.01 |
| RI1 | B-NHL | 0.04 |
| SUDHL5 | DLBCL | 0.08 |
| WSUDLCL2 | DLBCL | 0.13 |
| MC116 | NHL | 0.16 |
| WSUNHL | NHL | 0.16 |
| Rec1 | B-NHL | 0.16 |
| Granta519 | MCL | 0.21 |
| Farage | DLBCL | 0.24 |
| DoHH2 | DLBCL/FLL | 0.26 |
| OciLy19 | DLBCL | 0.32 |
| Jeko1 | MCL | 0.32 |
| Bjab | Burkit's | 0.33 |
| SUDHL4 | DLBCL | 1.35 |
| HT | DLBCL | 2.84 |
| DB | DLBCL | 10 |
| Ramos | Burkit's | 10 |
| SC1 | DLBCL | 10 |
| Toledo | DLBCL | 10 |

Data in table 2 indicate that GDC-0941 is broadly cytotoxic and potent against lymphoma cell lines at doses that could be clinically attainable.

Experiments such as those in FIG. 2 were extended to additional cell lines and for combinations of GDC-0941 with thioTEPA, doxorubicin, vincristine, and dexamethasone. Combination Index (CI) scores were calculated by the Chou-Talalay method (Table 3). In no case did we find that CI values >1 which would indicate that GDC-0941 antagonized these other agents when tested in combination. In general, GDC-0941 combine well with these other agents showing at least additivity. For combinations with Dexamethasone, surprising and highly significant CI values of approximately 0.3 or less were obtained in all cell lines tested.

TABLE 3

| | B-NHL Cell Lines | | | | |
|---|---|---|---|---|---|
| | EC50 (µM) GDC-0941 (single agent) | CI at EC50 thioTEPA | CI at EC50 Dox | CI at EC50 vincristine | CI at EC50 Dex |
| Bjab | 0.33 | 0.88 | 0.64 | 0.83 | 0.30 |
| DoHH2 | 0.16 | 0.65 | 0.75 | Not determined | 0.31 |
| WSU-DLCL2 | 0.17 | 0.69 | 0.81 | Not determined | 0.12 |

FIG. 4 shows the effect of PI3K single agent inhibitors on primary follicular lymphoma cells from patient NHL600 as determined by in vitro cell survival and proliferation assays (Cell-Titer Glo®, Promega Corp., Madison, Wis.) measuring viable cells over varying concentrations ($10^{-5}$ to 10 µMolar) of Formula Ia, GDC-0464, and LY294002. As cell line cytoxicity data are commonly held to overestimate the potency of these compounds, the data indicate that Formula Ia (GDC-0941) has a surprising and unexpected degree of potency against primary human cancer cells. GDC-0464 (Genentech, Inc.) is a potent thienopyrimidine PI3K inhibitor (US 2008/0076758). LY294002 (Eli Lilly & Co., CAS Reg. No. 154447-36-6) is also a potent inhibitor of PI3 kinases (WO 2003/035099).

FIG. 5 shows the effect of a PI3K single agent inhibitor, Formula Ia (GDC-0941), and in combination with doxorubicin, on primary diffuse large B-cell lymphoma (DLBCL) cells from patient NHL640-A055. Cell viability was measured by in vitro cell survival and proliferation assays (Cell-Titer Glo0) over varying concentrations ($10^{-5}$ to 20 µMolar) of Formula Ia, doxorubicin, and the combination of Formula Ia and doxorubicin. Anthracylines are the backbone of most chemotherapeutic regimens and as such are considered highly active compounds. These results indicate that for this primary tumor sample in vitro, that GDC-0941 was significantly more potent than doxorubicin and in surprising contrast to the results obtained with cell lines in vitro, that the combination was not significantly better than single agent GDC-0941.

FIG. 6 shows the effect of PI3K single agent inhibitor Formula Ia (GDC-0941), and in combination with dexamethasone, on multiple myeloma OPM2 cells by in vitro cell proliferation assays (Cell-Titer Glo®) measuring viable cells over varying drug concentrations (expressed as a function of their previously determined IC50 values, i.e., "1"=[drug] giving an IC50 response) of Formula Ia, dexamethasone (Dex), and the combination of Formula Ia and dexamethasone at fixed ratios. The relatively weak response to dexamethasone is greatly enhanced by combination with GDC-0941, both in terms of potency as well as the extent of response, and a CI value of 0.45 is obtained indicating strong synergy between the two agents. Table 4 shows the Combination Index scores, calculated by the Chou & Talalay method, of treatment of various multiple myeloma cell lines by the therapeutic combinations of Formula Ia compound (GDC-0941) and a chemotherapeutic agent selected from dexamethasone (Dex), doxorubicin (Dox), melphalan, lenalidomide, and bortezomib. Certain combinations show synergy (CI<0.8), additivity (0.8-1.2), or antagonism (>1.2). These data indicated GDC-0941 does not combine equally well with all chemotherapies. The CI's obtained with GDC-0941 and Bortezomib were generally in the range of 0.8 and higher, whereas the CI's obtained with GDC-0941 plus dexamethasone were lower and indicated both a synergistic and more prevalent response across the cell lines tested.

TABLE 4

| | multiple myeloma cell line | | | | | |
|---|---|---|---|---|---|---|
| | EC50 (µM) GDC-0941 (single agent) | CI at EC50 Dex | CI at EC50 Dox | CI at EC50 melphalan | CI at EC50 lenalidomide | CI at EC50 bortezomib |
| EJM | 1.5 | Not determined | 0.57 | Not determined | Not determined | 0.78 |
| MM1.S | 0.22 | 0.55 | 0.68 | Not determined | 0.92 | 1.18 |
| MOLP-8 | 0.06 | 1.19 | 0.85 | 0.59 | 0.90 | Not determined |
| NCI-H929 | 0.43 | 0.45 | 1.00 | Not determined | 0.48 | Not determined |
| OPM2 | 1.23 | 0.45 | 0.99 | 2.00 | 0.47 | 0.92 |
| RPMI-8226 | 2.53 | 0.17 | 0.83 | 0.75 | 0.59 | 1.00 |
| KSM-12-BM | >5 | Not determined | 0.52 | 0.30 | Not determined | 0.68 |

TABLE 5

| Combination of GDC-0941 and vincristine | | | |
|---|---|---|---|
| cell line | CI at ED50 | CI at ED75 | CI at ED90 |
| Bjab | 0.84 | 0.63 | 0.58 |
| DoHH2 | 0.92 | 0.94 | 1.03 |
| WSU-DHL4 | 0.53 | 0.47 | 0.42 |
| WSU-DLCL2 | 0.63 | 0.60 | 0.56 |

Table 5 shows the Combination Index scores, calculated by the method of Chou and Talalay, of different lymphoma cell lines by the therapeutic combinations of Formula Ia compound GDC-0941 and the chemotherapeutic agent vincristine. Certain combinations show synergy (CI<0.8), additivity (0.8-1.2), or antagonism (>1.2). The data indicate that GDC-0941 combines quite favorably with vincristine particularly in BJAB, WSU-DHL4, and WSU-DLCL2. The CI value is shown at three different points on the dose-response curve, the ED50, ED75, and ED90 and the fact that similar CI values are obtained at these different points on the dose response curve indicates that the data are robust and the entire response curve has shifted to yield an increased biological response in the case of the combination of agents.

Table 6 shows the Combination Index scores, calculated by the Chou & Talalay method, of treatment of various hematopoietic malignancy cell lines in the presence or absence of growth factors IL6 and IGF-1 by the therapeutic combinations of Formula Ia compound (GDC-0941) and dexamethasone. Certain combinations show synergy (CI<0.8), additivity (0.8-1.2), or antagonism (>1.2). The data indicate that GDC-0941 combines quite favorably with dexamethasone. The CI value is shown at three different points on the dose-response curve, the ED50, ED75, and ED90 and the fact that similar CI values are obtained at these different points on the dose response curve indicates that the data are robust and the entire response curve has shifted to yield an increased biological response in the case of the combination of agents. MM1.s cells are known to be sensitive to dexamethasone and exhibited clear synergy when combined with GDC-0941. The MM1.r variant of this cell line is known to be dexamethasone resistant, and consistent with this property, overall lesser CI values were observed. The cytokines IL-6 and IGF-1 are major growth factors in the bone marrow microenvironment of multiple myeloma and involved in mediating signals via the PI3K/AKT signaling pathway. The growth factors IL-6 and IGF-1 are generally thought to provide chemoresistance and in each of the cell lines addition of cytokines increased the combination index values.

TABLE 6

Combination of GDC-0941 and dexamethasone

| cell line | CI at ED50 | CI at ED75 | CI at ED90 |
|---|---|---|---|
| MM1.S (no IL6 or IGF1) | 0.15 | 0.17 | 0.19 |
| MM1.S (+IL6, +IGF1) | 0.53 | 0.54 | 0.54 |
| MM1.R (no IL6 or IGF1) | 0.77 | 1.01 | 1.34 |
| MM1.R (+IL6, +IGF1) | 0.85 | 0.92 | 1.00 |
| OPM2 (no IL6 or IGF1) | 0.46 | 0.37 | 0.30 |
| OPM2 (+IL6, +IGF1) | 0.93 | 1.10 | 1.30 |
| NCIH929 (no IL6 or IGF1) | 0.48 | 0.41 | 0.35 |
| NCIH929 (+IL6, +IGF1) | 1.08 | 1.39 | 1.80 |
| KMS-11 (no IL6 or IGF1) | 0.14 | 0.10 | 0.08 |
| KMS-11 (+IL6, +IGF1) | 0.31 | 0.27 | 0.23 |
| RPMI-8826 (no IL6 or IGF1) | 0.45 | 0.47 | 0.49 |
| RPMI-8826 (+IL6, +IGF1) | 0.19 | 0.09 | 0.04 |
| U266 (no IL6 or IGF1) | 1.45 | 4.74 | 15 |
| U266 (+IL6, +IGF1) | no calc | no calc | no calc |

Table 7 shows the Combination Index scores, calculated by the Chou & Talalay method, of treatment of various hematopoietic malignancy cell lines in the presence or absence of growth factors IL6 and IGF-1 by the therapeutic combinations of Formula Ia compound (GDC-0941) and lenalidomide. Certain combinations show synergy (CI<0.8), additivity (0.8-1.2), or antagonism (>1.2). The data indicate that GDC-0941 combines quite favorably with lenalidomide. The CI value is shown at three different points on the dose-response curve, the ED50, ED75, and ED90 and for certain cell lines, the fact that similar CI values are obtained at these different points on the dose response curve indicates that the data are robust and the entire response curve has shifted to yield an increased biological response in the case of the combination of agents. The growth factors IL-6 and IGF-1 are generally thought to provide chemoresistance and in each of the cell lines addition of cytokines increased the combination index values.

TABLE 7

Combination of GDC-0941 and lenalidomide

| cell line | CI at ED50 | CI at ED75 | CI at ED90 |
|---|---|---|---|
| MM1.S (no IL6 or IGF1) | 0.37 | 0.89 | 2.14 |
| MM1.S (+IL6, + IGF1) | 1.01 | 1.06 | 1.11 |
| MM1.R (no IL6 or IGF1) | 0.61 | 0.74 | 0.91 |
| MM1.R (+IL6, +IGF1) | 0.85 | 0.92 | 1.00 |
| OPM2 (no IL6 or IGF1) | 0.59 | 0.60 | 0.60 |
| OPM2 (+IL6, +IGF1) | 0.70 | 0.78 | 0.86 |
| NCIH929 (no IL6 or IGF1) | 0.54 | 0.63 | 0.74 |
| NCIH929 (+IL6, +IGF1) | 0.79 | 0.95 | 1.13 |
| KMS-11 (no IL6 or IGF1) | 0.53 | 0.72 | 0.96 |
| KMS-11 (+IL6, +IGF1) | 0.89 | 0.96 | 1.04 |
| RPMI-8826 (no IL6 or IGF1) | 0.45 | 0.64 | 0.91 |
| RPMI-8826 (+IL6, +IGF1) | 1.86 | 2.13 | 2.45 |

Apoptotic responses to single agents Figure Ia and Ib compounds, and the combinations of: (i) Figure Ia compound (GDC-0941) and rapamycin, and (ii) Figure Ib compound and rapamycin in multiple myeloma and AML cell lines, including OPM2 and H929, were measured by Annexin V-FACS analysis. The screening conditions to measure absolute IC50s comprised: Day1—Plate cells at 10,000 cells/well on a 384-well plate in media with 10% FBS; Day2—Dose cells with indicated compound setup. When rapamycin was used in combination with Figure Ia or Figure Ib compounds, rapamycin concentration in the media was 0.1 uM; and Day5—Celltiter-Glo assay. The measured apoptotic populations demonstrated synergy with combinations (i) and (ii).

In blast cells from AML patients, the combination of Figure Ia GDC-0941 and a chemotherapy agent cytarabine or daunorubicin showed enhanced anti-leukemic activity compared to single agent GDC-0941, and enhanced apoptic efficacy with only 30% and 22% live cells remaining, respectively.

In Vivo Tumor Xenograft Efficacy

The efficacy of the combinations of the invention may be measured in vivo by implanting allografts or xenografts of cancer cells in rodents and treating the tumor-bearing animals with the combinations. Variable results are to be expected depending on the cell line, the presence or absence of certain mutations in the tumor cells, the sequence of administration of Formula I compound and chemotherapeutic agent, dosing regimen, and other factors. Subject mice were treated with drug(s) or control (Vehicle) and monitored over several weeks or more to measure the time to tumor doubling, log cell kill, and tumor inhibition (Example 16).

Figure 7:
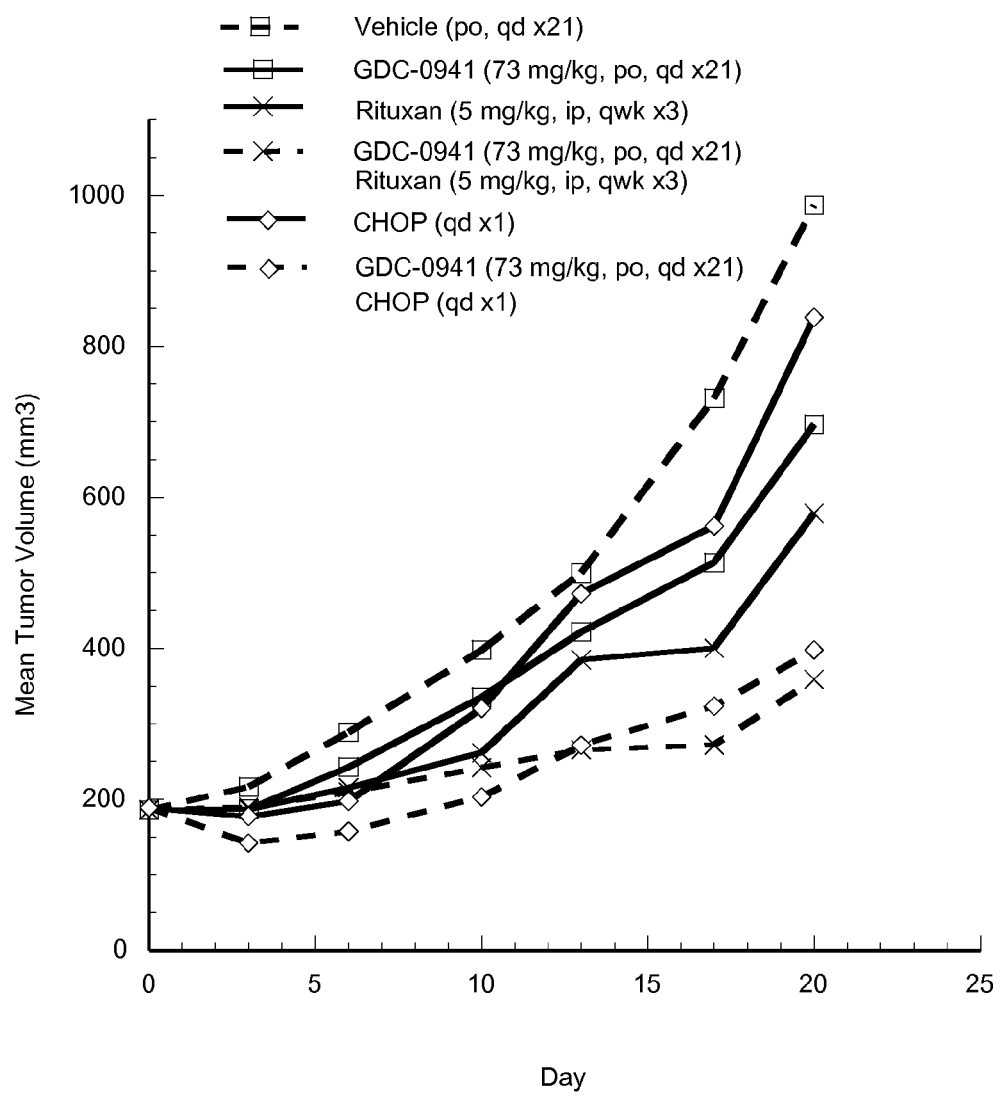
FIG. 7 shows the mean tumor volume change over 20 days in cohorts of 10 mice with WSU-DLCL2 lymphoma tumor xenografts dosed on day 0 with Vehicle (0.5% Methylcellulose: 0.2% Tween 80 in DI Water), 73 mg/kg Formula Ia (GDC-0941), 5 mg/kg rituximab, CHOP, and the combinations of Formula Ia 73 mg/kg and rituximab 5 mg/kg, Formula Ia 73 mg/kg and CHOP. Mice were dosed once with CHOP starting on day 0, and rituximab on days 0, 7, and 14, while Formula Ia was dosed daily for 21 days by oral gavage. CHOP regimen: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5). Cyclophosphamide, doxorubicin and vincristine were dosed once on day 0 and prednisone was dosed on days 0, 1, 2, 3 and 4.

FIG. 7 shows the mean tumor volume change over 20 days in cohorts of 10 mice with WSU-DLCL2 lymphoma tumor xenografts dosed on day 0 with Vehicle (0.5% Methylcellulose: 0.2% Tween 80 in DI Water), 73 mg/kg Formula Ia (GDC-0941), 5 mg/kg rituximab, CHOP, and the combinations of Formula Ia 73 mg/kg and rituximab 5 mg/kg, Formula Ia 73 mg/kg and CHOP. Mice were dosed with CHOP starting on day 0, and rituximab on days 0, 7, and 14, while Formula Ia was dosed daily for 21 days by oral gavage. CHOP regimen: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5). Cyclophosphamide, doxorubicin and vincristine were dosed once on day 0 and prednisone was dosed on days 0, 1, 2, 3 and 4. In this model, GDC-0941, and CHOP-based combination chemotherapy had only modest activity. Rituximab treatment was significantly more different from vehicle (p<0.01 by Control Dunnett's t-test). The combination of GDC-0941 with rituximab was significantly better than GDC-0941, but not different from rituximab alone by log-rank analysis. The combination of GDC-0941 and CHOP gave a significant improvement in efficacy compared to either agent alone.

Figure 8:
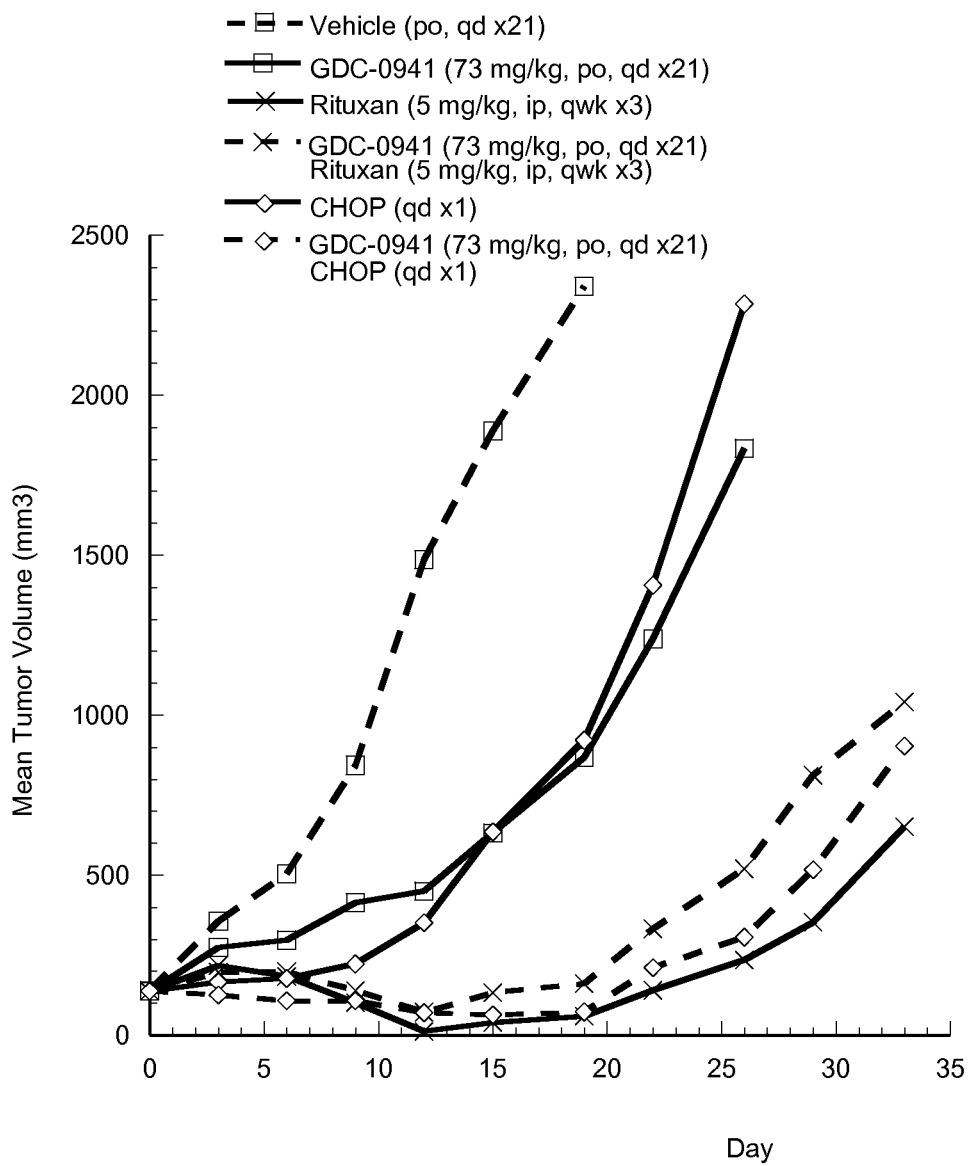
FIG. 8 shows the mean tumor volume change over 35 days in cohorts of 10 mice with DoHH-2 lymphoma tumor xenografts dosed on day 0 with: Vehicle (0.5% methylcellulose: 0.2% Tween 80 in DI Water), 73 mg/kg Formula Ia (GDC-0941), 5 mg/kg rituximab, CHOP, and the combinations of Formula Ia 73 mg/kg and rituximab 5 mg/kg, and Formula Ia 73 mg/kg and CHOP. Mice were dosed with rituximab on day 0, 7 and 14 (qwk×3) intravenously, CHOP starting on day 1, while Formula Ia was dosed daily for 21 days by oral gavage. CHOP regimen: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5). Cyclophosphamide, doxorubicin and vincristine were dosed once on day 0 and prednisone was dosed on days 0, 1, 2, 3 and 4.

FIG. 8 shows the mean tumor volume change over 34 days in cohorts of 10 mice with DoHH-2 tumor xenografts dosed on day 0 with: Vehicle (0.5% methylcellulose: 0.2% Tween 80 in DI Water), 73 mg/kg Formula Ia (GDC-0941), 5 mg/kg rituximab, CHOP, and the combinations of Formula Ia 73 mg/kg and rituximab 5 mg/kg, and Formula Ia 100 mg/kg and CHOP. Mice were dosed with rituximab on day 0, 7 and 14 (qwk×3) intravenously, CHOP starting on day 1, while Formula Ia was dosed daily for 21 days by oral gavage. CHOP regimen: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5). Cyclophosphamide, doxorubicin and vincristine were dosed once on day 0 and prednisone was dosed on days 0, 1, 2, 3 and 4. CHOP chemotherapy or GDC-0941 monotherapy cohorts were significantly different than vehicle. Rituximab monotherapy was relatively more effective causing 2 partial responses and 4 complete responses during treatment. GDC-0941 did not significantly antagonize rituximab activity, however, it did not provide additional antitumor activity. In contrast, the combination of GDC-0941 with CHOP chemotherapy gave a very significant increase in benefit over the activity of either single agent and produced 2 partial responses and 2 complete responses.

Figure 9:
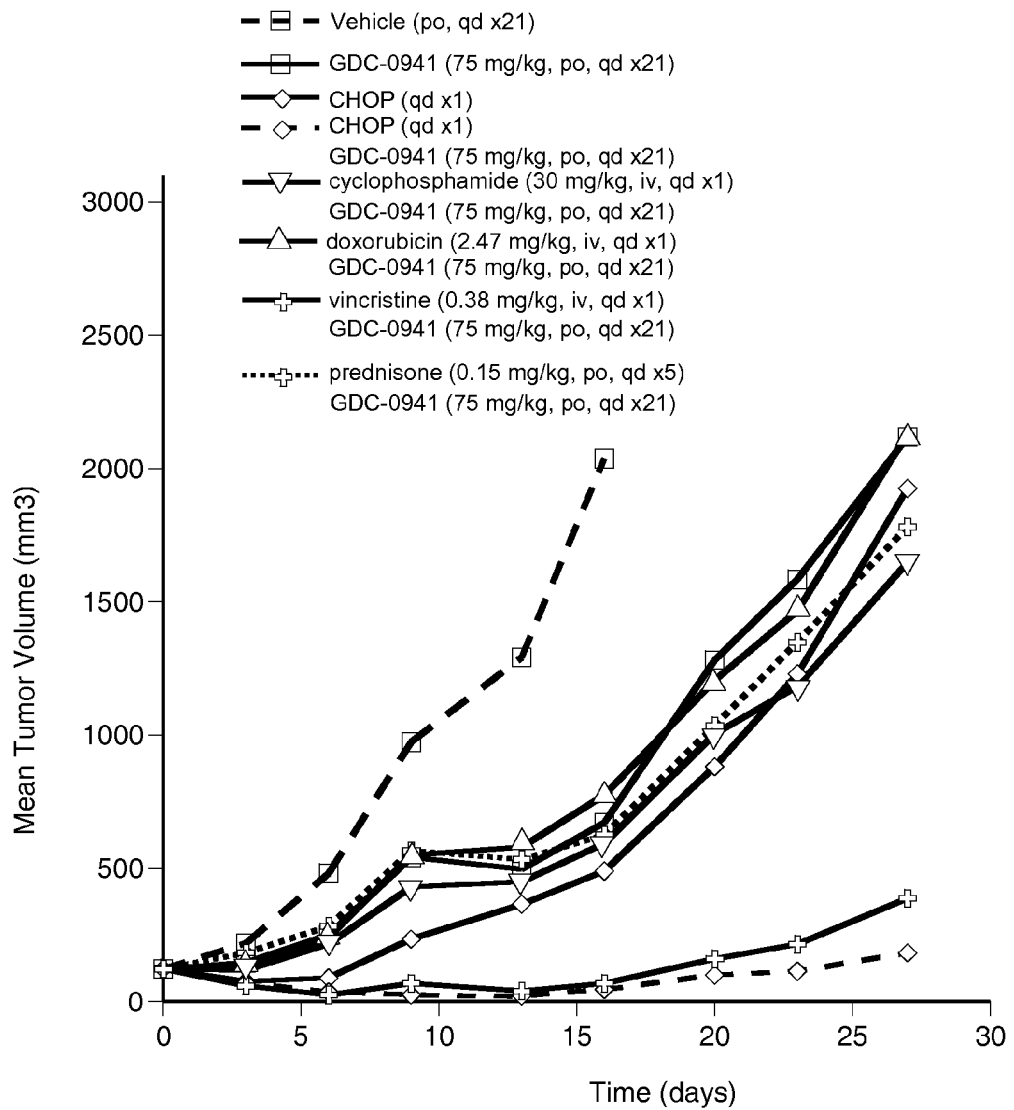
FIG. 9 shows the mean tumor volume change over 27 days in cohorts of 10 mice with DoHH2 lymphoma tumor xenografts dosed on day 0 with: Vehicle (0.5% Methylcellulose: 0.2% Tween 80 in DI Water), 75 mg/kg Formula Ia (GDC-0941), CHOP, and the combinations of Formula Ia 75 mg/kg and CHOP, Formula Ia 75 mg/kg and cyclophosphamide 30 mg/kg, Formula Ia 75 mg/kg and doxorubicin 2.47 mg/kg, Formula Ia 75 mg/kg and vincristine 0.38 mg/kg, and Formula Ia 75 mg/kg and prednisone 0.15 mg/kg. Mice were dosed with CHOP on day 0, cyclophosphamide on day 0, doxorubicin on day 0, vincristine on day 0, and prednisone daily on days 0-4, while Formula Ia was dosed daily for 21 days by oral gavage. CHOP components regimen was: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5)

FIG. 9 shows the mean tumor volume change over 27 days in cohorts of 10 mice with DoHH2 tumor xenografts dosed on day 0 with: Vehicle (0.5% methylcellulose: 0.2% Tween 80 in DI Water), 75 mg/kg Formula Ia (GDC-0941), CHOP, and the combinations of Formula Ia 75 mg/kg and CHOP, Formula Ia 75 mg/kg and cyclophosphamide 30 mg/kg, Formula Ia 75 mg/kg and doxorubicin 2.47 mg/kg, Formula Ia 75 mg/kg and vincristine 0.38 mg/kg, and Formula Ia 75 mg/kg and prednisone 0.15 mg/kg. Mice were dosed with CHOP on day 0, cyclophosphamide on day 0, doxorubicin on day 0, vincristine on day 0, and prednisone daily on days 0-4, while Formula Ia was dosed daily for 21 days by oral gavage. CHOP components regimen was: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5). This experiment confirms and extends the results of FIG. 8 to show that GDC-0941 and CHOP each have similar and only moderate activity in the model. As before, GDC-0941 combines with CHOP to give a very significant increase in antitumor activity. Surprisingly, as this was not predicted from in vitro experiments, essentially all of the synergy noted between GDC-0941 and CHOP can be attributed to the combination of just GDC-0941 and vincristine, whereas the other three components of CHOP tested pairwise with GDC-0941 did not exhibit increased efficacy.

Figure 10:
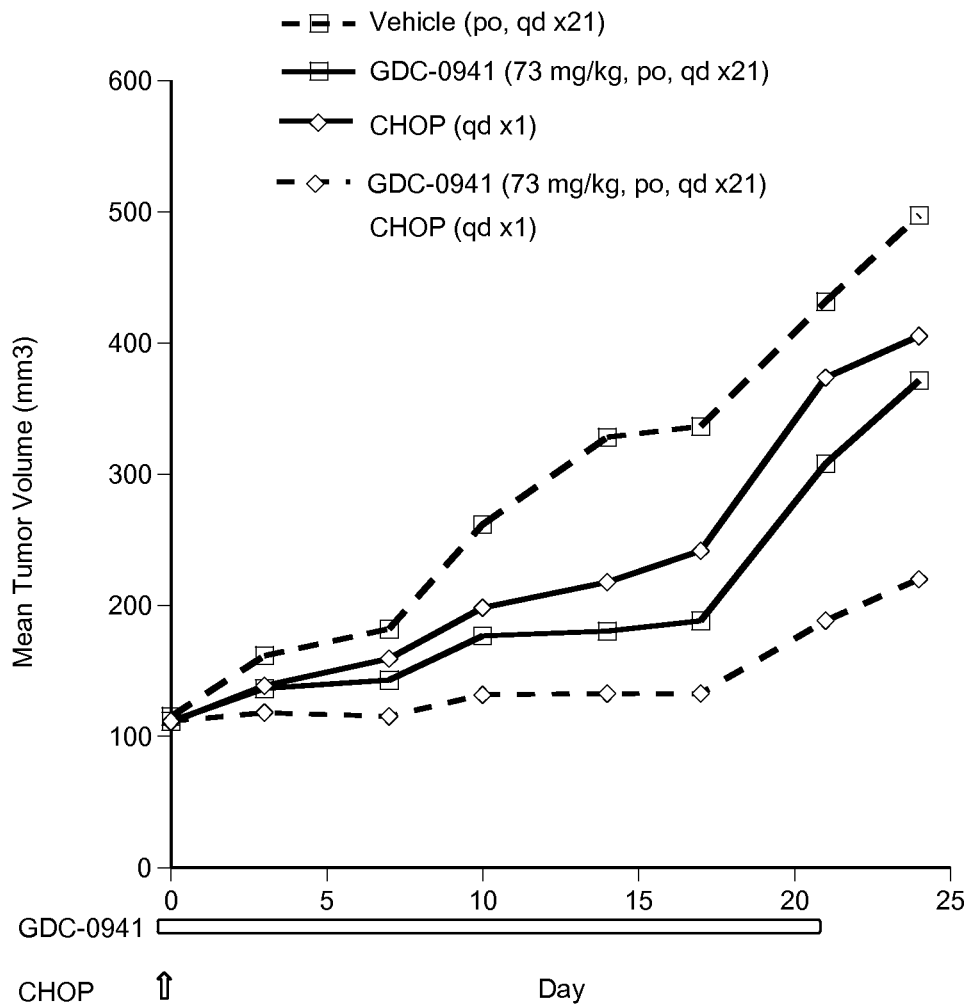
FIG. 10 shows the mean tumor volume change over 25 days in cohorts of 10 mice with BJAB lymphoma tumor xenografts dosed on day 0 with: Vehicle (0.5% Methylcellulose: 0.2% Tween 80 in DI Water), 73 mg/kg Formula Ia (GDC-0941), CHOP, and the combination of Formula Ia 73 mg/kg and CHOP. Mice were dosed once with CHOP starting on day 0, while Formula Ia and Vehicle were dosed daily for 21 days by oral gavage. CHOP regimen: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5). Cyclophosphamide, doxorubicin and vincristine were dosed once on day 0 and prednisone was dosed on days 0, 1, 2, 3 and 4.

FIG. 10 shows the mean tumor volume change over 25 days in cohorts of 10 mice with BJAB lymphoma tumor xenografts dosed on day 0 with: Vehicle (0.5% Methylcellulose: 0.2% Tween 80 in DI Water), 73 mg/kg Formula Ia (GDC-0941), CHOP, and the combination of Formula Ia 73 mg/kg and CHOP. Mice were dosed once with CHOP starting on day 0, while Formula Ia and Vehicle were dosed daily for 21 days by oral gavage. CHOP regimen: cyclophosphamide (30 mg/kg, iv, qd×1), doxorubicin (2.475 mg/kg, iv, qd×1), vincristine (0.375 mg/kg, iv, qd×1), prednisone (0.15 mg/kg, po, qd×5). Cyclophosphamide, doxorubicin and vincristine were dosed once on day 0 and prednisone was dosed on days 0, 1, 2, 3 and 4. These data show in the BJAB lymphoma model that GDC-0941 or CHOP chemotherapy have only modest activity and that the combination has increased activity although no groups reach statistical significance.

Figure 11:
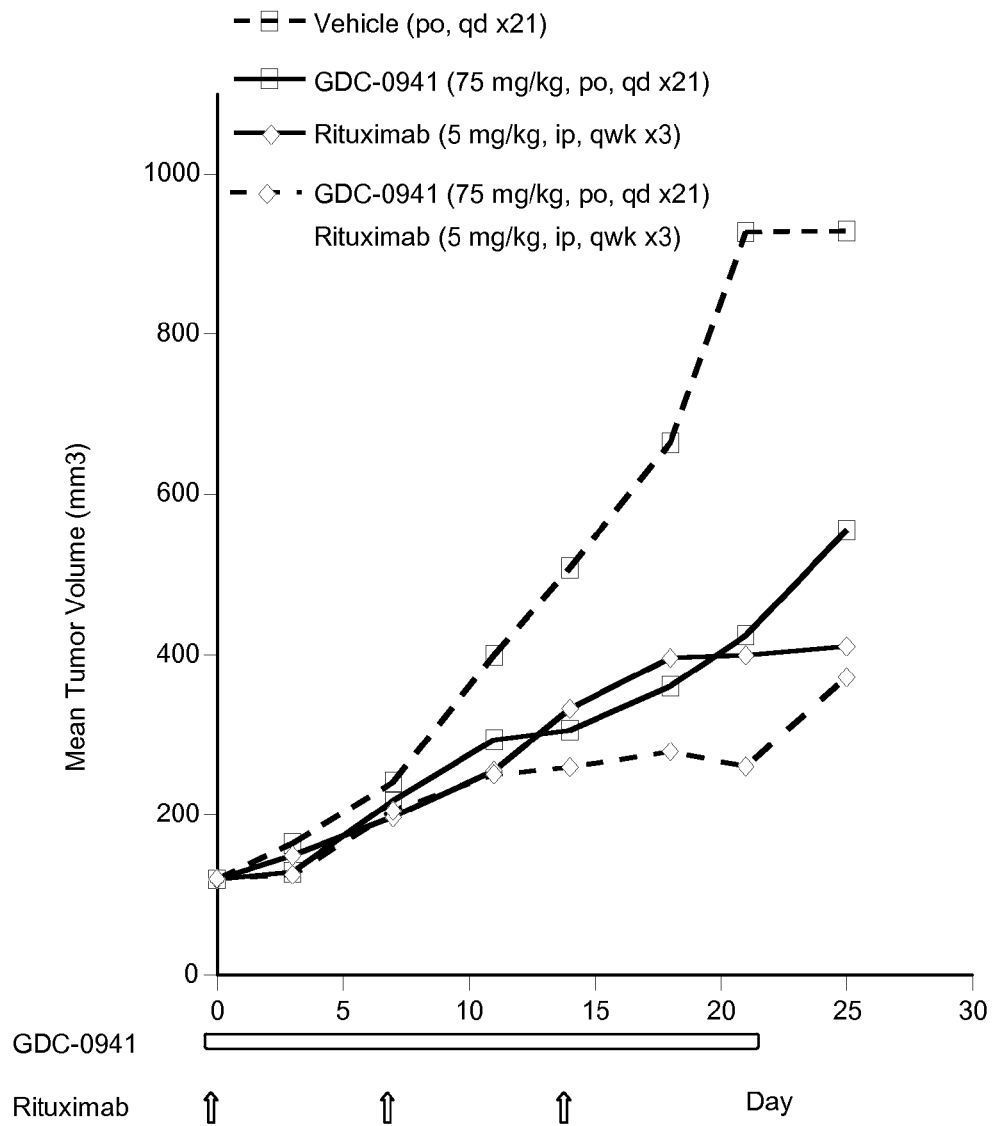
FIG. 11 shows the mean tumor volume change over 25 days in cohorts of 10 mice with BJAB lymphoma tumor xenografts dosed on day 0 with: Vehicle (0.5% Methylcellulose: 0.2% Tween 80 in DI Water), 75 mg/kg Formula Ia (GDC-0941), 5 mg/kg rituximab, and the combination of Formula Ia 75 mg/kg and 5 mg/kg rituximab. Mice were dosed with rituximab on days 0, 7, and 14, while Formula Ia and Vehicle were dosed daily for 21 days (po, qd×21) by oral gavage.

FIG. 11 shows the mean tumor volume change over 25 days in cohorts of 10 mice with BJAB lymphoma tumor xenografts dosed on day 0 with: Vehicle (0.5% Methylcellulose: 0.2% Tween 80 in DI Water), 75 mg/kg Formula Ia (GDC-0941), 5 mg/kg rituximab, and the combination of Formula Ia 75 mg/kg and 5 mg/kg rituximab. Mice were dosed with rituximab on days 0, 7, and 14, while Formula Ia and Vehicle were dosed daily for 21 days (po, qd×21) by oral gavage. As in FIG. 10, single agent GDC-0941 had only modest activity in this BJAB lymphoma model. The activity of rituximab was modest compared to single agent GDC-0941 and was not further increased by combination with GDC-0941. In this study all groups are significantly different than vehicle by log-rank analysis.

Figure 12:
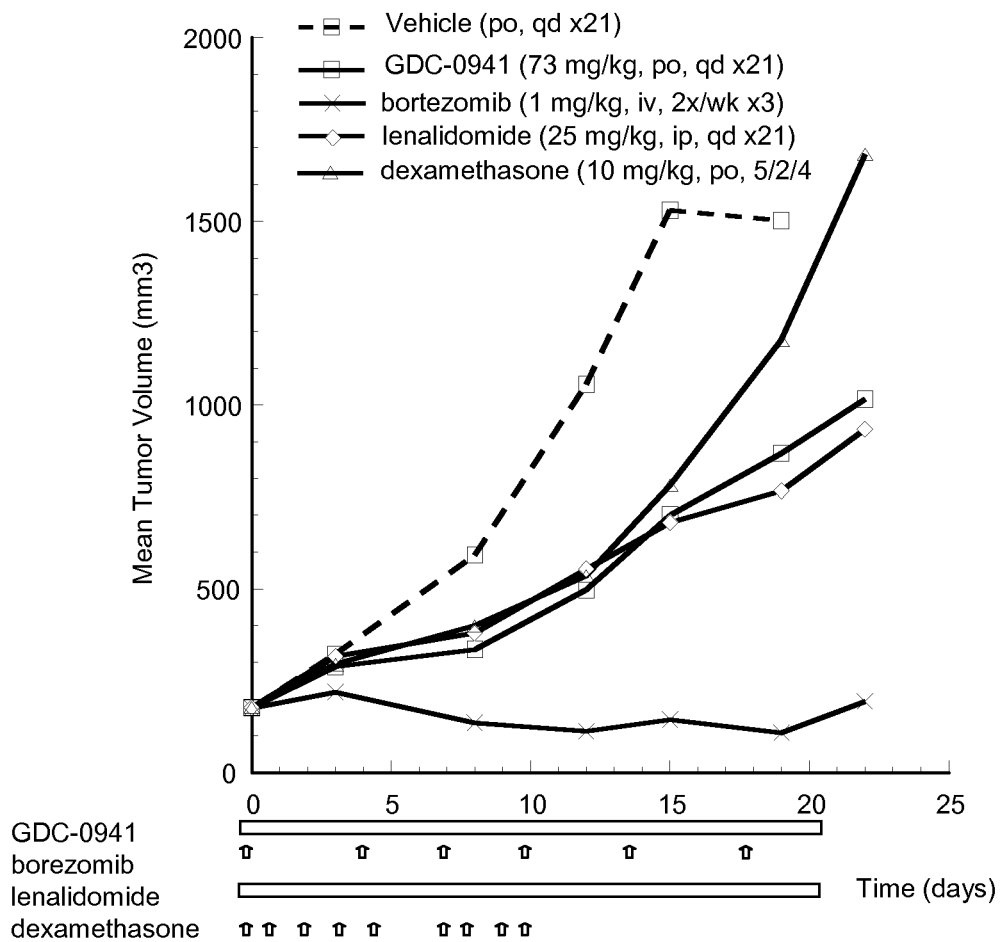
FIG. 12 shows the mean tumor volume change over 22 days in cohorts of 10 mice with NCI-H929 multiple myeloma xenografts dosed on day 0 with: Vehicle (po, qd×21) (0.5% Methylcellulose: 0.2% Tween 80 in DI Water), and single agent therapies: 73 mg/kg Formula Ia GDC-0941, 1 mg/kg bortezomib, 25 mg/kg lenalidomide, and 10 mg/kg dexamethasone. Formula Ia GDC-0941 was dosed daily for 21 days by oral gavage. Bortezomib was dosed intravenously on days 0, 3, 7, 10, 14 and 17. Lenalidomide was dosed daily for 21 days by intraperitoneal injection. Dexamethasone was dosed orally on days 0, 1, 2, 3, 4, 7, 8, 9 and 10.

FIG. 12 shows the mean tumor volume change over 22 days in cohorts of 10 mice with NCI-H929 multiple myeloma xenografts dosed on day 0 with: Vehicle (po, qd×21) (0.5% Methylcellulose: 0.2% Tween 80 in DI Water), and single agent therapies: 73 mg/kg Formula Ia GDC-0941 (po, qd×21), 1 mg/kg bortezomib (iv, 2×/wk×3), 25 mg/kg lenalidomide (ip, qd×21), and 10 mg/kg dexamethasone (po, 5 days on/2 days off/4 days on). Formula Ia GDC-0941 was dosed daily for 21 days by oral gavage. Bortezomib was dosed intravenously on days 0, 3, 7, 10, 14 and 17. Lenalidomide was dosed on daily for 21 days by intraperitoneal injection. Dexamethasone was dosed orally on days 0-4 and 7-10. This experiment established the single agent activity of GDC-0941 as similar to that of lenalidomide or dexamethasone single agent treatments, which were exceeded by the efficacy of bortezomib. Bortezomib single agent treatment resulted in 3 partial responses in this study.

Figure 13:
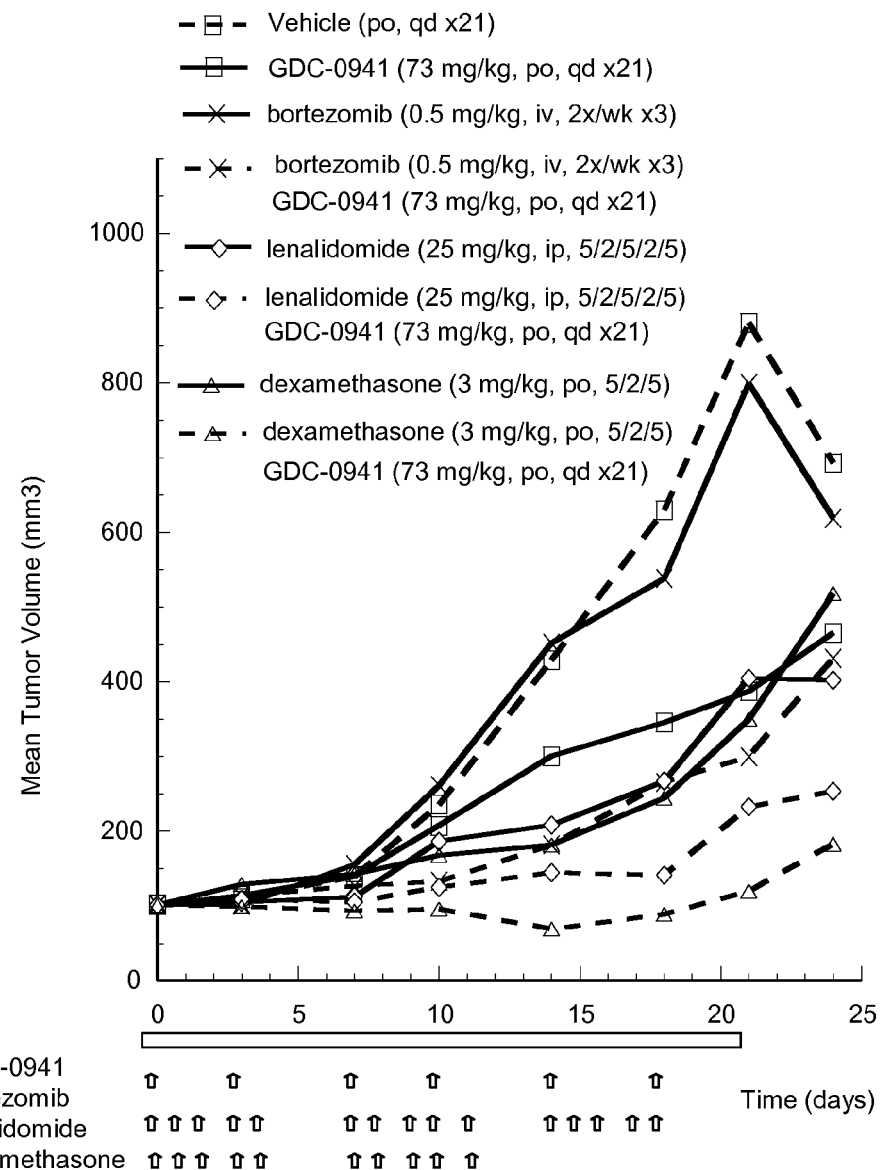
FIG. 13 shows the mean tumor volume change over 24 days in cohorts of 10 mice with multiple myeloma OPM-2 cell xenografts dosed on day 0 with: Vehicle (po, qd×21) (0.5% Methylcellulose: 0.2% Tween 80 in DI Water), single agent therapies: 73 mg/kg Formula Ia GDC-0941 (po, qd×21); 0.5 mg/kg bortezomib (iv, 2×/wk×3); 25 mg/kg lenalidomide (ip, 5 days on/2 days off/5 days on/2 days off/5 days on); and 3 mg/kg dexamethasone (po, 5 days on/2 days off/5 days on); and combinations of: 73 mg/kg Formula Ia GDC-0941 (po, qd×21) and 0.5 mg/kg bortezomib (iv, 2×/wk×3); 73 mg/kg Formula Ia GDC-0941 (po, qd×21) and 25 mg/kg lenalidomide (ip, 5/2/5/2/5); and 73 mg/kg Formula Ia GDC-0941 (po, qd×21) and 3 mg/kg dexamethasone (po, 5/2/5). Formula Ia GDC-0941 was dosed daily for 21 days by oral gavage. Bortezomib was dosed intravenously on days 0, 3, 7, 10, 14 and 17. Lenalidomide was dosed on days 0-4, 7-11 and 14-18 by intraperitoneal injection. Dexamethasone was dosed orally on days 0-4 and 7-11.

FIG. 13 shows the mean tumor volume change over 24 days in cohorts of 10 mice with multiple myeloma OPM-2 cell xenografts dosed on day 0 with: Vehicle (po, qd×21) (0.5% Methylcellulose: 0.2% Tween 80 in DI Water), single agent therapies: 73 mg/kg Formula Ia GDC-0941 (po, qd×21); 0.5 mg/kg bortezomib (iv, 2×/wk×3); 25 mg/kg lenalidomide (ip, 5 days on/2 days off/5 days on/2 days off/5 days on); and 3 mg/kg dexamethasone (po, 5 days on/2 days off/5 days on); and combinations of: 73 mg/kg Formula Ia GDC-0941 (po, qd×21) and 0.5 mg/kg bortezomib (iv, 2×/wk×3); 73 mg/kg Formula Ia GDC-0941 (po, qd×21) and 25 mg/kg lenalidomide (ip, 5/2/5/2/5); and 73 mg/kg Formula Ia GDC-0941 (po, qd×21) and 3 mg/kg dexamethasone (po, 5/2/5). Formula Ia GDC-0941 was dosed daily for 21 days by oral gavage. Bortezomib was dosed intravenously on days 0, 3, 7, 10, 14 and 17. Lenalidomide was dosed on days 0-4, 7-11 and 14-18 by intraperitoneal injection. Dexamethasone was dosed orally on days 0-4 and 7-11. A reduced dose of bortezomib in this experiment resulted in a sub-clinical response which was not different than that of vehicle. Cohorts treated with single agent GDC-0941, lenalidomide, or dexamethasone had an indistinguishable and moderate tumor activity, though the addition of GDC-0941 to dexamethasone trended towards increased antitumor activity. This result was predicted from the preceding in vitro cell line studies but not predictable from prior studies published in the literature.

Figure 14:
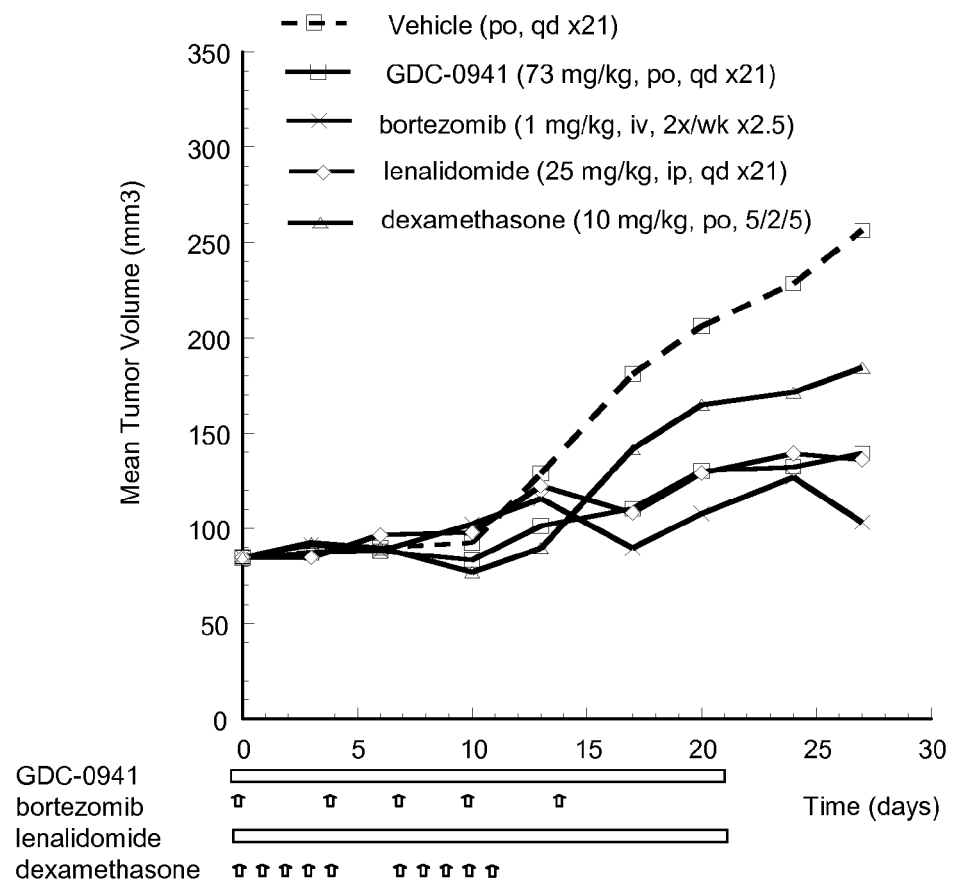
FIG. 14 shows the mean tumor volume change over 27 days in cohorts of 10 mice with multiple myeloma MM1.s cell xenografts dosed on day 0 with: Vehicle (po, qd×21) (0.5% Methylcellulose: 0.2% Tween 80 in DI Water), 73 mg/kg Formula Ia GDC-0941 (po, qd×21), 1 mg/kg bortezomib (iv, 2×/wk×2.5), 25 mg/kg lenalidomide (ip, qd×21), and 10 mg/kg dexamethasone (po, 5 days on/2 days off/5 days on). Formula Ia GDC-0941 was dosed daily for 21 days by oral gavage. Bortezomib was dosed intravenously on days 0, 3, 7, 10 and 14. Lenalidomide was dosed daily for 21 days by intraperitoneal injection. Dexamethasone was dosed orally on days 0-4 and 7-11.

FIG. 14 shows the mean tumor volume change over 27 days in cohorts of 10 mice with multiple myeloma MM1.s cell xenografts dosed on day 0 with: Vehicle (po, qd×21) (0.5% Methylcellulose: 0.2% Tween 80 in DI Water), 73 mg/kg Formula Ia GDC-0941 (po, qd×21), 1 mg/kg bortezomib (iv, 2×/wk×2.5), 25 mg/kg lenalidomide (ip, qd×21), and 10 mg/kg dexamethasone (po, 5 days on/2 days off/5 days on). Formula Ia GDC-0941 was dosed daily for 21 days by oral gavage. Bortezomib was dosed intravenously on days 0, 3, 7, and 14. Lenalidomide was dosed on daily for 21 days by intraperitoneal injection. Dexamethasone was dosed orally on days 0-4 and 7-11. This experiment established the single agent activity of GDC-0941 as similar to that of lenalidomide, bortezomib, or dexamethasone single agent treatments.

Figure 15:
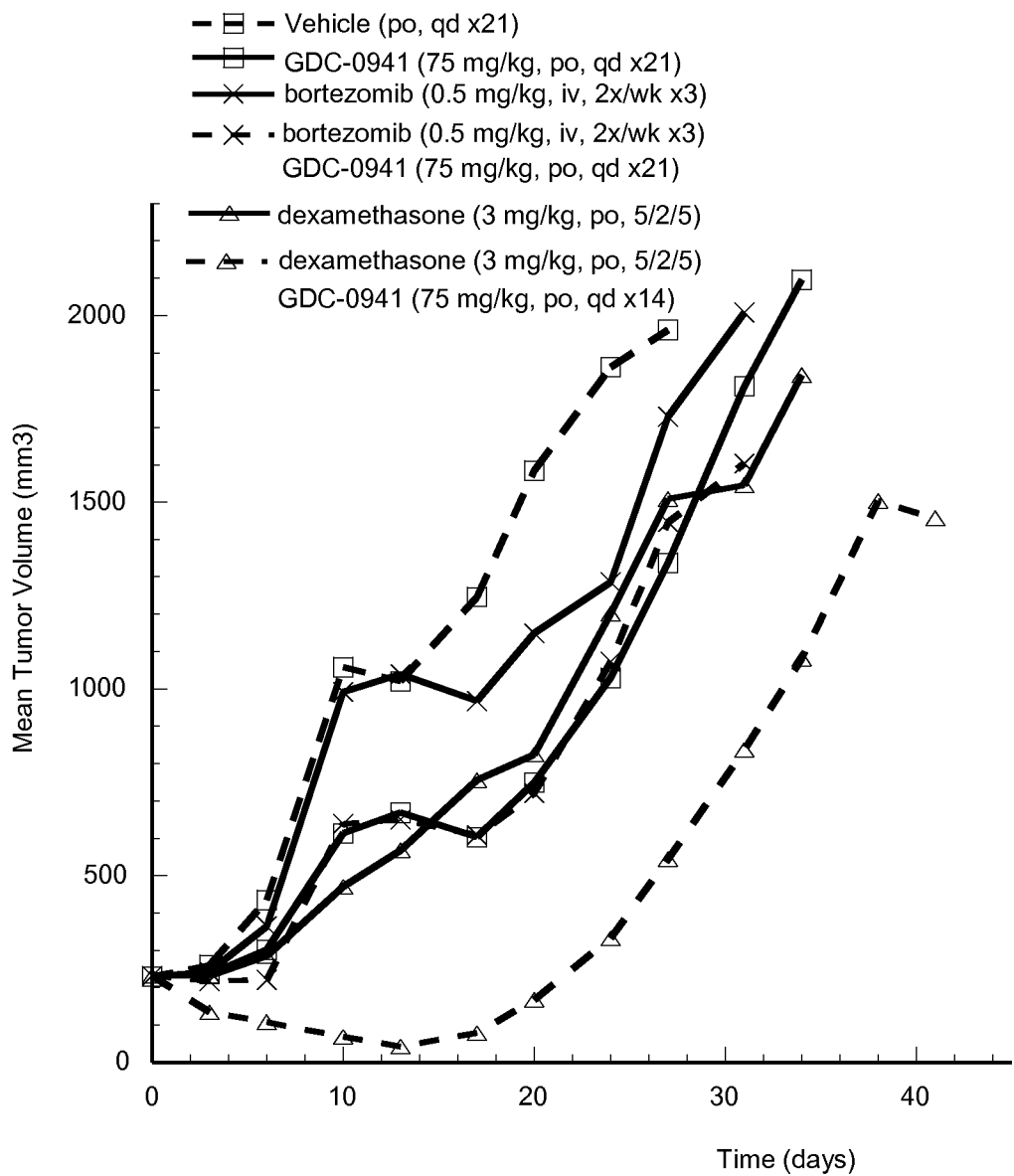
FIG. 15 shows the mean tumor volume change over 40 days in cohorts of 10 mice with multiple myeloma MM1.s cell xenografts dosed on day 0 with: Vehicle (po, qd×21) (0.5% Methylcellulose: 0.2% Tween 80 in DI Water), single agent therapies: 75 mg/kg Formula Ia GDC-0941 (po, qd×21), 0.5 mg/kg bortezomib (iv, 2×/wk×3), and 3 mg/kg dexamethasone (po, 5/2/5); and combinations of: 75 mg/kg Formula Ia GDC-0941 (po, qd×21) and 0.5 mg/kg bortezomib (iv, 2×/wk×3); and 75 mg/kg Formula Ia GDC-0941 (po, qd×21) and 3 mg/kg dexamethasone (po, 5/2/5). Formula Ia GDC-0941 was dosed daily for 21 days by oral gavage. Bortezomib was dosed intravenously on days 0, 3, 7, 10, 14 and 17. Dexamethasone was dosed orally on days 0-4 and 7-11.

FIG. 15 shows the mean tumor volume change over 40 days in cohorts of 10 mice with multiple myeloma MM1.s cell xenografts dosed on day 0 with: Vehicle (po, qd×21) (0.5% Methylcellulose: 0.2% Tween 80 in DI Water), single agent therapies: 75 mg/kg Formula Ia GDC-0941 (po, qd×21), 0.5 mg/kg bortezomib (iv, 2×/wk×3), and 3 mg/kg dexamethasone (po, 5/2/5); and combinations of: 75 mg/kg Formula Ia GDC-0941 (po, qd×21) and 0.5 mg/kg bortezomib (iv, 2×/wk×3); and 75 mg/kg Formula Ia GDC-0941 (po, qd×21) and 3 mg/kg dexamethasone (po, 5/2/5). Formula Ia GDC-0941 was dosed daily for 21 days by oral gavage. Bortezomib was dosed intravenously on days 0, 3, 7, 10, 14 and 17. Dexamethasone was dosed orally on days 0-4 and 7-11. The MM1.s model was relatively refractory to these single agent and combination treatments with one exception;

consistent with in vitro experiments, the GDC-0941 and dexamethasone combination had excellent activity compared to the single agent components. Surprising and unexpectedly, during the time that the GDC-0941 plus dexamethasone cohort were on combination drug treatment, the tumors regressed producing 7 partial responses. No other groups in this study produced objective responses. When dexamethasone treatment was discontinued on day 11, tumors ceased to regress and grew at a rate consistent with continued GDC-0941. These data clearly indicate the unexpected efficacy of the combination of dexamethasone and GDC-0941.

Figure 16:
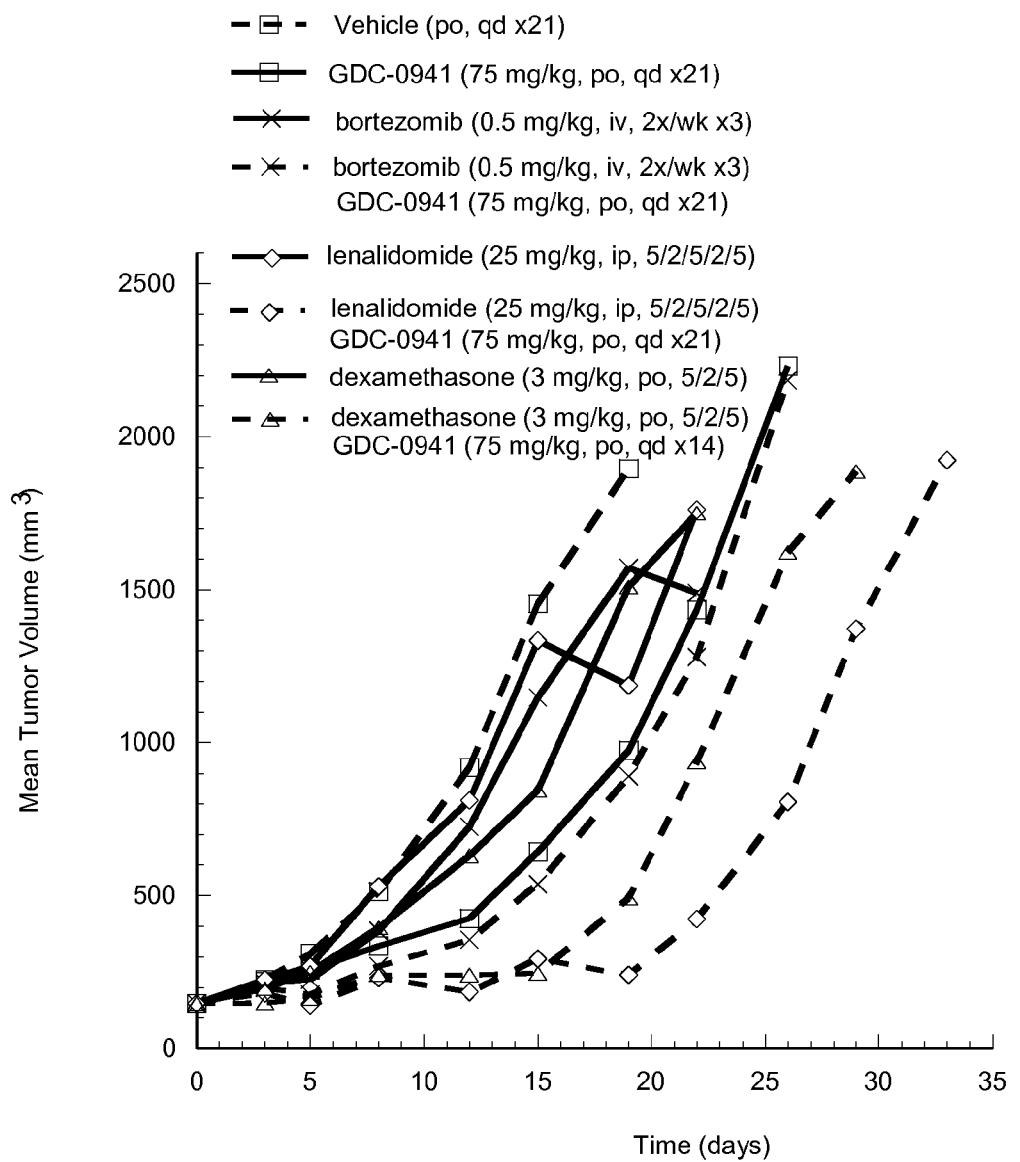
FIG. 16 shows the mean tumor volume change over 33 days in cohorts of 10 mice with multiple myeloma H929 cell xenografts dosed on day 0 with: Vehicle (po, qd×21) (0.5% Methylcellulose: 0.2% Tween 80 in DI Water) single agent therapies: 75 mg/kg Formula Ia GDC-0941 (po, qd×21), 0.5 mg/kg bortezomib (iv, 2×/wk×3), 25 mg/kg lenalidomide (ip, 5/2/5/2/5), and 3 mg/kg dexamethasone (po, 5/2/5); and combinations of: 75 mg/kg Formula Ia GDC-0941 (po, qd×21) and 0.5 mg/kg bortezomib (iv, 2×/wk×3); 75 mg/kg Formula Ia GDC-0941 (po, qd×21) and 25 mg/kg lenalidomide (ip, 5/2/5/2/5); and 75 mg/kg Formula Ia GDC-0941 (po, qd×14) and 3 mg/kg dexamethasone (po, 5/2/5). Formula Ia GDC-0941 was dosed daily for 21 days by oral gavage except when combined with dexamethasone where it was dosed for 14 days. Bortezomib was dosed intravenously on days 0, 3, 7, 10, 14 and 17. Lenalidomide was dosed on days 0-4, 7-11 and 14-18 by intraperitoneal injection. Dexamethasone was dosed orally on days 0-4 and 7-11.

FIG. 16 shows the mean tumor volume change over 33 days in cohorts of 10 mice with multiple myeloma NCI-H929 cell xenografts dosed on day 0 with: Vehicle (po, qd×21) (0.5% Methylcellulose: 0.2% Tween 80 in DI Water) single agent therapies: 75 mg/kg Formula Ia GDC-0941 (po, qd×21), 0.5 mg/kg bortezomib (iv, 2×/wk×3), 25 mg/kg lenalidomide (ip, 5/2/5/2/5), and 3 mg/kg dexamethasone (po, 5/2/5); and combinations of: 75 mg/kg Formula Ia GDC-0941 (po, qd×21) and 0.5 mg/kg bortezomib (iv, qd×3); 75 mg/kg Formula Ia GDC-0941 (po, qd×21) and 25 mg/kg lenalidomide (ip, 5/2/5/2/5); and 75 mg/kg Formula Ia GDC-0941 (po, qd×14) and 3 mg/kg dexamethasone (po, 5/2/5). Formula Ia GDC-0941 was dosed daily for 21 days by oral gavage. Bortezomib was dosed intravenously on days 0, 3, 7, 10, 14 and 17. Lenalidomide was dosed on days 0-4, 7-11 and 14-18 by intraperitoneal injection. Dexamethasone was dosed orally on days 0-4 and 7-11. In the H929 model, the addition of GDC-0941 in the combination groups significantly increased the modest activity of single agent bortezomib, lenalidomide, and dexamethasone.

Figure 17:
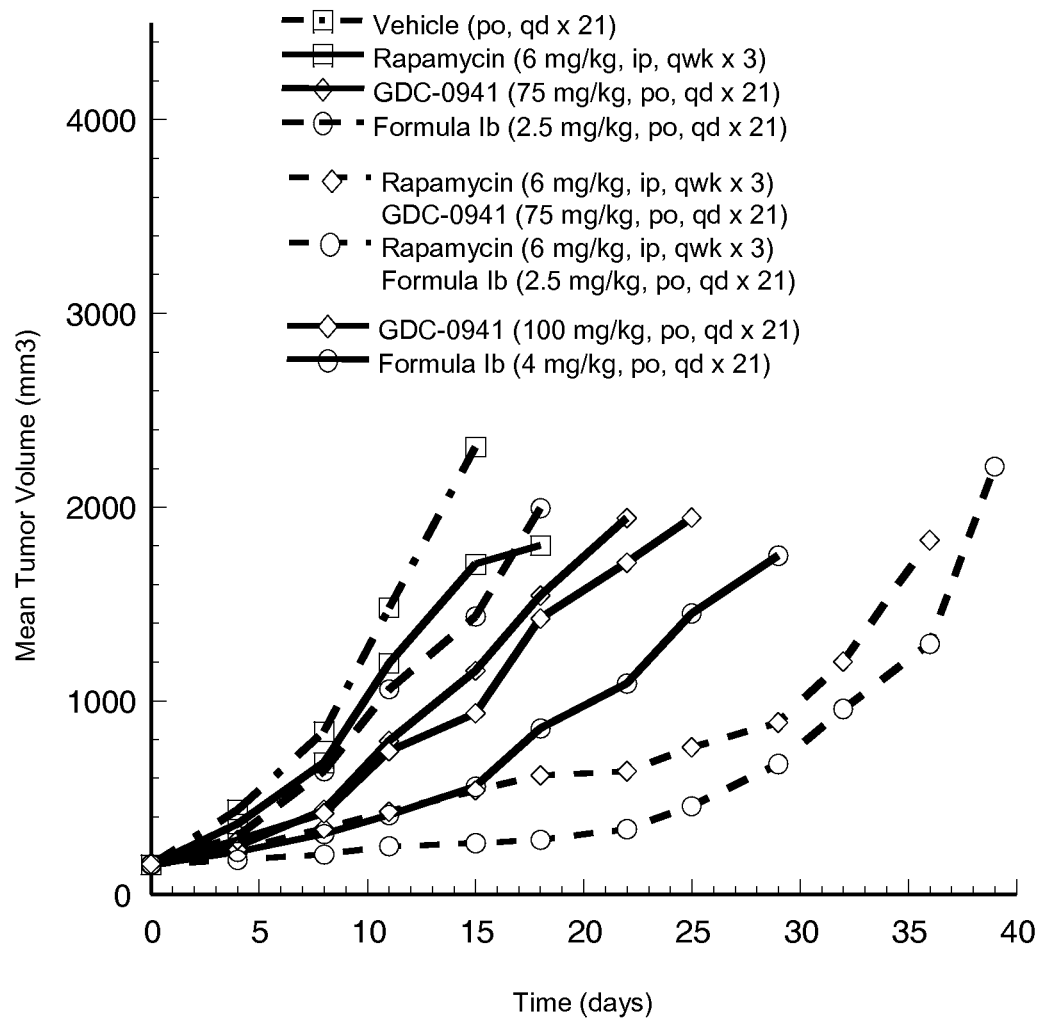
FIG. 17 shows the mean tumor volume change over 33 days in cohorts of 10 mice with DoHH2 lymphoma tumor xenografts dosed on day 0 with: Vehicle (0.5% Methylcellulose: 0.2% Tween 80 in DI Water), 6 mg/kg rapamycin (ip, qwk×3), 75 mg/kg Formula Ia GDC-0941 (po, qd×21), 100 mg/kg Formula Ia GDC-0941 (po, qd×21), 2.5 mg/kg Formula Ib (po, qd×21), 4 mg/kg Formula Ib (po, qd×21); and combinations of: 6 mg/kg rapamycin (ip, qwk×3) and 75 mg/kg Formula Ia GDC-0941 (po, qd×21); and 6 mg/kg rapamycin (ip, qwk×3) and 2.5 mg/kg Formula Ib (po, qd×21). Formula Ia GDC-0941 and Formula Ib were each dosed daily for 21 days by oral gavage. Rapamycin was dosed intravenously on days 0, 7, and 14.

FIG. 17 shows the mean tumor volume change over 40 days for experimental cohorts of 10 mice per group bearing pre-established DoHH2 human lymphoma cell line xenografts dosed on day 0 with: Vehicle (po, qd×20)) 0.5% Methylcellulose:0.2% Tween 80 in DI Water); single agent therapies: 75 mg/kg or 100 mg/kg Formula Ia GDC-0941 (po, qd×20), 2.5 mg/kg or 4 mg/kg Formula Ib (po, qd×20), 6 mg/kg Rapamycin (ip, qw×3); or combination therapies: 75 mg/kg Formula Ia GDC-0941 (po, qd×20) plus 6 mg/kg Rapamycin (ip, qw×3), or 2.5 mg/kg Formula Ib (po, qd×20) plus 6 mg/kg Rapamycin (ip, qw×3). Rapamycin shows little or no significant effect on tumor growth, whereas the single agent treatments show dose-related inhibition of tumor growth while both combinations show significantly enhanced suppression of tumor growth.

Figure 18:
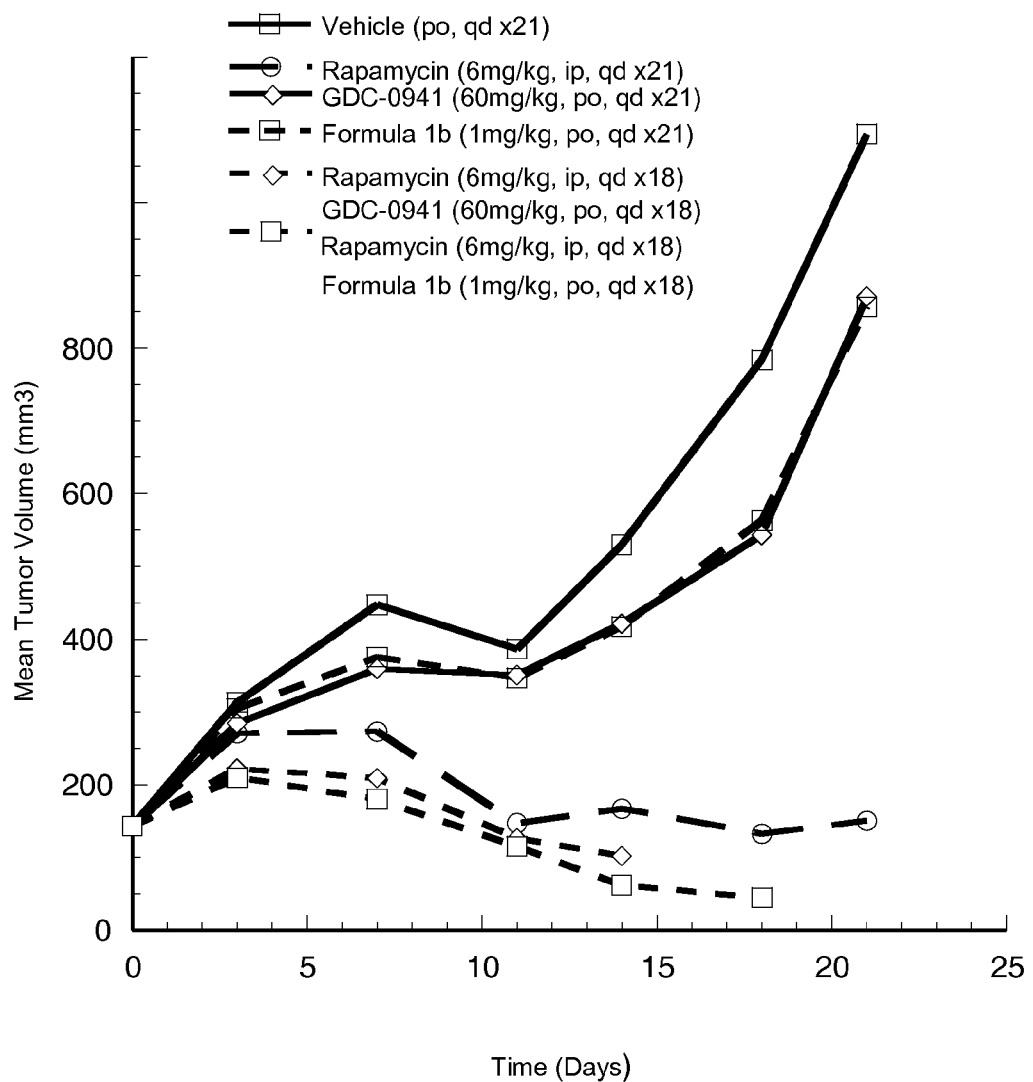
FIG. 18 shows the mean tumor volume change over 21 days in cohorts of 10 mice with WSU-DLCL2 lymphoma tumor xenografts dosed on day 0 with Vehicle (0.5% Methylcellulose: 0.2% Tween 80 in DI Water), 6 mg/kg rapamycin (ip, qwk×3), 60 mg/kg Formula Ia GDC-0941 (po, qd×21), 1 mg/kg Formula Ib (po, qd×21); and combinations of: 6 mg/kg rapamycin (ip, qwk×3) and 60 mg/kg Formula Ia GDC-0941 (po, qd×18); and 6 mg/kg rapamycin (ip, qwk×3) and 1 mg/kg Formula Ib (po, qd×18).

FIG. 18 shows the mean tumor volume change over 25 days for experimental cohorts of 10 mice per group bearing pre-established WSU-DLCL2 human lymphoma cell line xenografts dosed on day 0 with: Vehicle (po, qd×20)) 0.5% Methylcellulose:0.2% Tween 80 in DI Water); single agent therapies: 60 mg/kg Formula Ia GDC-0941 (po, qd×21), 1 mg/kg Formula Ib (po, qd×21), 6 mg/kg Rapamycin (ip, qd×21); or combination therapies: 60 mg/kg Formula Ia GDC-0941 (po, qd×18) plus 6 mg/kg Rapamycin (ip, qd×18), or 1 mg/kg Formula Ib (po, qd×18) plus 6 mg/kg Rapamycin (ip, qd×18). The single agent treatments show little effect on tumor growth, whereas combinations show significantly enhanced suppression of tumor growth.

Pharmaceutical Compositions

Pharmaceutical compositions or formulations of the present invention include combinations of Formula I compounds, a chemotherapeutic agent, and one or more pharmaceutically acceptable carrier, glidant, diluent, or excipient.

The Formula I compounds, and chemotherapeutic agents of the present invention may exist in unsolvated as well as solvated forms with pharmaceutically acceptable solvents such as water, ethanol, and the like, and it is intended that the invention embrace both solvated and unsolvated forms.

The Formula I compounds, and chemotherapeutic agents of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents including a Formula I compound and a chemotherapeutic agent selected from the lists of the additional agents described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the methods of treating a patient by administering a pharmaceutical composition is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium ($^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Formula I compounds and chemotherapeutic agents are formulated in accordance with standard pharmaceutical practice for use in a therapeutic combination for therapeutic treatment (including prophylactic treatment) of hyperproliferative disorders in mammals including humans. The invention provides a pharmaceutical composition comprising a Formula I compound in association with one or more pharmaceutically acceptable carrier, glidant, diluent, additive, or excipient.

Suitable carriers, diluents, additives, and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), dimethylsulfoxide (DMSO), cremophor (e.g. CREMOPHOR EL®, BASF). and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a Formula I compound having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The initial pharmaceutically effective amount of the Formula I compound administered orally or parenterally per dose will be in the range of about 0.01-1000 mg/kg, namely about 0.1 to 20 mg/kg of patient body weight per day, with the typical initial range of compound used being 0.3 to 15 mg/kg/day. The dose of the Formula I compound and the dose of the chemotherapeutic agent to be administered may range for each from about 1 mg to about 1000 mg per unit dosage form, or from about 10 mg to about 100 mg per unit dosage form. The doses of Formula I compound and the chemotherapeutic agent may administered in a ratio of about 1:50 to about 50:1 by weight, or in a ratio of about 1:10 to about 10:1 by weight.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, CREMOPHOR EL®, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 18th edition, (1995) Mack Publ. Co., Easton, Pa.

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D (−) 3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I and/or chemotherapeutic agent suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of a compound of Formula I and/or a chemotherapeutic agent. The amount of compound of Formula I and the amount of chemotherapeutic agent may be formulated in a pill, capsule, solution or suspension as a combined formulation. Alternatively, the Formula I compound and the chemotherapeutic agent may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablet excipients of a pharmaceutical formulation of the invention may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tabletting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

The aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the pharmaceutical formulations of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

Formula I compounds may be employed in combination with certain chemotherapeutic agents for the treatment of a hematopoietic malignancy, along with pre-malignant and non-neoplastic or non-malignant hyperproliferative disorders. In certain embodiments, a compound of Formula I is combined in a pharmaceutical combination formulation, or dosing regimen as combination therapy, with a chemotherapeutic agent that has anti-hyperproliferative properties or that is useful for treating the hematopoietic malignancy. The chemotherapeutic agent of the pharmaceutical combination formulation or dosing regimen preferably has complementary activities to the Formula I compound, and such that they do not adversely affect each other. Such compounds of the therapeutic combination may be administered in amounts that are effective for the purpose intended. In one embodiment, a pharmaceutical formulation of this invention comprises a Formula I compound and a chemotherapeutic agent such as described herein. In another embodiment, the therapeutic combination is administered by a dosing regimen wherein the therapeutically effective amount of a Formula I compound is administered in a range from twice daily to once every three weeks (q3wk), and the therapeutically effective amount of the chemotherapeutic agent is administered separately, in alternation, in a range from twice daily to once every three weeks.

Therapeutic combinations of the invention include a product comprising a Formula I compound, and a chemotherapeutic agent selected from dexamethasone, thioTEPA, doxorubicin, vincristine, rituximab, cyclophosphamide, prednisone, melphalan, lenalidomide, bortezomib, rapamycin, and cytarabine, as a combined preparation for separate, simultaneous or sequential use in the treatment of a hyperproliferative disorder.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, the therapeutic combination may be combined with surgical therapy and radiotherapy, as adjuvant therapy. Combination therapies according to the present invention include the administration of at least one Formula I compound and one or more other cancer treatment methods or modalities. The amounts of the Formula I compound(s) and the chemotherapeutic agent(s) and the relative timings of administration will be selected in order to achieve the desired combined therapeutic effect.

Administration of Pharmaceutical Compositions

The therapeutic combinations of the invention may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, $18^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 10 mg to about 1000 mg of Formula I compound, such as about 100 mg to about 300 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

Methods of Treatment

Therapeutic combinations of: (1) a Formula I compound and (2) a chemotherapeutic agent are useful for treating diseases, conditions and/or disorders including, but not limited to, those characterized by activation of the PI3 kinase pathway. Accordingly, another aspect of this invention includes methods of treating diseases or conditions that can be treated by inhibiting lipid kinases, including PI3. In one embodiment, a method for the treatment of a hematopoietic malignancy comprises administering a therapeutic combination as a combined formulation or by alternation to a mammal, wherein the therapeutic combination comprises a therapeutically effective amount of a compound having Formula I, and a therapeutically effective amount of one or more chemotherapeutic agents selected from dexamethasone, thioTEPA, doxorubicin, vincristine, rituximab, cyclophosphamide, prednisone, melphalan, lenalidomide, bortezomib, rapamycin, and cytarabine. Therapeutic combinations of: (1) a Formula I or II compound and (2) a chemotherapeutic agent may be employed for the treatment of a hyperproliferative disease or disorder, including tumors, cancers, and neoplastic tissue, along with pre-malignant and non-neoplastic or non-malignant hyperproliferative disorders. In one embodiment, a human patient is treated with a therapeutic combination and a pharmaceutically acceptable carrier, adjuvant, or vehicle, wherein the Formula I compound, or metabolite thereof, of said therapeutic combination is present in an amount to detectably inhibit PI3 kinase activity.

Hematopoietic malignancies include non-Hodgkin's lymphoma, diffuse large hematopoietic lymphoma, follicular lymphoma, mantle cell lymphoma, chronic lymphocytic leukemia, multiple myeloma, AML, MCL Another aspect of this invention provides a pharmaceutical composition or therapeutic combination for use in the treatment of the diseases or conditions described herein in a mammal, for example, a human, suffering from such disease or condition. Also provided is the use of a pharmaceutical composition in the preparation of a medicament for the treatment of the diseases and conditions described herein in a warm-blooded animal, such as a mammal, for example a human, suffering from such disorder.

Metabolites of Formula I Compounds

Also falling within the scope of this invention are the in vivo metabolic products of Formula I compounds described herein. Such products may result for example from the oxidation, reduction, hydrolysis, amidation, deamidation, esterification, deesterification, enzymatic cleavage, and the like, of the administered compound. Accordingly, the invention includes metabolites of Formula I compounds, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing Formula I compounds useful for the treatment of the diseases and disorders described above is provided. In one embodiment, the kit comprises a container comprising a Formula I compound. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a Formula I compound. The label or package insert indicates that the composition is used for treating the condition of choice, such as cancer. In one embodiment, the label or package inserts indicates that the composition comprising a Formula I compound can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of Formula I and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Preparative Procedures

General Procedure A-1 Suzuki Coupling:

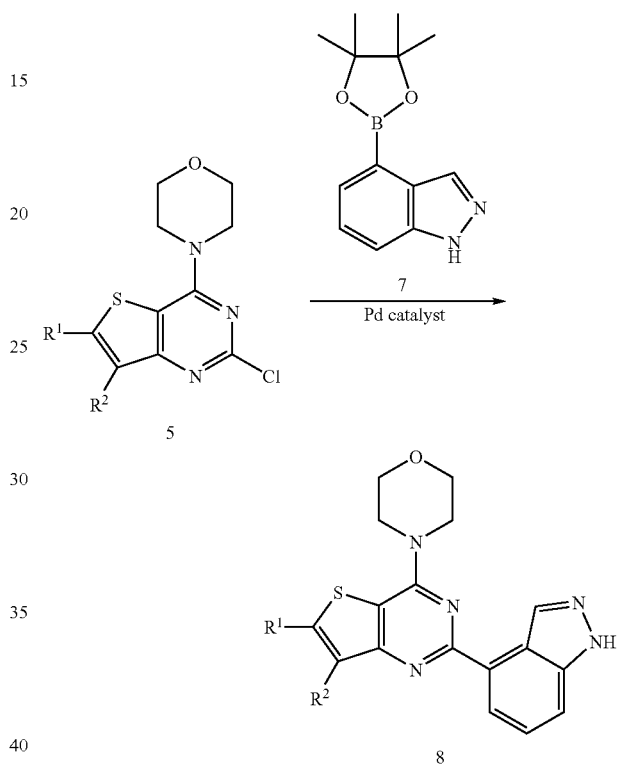

The Suzuki-type coupling reaction is useful to attach a fused bicyclic heterocycle or heteroaryl at the 2-position of the pyrimidine ring (see Scheme 4). Generally, substituted 2-chloro-4-morpholinothieno[3,2-d]pyrimidine 5 may be combined with 1.5 equivalents of 4-(4,4,5,5-tetramethyl-1,3, 2-dioxaborolan-2-yl)1H-indazole 7, and dissolved in 3 equivalents of sodium carbonate as a 1 molar solution in water and an equal volume of acetonitrile. Intermediate 7 was prepared according to the methods of US 2008/0039459; US 2008/0076768; US 2008/0076758; US 2008/0207611, incorporated by reference herein. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, the nitrogen of the indazole may be protected, for example with a tetrahydropyranyl group. In some cases potassium acetate was used in place of sodium carbonate to adjust the pH of the aqueous layer. The reaction was then heated to about 140-150° C. under pressure in a Biotage Optimizer microwave reactor (Biotage, Inc.) for 10 to 30 minutes. The contents are extracted with ethyl acetate, or another organic solvent. After evaporation of the organic layer the product 8 may be purified on silica or by reverse phase HPLC.

General Procedure A-2 Suzuki Coupling:

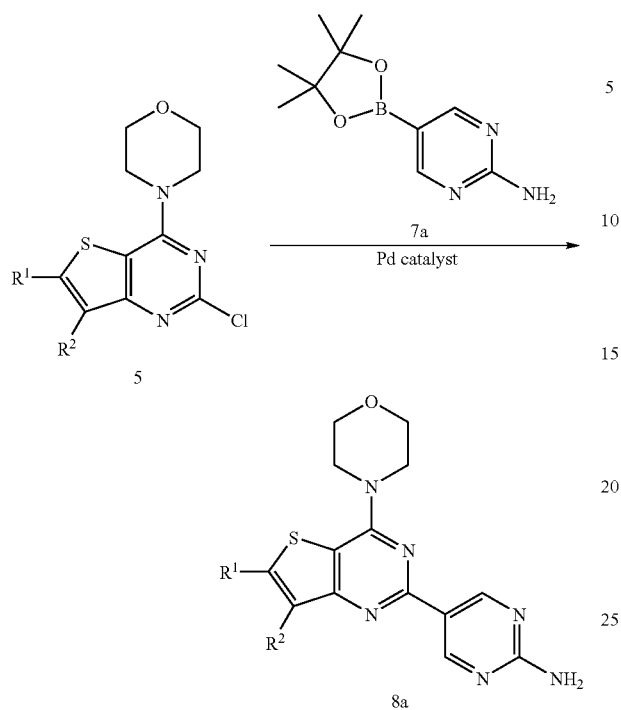

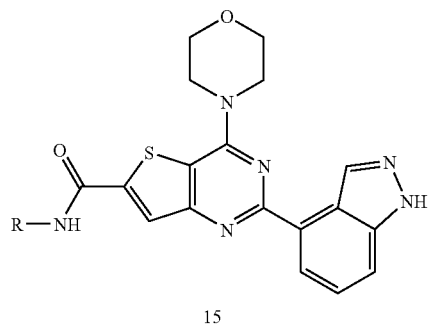

The Suzuki-type coupling reaction is useful to attach a monocyclic heteroaryl at the 2-position of the pyrimidine ring (see Scheme 4). Generally, substituted 2-chloro-4-morpholinothieno[3,2-c]pyrimidine 5 may be combined with 1.5 equivalents of 5-(4,4,5,5-tetramethyl-1,3,2-dioxaborolan-2-yl)pyrimidin-2-amine 7a, and dissolved in 3 equivalents of sodium or potassium carbonate as a 1 molar solution in water and an equal volume of acetonitrile. Intermediate 7a was prepared according to the methods of US 2008/0269210; US 2008/0242665, incorporated by reference herein. A catalytic amount, or more, of a low valent palladium reagent, such as bis(triphenylphosphine)palladium(II) dichloride, is added. A variety of boronic acids or boronic esters can be used in place of the pinacol boronic ester indicated. Also alternatively, the nitrogen of the pyrimidin-2-amine may be protected, for example with a tetrahydropyranyl group. In some cases potassium acetate was used in place of sodium carbonate to adjust the pH of the aqueous layer. The reaction was then heated, for example to about 100-150° C. under pressure in a Biotage Optimizer microwave reactor (Biotage, Inc.) for 10 to 30 minutes. The contents are extracted with ethyl acetate, or another organic solvent. After evaporation of the organic layer the product 8a may be purified on silica or by reverse phase HPLC.

General Procedure B Amide Coupling:

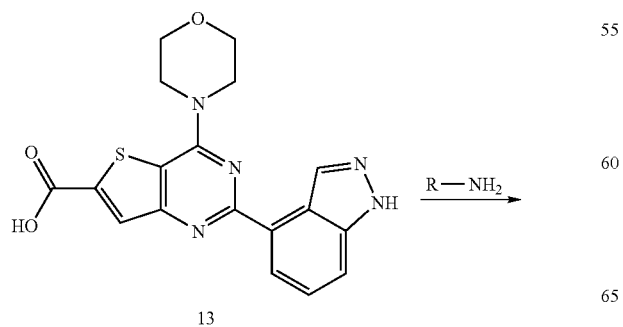

2-(1H-Indazol-4-yl)-4-morpholinothieno[3,2-d]pyrimidine-6-carboxylic acid 13 is treated with 1.5 eq HATU, 3 eq of alkylamine and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield product 15.

General Procedure B-1 Amide Coupling:

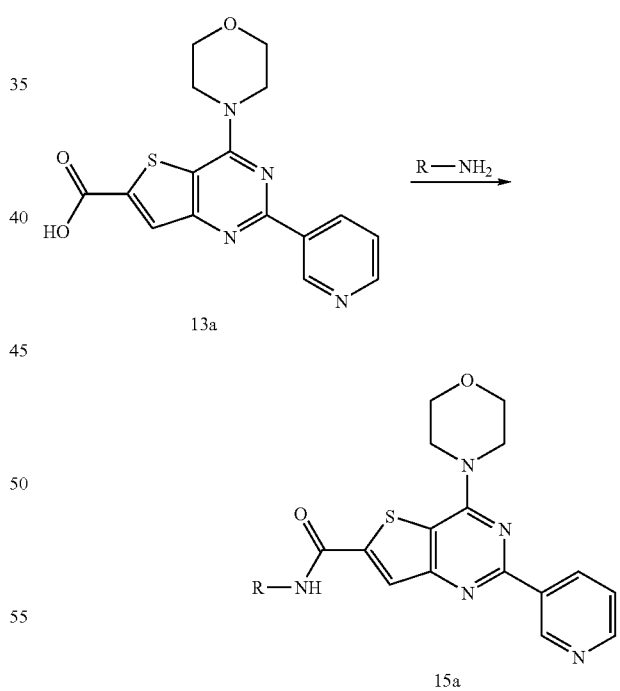

4-Morpholino-2-(pyridin-3-yl)thieno[3,2-d]pyrimidine-6-carboxylic acid 13a is treated with 1.5 eq HATU, 3 eq of an alkylamine (R—NH$_2$) and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield product 15a.

General Procedure B-2 Amide Coupling:

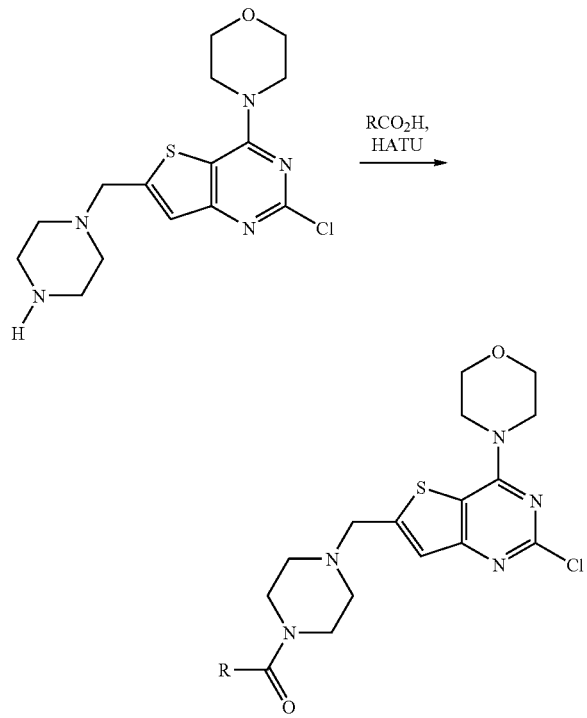

2-Chloro-4-morpholino-6-((piperazin-1-yl)methyl)thieno[3,2-d]pyrimidine is treated with about 1.5 eq of a coupling reagent such as HATU, about 3 eq of a carboxylic acid ($RCO_2H$) and an excess of an amine base such as DIPEA in DMF to approximately 0.1 M concentration. The reaction is stirred until complete and extracted in ethyl acetate with saturated bicarbonate solution one time. The organic layer is dried, filtered and concentrated to yield the crude intermediate.

General Procedure B-3 Reductive Amination:

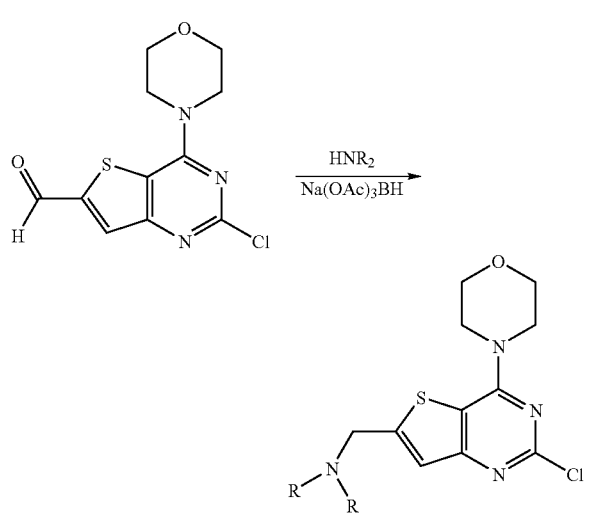

2-Chloro-4-morpholinothieno[3,2-d]pyrimidine-6-carbaldehyde is dissolved to a 0.2 M concentration in dichloroethane. To this solution is added 1.5 to 2.0 equivalents of a primary or secondary amine ($R_2NH$), about 10 equivalents of trimethylorthoformate, and about 1 equivalent of acetic acid. The mixture is allowed to stir for 2-6 hours prior to adding 1.5 equivalents of sodium triacetoxyborohydride. Following 12 to 16 hours of stirring the reaction was poured into saturated sodium bicarbonate and extracted several times with ethyl acetate to give the reductive amination intermediate which is either purified on silica gel or used crude in the next reaction.

General Procedure C Sulfonamide Formation:

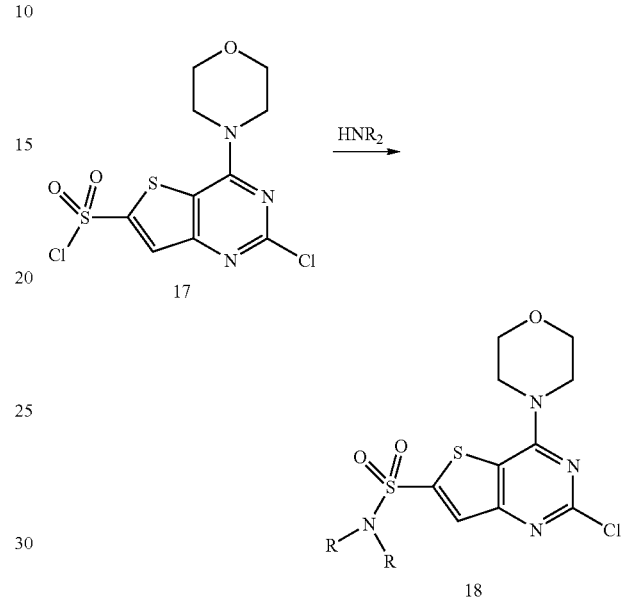

2-Chloro-4-morpholinothieno[3,2-d]pyrimidine-6-sulfonyl chloride 17 is suspended in DCM before addition of about 2 eq of amine ($HNR_2$) and about 3 eq of an amine base such as DIPEA. The reactions are monitored by LCMS until complete. The crude reaction mixtures are diluted with ethyl acetate, extracted with saturated ammonium chloride and back-extracted once with ethyl acetate. The organic layers were combined and concentrated to dryness. The crude sulfonamide intermediates 18 are used directly in the subsequent Suzuki couplings.

General Procedure D Alcohol Synthesis

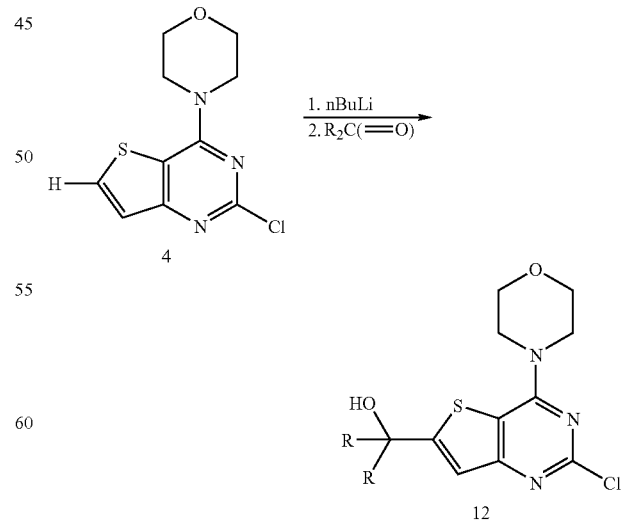

2-Chloro-4-morpholinothieno[3,2-d]pyrimidine 4 is suspended to a 0.2 molar concentration in THF and cooled to −50° C. in a dry ice/acetonitrile bath before adding 2 equivalents of 2.5 M nBuLi in hexanes. After 15 min 3.0 molar equivalents of a cyclic or acyclic ketone (R$_2$C(=O) is added to the solution. The reaction continued to stir at −50° C. for 1 h and then in most cases was allowed to come to 0° C. When the reaction is complete by TLC or mass spec. it is quenched into a saturated ammonium chloride solution and extracted two times with EtOAc. The organic layer is concentrated and either used as a crude mixture, purified on silica, or the product 12 could be dissolved in a minimal amount of acetonitrile and filtered to remove remaining starting material 4.

General Procedure E Removal of t-Butoxylcarbonyl (BOC) Group

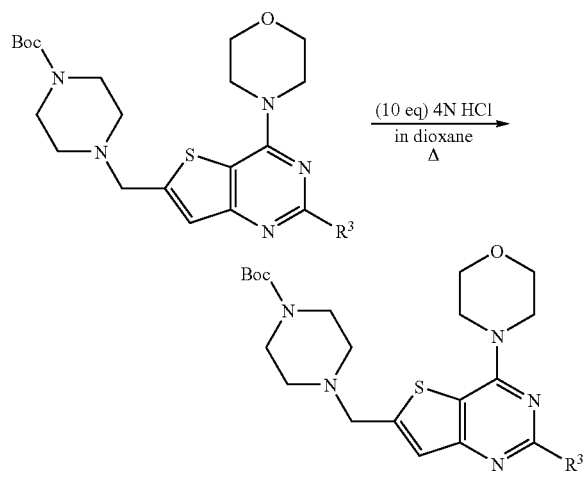

Ten or more equivalents of 4N HCl in dioxane, with or without dichloromethane as a co-solvent, are added to the starting material (general scheme shown above but similar scaffolds also used). Heating up to 40° C. for several hours is occasionally required to remove the Boc group. The reaction is concentrated to dryness and may be used crude in subsequent reactions.

General Procedure F Suzuki Coupling Reactions in One Pot

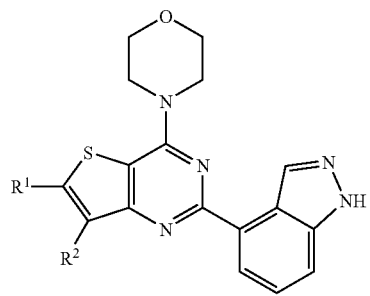

2-Chloro-6-iodo-4-morpholinothieno[3,2-d]pyrimidine 19 (1 eq), phenylboronic acid or heterocycleboronic acid (R$^1$—B(OH)$_2$, 1.1 eq) and bis(triphenylphosphine)palladium (II) dichloride (0.1 eq) in 1M Na$_2$CO$_3$ aqueous solution (3 eq) and acetonitrile (3 eq) was heated to 100° C. in a sealed microwave reactor for 10 to 40 min to give 5. Upon completion, 4-(4,4,5,5-tetramethyl-1,3,2-dioxaborolan-2-yl)-1H-indazole 7 (1.3 eq) and bis(triphenylphosphine)palladium(II) dichloride (0.1 eq) were added in the same pot. The reaction mixture was heated to 150° C. in a sealed microwave reactor for 10 to 15 min. The mixture was extracted with ethyl acetate (3×5 mL). The combined organic layers were concentrated to yield crude 8.

General Procedure G Amide Coupling Reaction

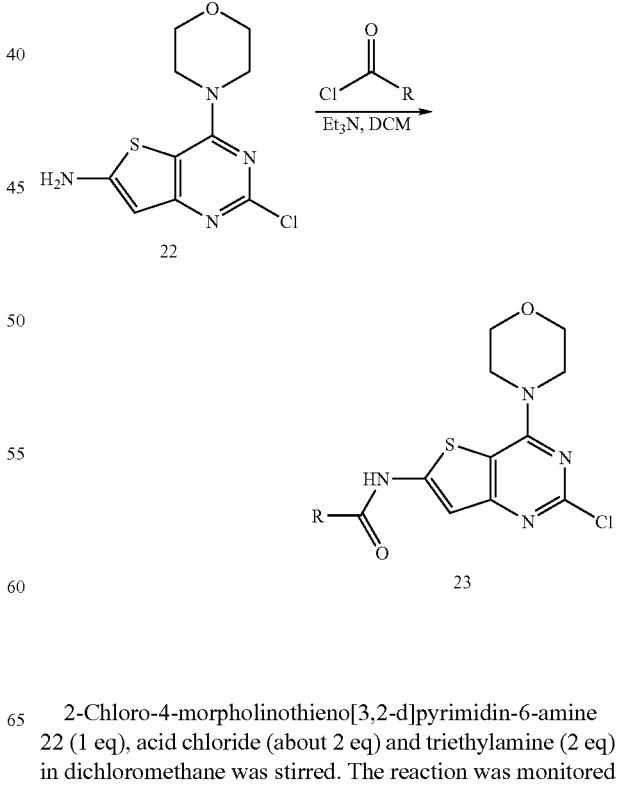

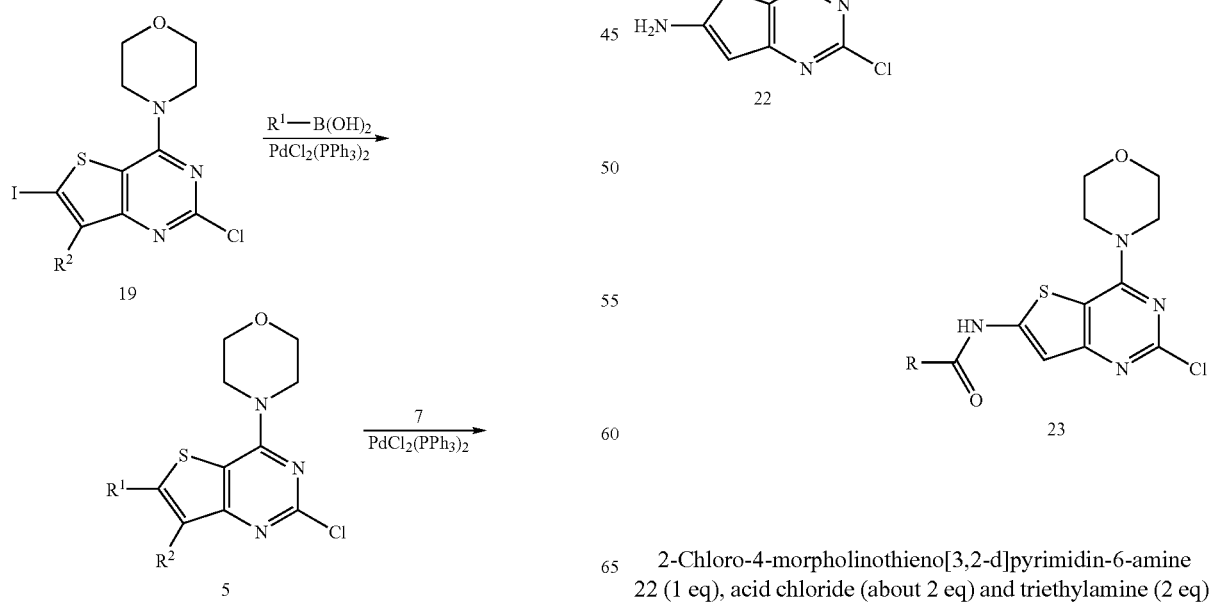

2-Chloro-4-morpholinothieno[3,2-d]pyrimidin-6-amine 22 (1 eq), acid chloride (about 2 eq) and triethylamine (2 eq) in dichloromethane was stirred. The reaction was monitored by LC/MS until complete. The mixture was evaporated to give the crude amide 23, which was directly used for the next step reaction without purification.

General Procedure H Preparation of Acetamide, Benzamidines, and Sulfonamides

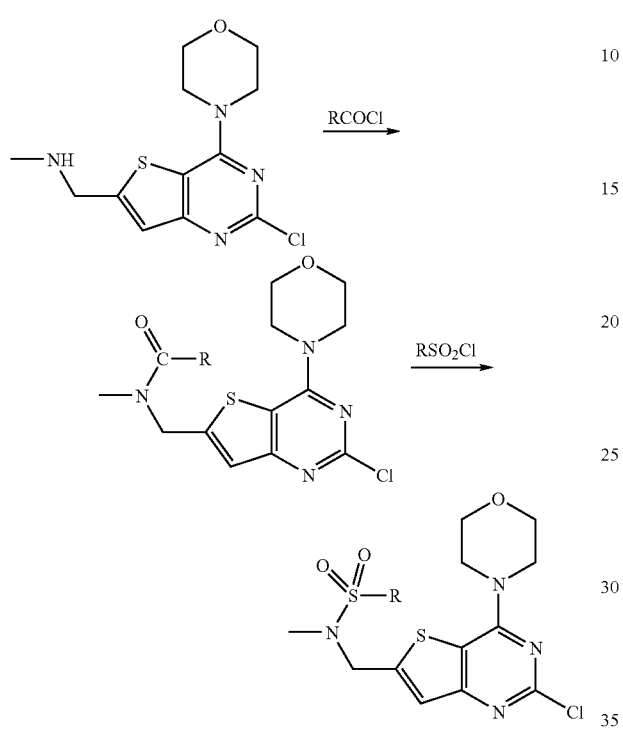

To a 0.25 to 0.40 M solution of 1-(2-chloro-4-morpholinothieno[2,3-d]pyrimidin-6-yl)-N-methylmethanamine in DCM cooled to 0° C. was added 1.5 eq. of TEA, followed by the drop-wise addition of 1.0 to 1.5 eq. of an alkyl or aryl-acid chloride or a sulfonylchloride, diluted in DCM. The reaction is stirred at ambient temperature and monitored for completeness by LCMS. After completion, the reaction volume is increased with DCM, and dilute aqueous sodium bicarbonate is added to the solution. The organic and aqueous layers are separated. Finally, the organic layer is washed with brine and dried (MgSO$_4$). The dried organic solution is concentrated in vacuo and the product is purified by silica chromatography if necessary.

General Procedure I Amide Coupling Reaction for Benzenamine

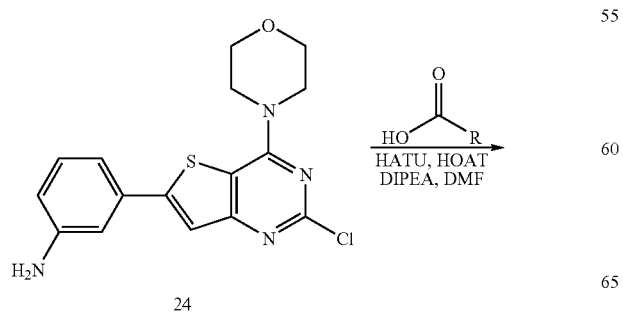

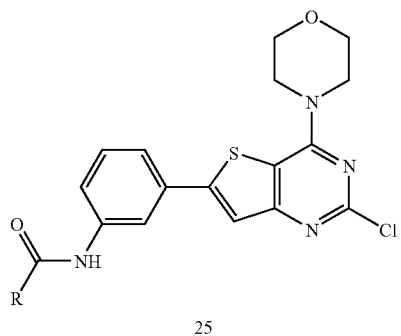

3-(2-Chloro-4-morpholinothieno[3,2-d]pyrimidin-6-yl)benzenamine 24 (leg), carboxylic acid (1.5 eq), 1-hydroxy-7-azabenzotriazole (0.2 eq), O-(7-azabenzotriazol-1-yl)-(N,N,N',N'-tetramethyluronium hexafluorophosphate (HATU, 1.5 eq), and N,N-diisopropylethylamine (2.5 eq) in DMF was stirred at room temperature. The reaction was monitored by LC/MS until complete. The reaction mixture was diluted with ethyl acetate, washed with saturated sodium bicarbonate and brine. The organic layer was dried over MgSO$_4$, filtered and evaporated to yield amide product 25.

General Procedure J 6-Iodo Displacement and 2-Suzuki Coupling

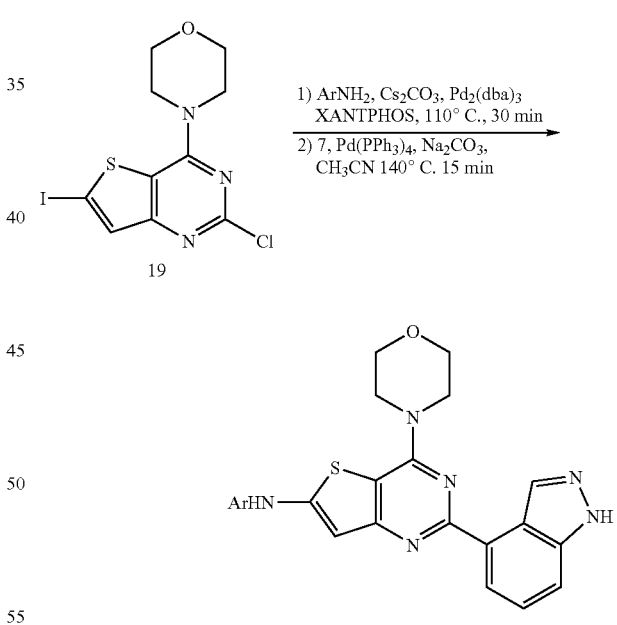

To a solution of 2-chloro-6-iodo-4-morpholinothieno[3,2-d]pyrimidine 19 (0.05 g, 0.13 mmol) in DMF (1.00 mL) was added the appropriate aniline (200 mol %), Cs—$_2$CO$_3$ (50 mol %), Pd$_2$(dba)$_3$ (5 mol %), and XANTPHOS (10 mol %). The reaction was heated to 110° C. under pressure in a Biotage optimizer microwave reactor for 30 min. The resulting solution was concentrated in vacuo to give 26, after following General Procedure A.

General Procedure K 6-Aminoalkyl Acylation and 2-Suzuki Coupling

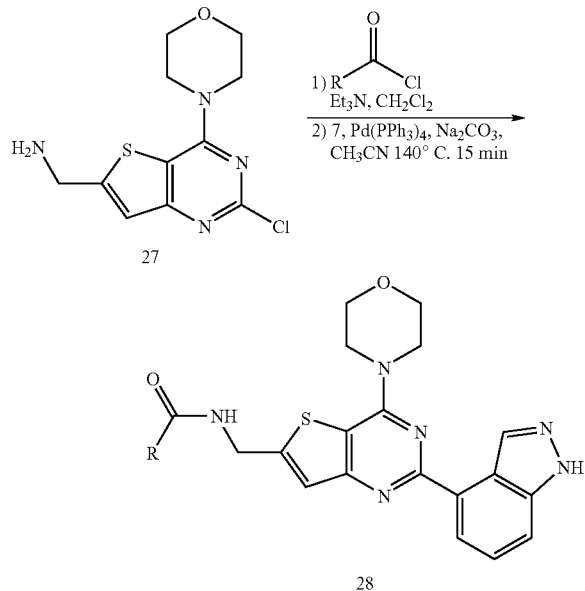

To a solution of (2-chloro-4-morpholinothieno[3,2-d]pyrimidin-6-yl)methanamine 27 (50 mg, 0.2 mmol) in $CH_2Cl_2$ (4 mL) was added $Et_3N$ (84 μt, 0.6 mmol) and the appropriate acid chloride or HCl salt thereof (0.3 mmol). The reaction stirred 18-48 hr at room temperature before being quenched with water. The aqueous layer was extracted with EtOAc. The combined organics were dried over $Na_2SO_4$ and concentrated in vacuo. The 2-chloro crude product was coupled with boronate reagent 7 and palladium catalyst according to General Procedure A to give 28 which was purified by reversed phase HPLC purification.

Alternatively, to a solution of (2-chloro-4-morpholinothieno[3,2-d]pyrimidin-6-yl)methanamine 27 (111 mg, 0.39 mmol) in DMF (5 mL) was added 2,6-lutidine (48.2 μt, 0.41 mmol) and the appropriate acid chloride or HCl salt thereof (0.39 mmol). The reaction stirred 18-72 hr at room temperature before being quenched with water. The aqueous layer was extracted with EtOAc. The combined organics were dried over $MgSO_4$ and concentrated in vacuo. The 2-chloro crude product was coupled with boronate reagent 7 and palladium catalyst according to General Procedure A to give 20 mg of 28 which was purified by reversed phase HPLC purification.

General Procedure L Amine Substitution on Fluoropyridine

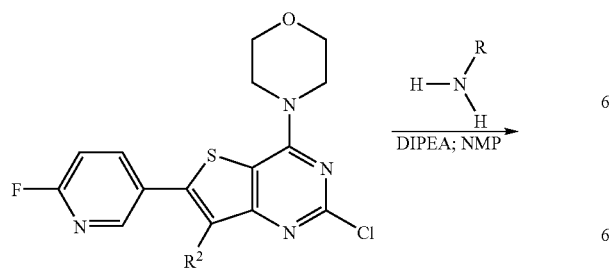

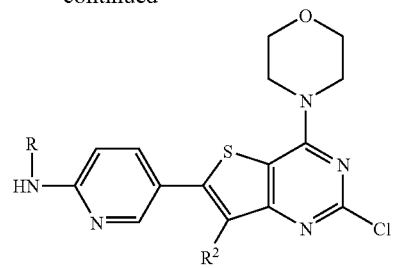

A mixture of 2-chloro-6-(6-fluoropyridin-3-yl)-4-morpholinothieno[3,2-d]pyrimidine, about four equivalents of a primary or secondary amine (R=H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl), and about two eq. diisopropylethylamine in N-methylpyrrolidine (~0.1M) is heated to about 130-140° C. in a sealed microwave reactor for 10-40 min, followed by removal of volatiles under high vacuum. The crude mixture is purified by flash chromatography to give intermediate 2-chloro-6-(6-aminopyridin-3-yl)-4-morpholinothieno[3,2-d]pyrimidine, which may be Suzuki coupled with a monocyclic heteroaryl, fused bicyclic heterocycle or heteroaryl boronate reagent following General Procedure A.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Example 1

2,4-Dichloro-thieno[3,2-d]pyrimidine 3

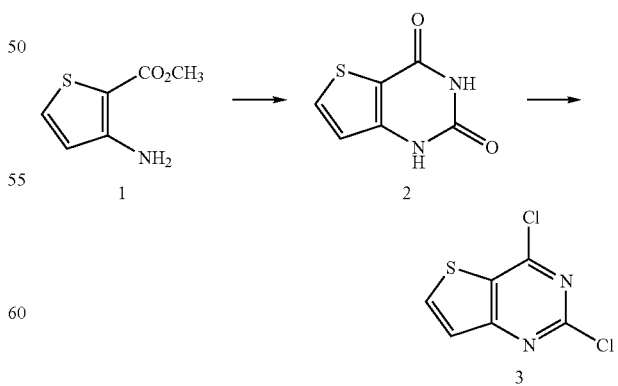

A mixture of methyl 3-amino-2-thiophenecarboxylate 1 (13.48 g, 85.85 mmol) and urea (29.75 g, 5 eq.) was heated at 190° C. for 2 hours. The hot reaction mixture was poured onto sodium hydroxide solution and any insoluble material was removed by filtration. The mixture was then acidified (HCl, 2N) to yield 1H-thieno[3,2-d]pyrimidine-2,4-dione 2 as a white precipitate, which was collected by filtration and air dried (9.49 g, 66%). $^1$H NMR 400 MHz, d$_6$-DMSO) 6.90 (1H, d, J=5.2 Hz), 8.10 (1H, d, J=5.2 Hz), 11.60-11.10 (2H, br s).

A mixture of 1H-thieno[3,2-d]pyrimidine-2,4-dione 2 (9.49 g, 56.49 mmol) and phosphorous oxychloride (150 mL) was heated at reflux for 6 h. The reaction mixture was then cooled and poured onto ice/water with vigorous stirring yielding a precipitate. The mixture was then filtered to yield 2,4-dichloro-thieno[3,2-d]pyrimidine 3 as a white solid (8.68 g, 75%). $^1$H NMR (400 MHz, CDCl$_3$) 7.56 (1H, d, J=5.5 Hz), 8.13 (1H, d, J=5.5 Hz).

Example 2

2-Chloro-4-morpholin-4-yl-thieno[3,2-d]pyrimidine 4

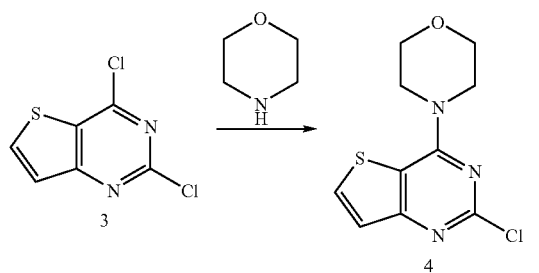 [SMILES: Clc1nc(Cl)c2sccc2n1 ; C1COCCN1 ; Clc1nc(N2CCOCC2)c2sccc2n1]

A mixture of 2,4-dichloro-thieno[3,2-d]pyrimidine 3, (8.68 g, 42.34 mmol), morpholine (8.11 mL, 2.2 eq.) and MeOH (150 mL) was stirred at room temperature for 1 h. The reaction mixture was then filtered, washed with water and MeOH, to yield 2-chloro-4-morpholin-4-yl-thieno[3,2-d]pyrimidine 4 as a white solid (11.04 g, 100%). $^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

Example 3

2-Chloro-4-morpholin-4-yl-thieno[3,2-d]pyrimidine-6-carbaldehyde 10

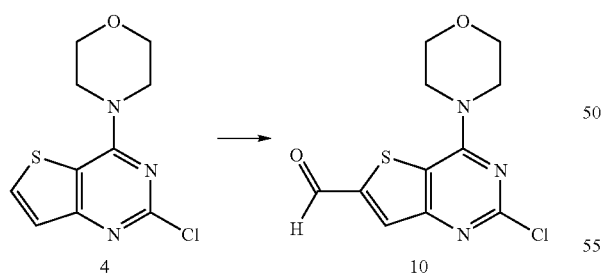

To a suspension of 2-chloro-4-morpholin-4-yl-thieno[3,2-d]pyrimidine 4 (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 μL, 1.5 eq.) was added. The reaction mixture was stirred for 1 h at −78° C. and then warmed slowly to room temperature. After a further 2 h at room temperature the reaction mixture poured onto ice/water yielding a yellow precipitate. This was collected by filtration and air-dried to yield 2-chloro-4-morpholin-4-yl-thieno[3,2-d]pyrimidine-6-carbaldehyde 10 (1.50 g, 77%). $^1$H NMR (400 MHz, d$_6$-DMSO) 3.76 (4H, t, J=4.9), 3.95 (4H, t, J=4.9), 8.28 (1H, s), 10.20 (1H, s).

Example 4

2-Chloro-6-iodo-7-methyl-4-morpholinothieno[3,2-d]pyrimidine 41

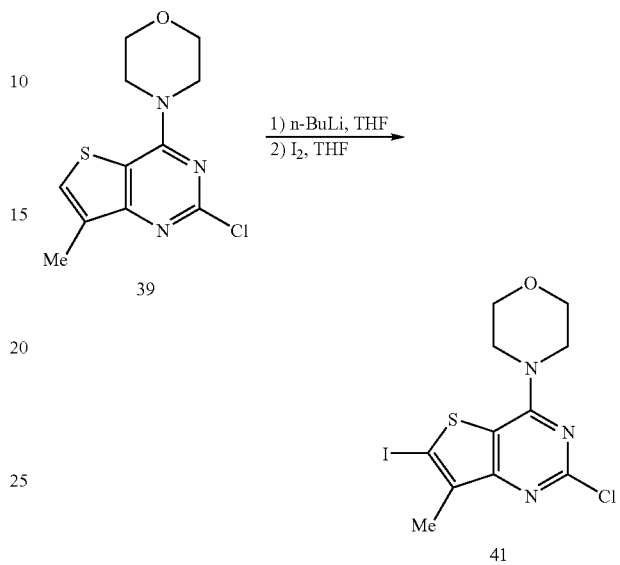

To a solution of 2-chloro-7-methyl-4-morpholinothieno[3,2-d]pyrimidine 39 (3.0 g, 11.1 mmol; prepared according to the procedure for the synthesis of 2-chloro-4-morpholin-4-yl-thieno[3,2-d]pyrimidine but commencing with 3-amino-4-methyl-thiophene-2-carboxylic acid ethyl ester) in THF (60 mL) at −78° C. was added n-BuLi (8.9 mL, 2.5 M in Et$_2$O). The resulting slurry was warmed to −40° C. and stirred 50 min. The reaction mixture was then cooled to −78° C. and a solution of I$_2$ (5.6 g, 22.2 mmol) in THF (30 mL) was added. The solution was warmed to room temperature and stirred 5 h. The reaction was quenched by the addition of water. The organic layer was separated and the aqueous layer was extracted with CH$_2$Cl$_2$. The combined organics were washed with saturated aqueous Na$_2$S$_2$O$_3$, dried over Na$_2$SO$_4$, filtered, and concentrated in vacuo to provide 2-chloro-6-iodo-7-methyl-4-morpholinothieno[3,2-c]pyrimidine 41 (3.8 g, 84% yield).

Example 5

4-(2-Chloro-6-(piperazin-1-ylmethyl)thieno[3,2-d]pyrimidin-4-yl)morpholine 30

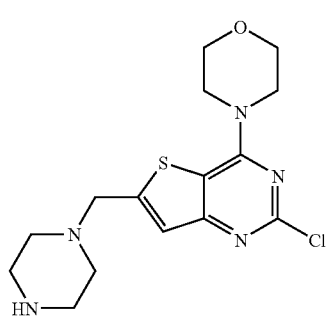

A mixture of 2-chloro-4-morpholin-4-yl-thieno[3,2-d]pyrimidine-6-carbaldehyde 10 (3.5 g), 1-BOC-piperazine (2.76 g) and trimethylorthoformate (4.05 mL) was stirred in 1,2- dichloroethane (300 mL) for 1 hr at room temperature. To this was added sodium triacetoxyborohydride (3.92 g) and the reaction mixture was stirred for 24 hours at room temperature. The mixture was then quenched with brine, extracted with dichloromethane, dried (MgSO$_4$) and the solvent removed in vacuo. The residue was purified using flash chromatography to yield 4-(2-chloro-4-morpholin-4-yl-thieno[3,2-d]pyrimidin-6-ylmethyl)-piperazine-1-carboxylic acid tert-butyl ester (3.4 g). Treatment with HCl in dichloromethane/methanol yielded 4-(2-chloro-6-(piperazin-1-ylmethyl)thieno[3,2-d]pyrimidin-4-yl)morpholine 30.

Example 6

(2-chloro-4-morpholinothieno[3,2-d]pyrimidin-6-yl)-N-methylmethanamine 35

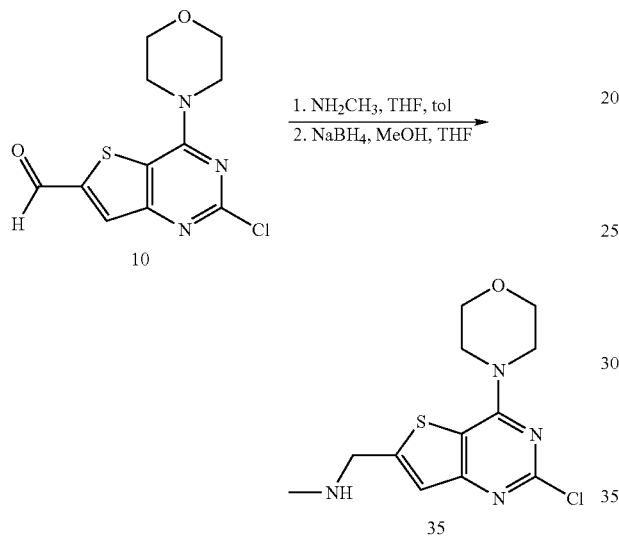

2-Chloro-4-morpholinothieno[3,2-c]pyrimidine-6-carbaldehyde 10 (2.0 g) was dissolved in 50 mL toluene and 50 mL THF followed by the addition of 20 mL of 40% methylamine in H$_2$O. The reaction mixture was stirred at room temp under N$_2$ for 24 hours. The solvents were removed in vacuo and the residue was dissolved in 50 mL methanol and 50 mL THF and the NaBH$_4$ added portion-wise. This reaction mixture was stirred at room temp under N$_2$ for 24 hours and complete reaction was confirmed by LCMS. The solvents were removed in vacuo and the crude product purified by flash chromatography (EtOAc/EtOH) to give 1.12 g 35 (53% yield). MS (Q1) 300 (M+).

Example 7

(2-chloro-7-methyl-4-morpholinothieno[3,2-d]pyrimidin-6-yl)-N-methylmethanamine 37

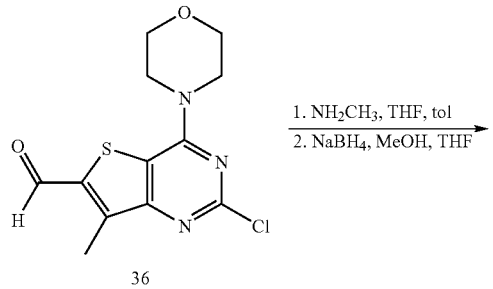

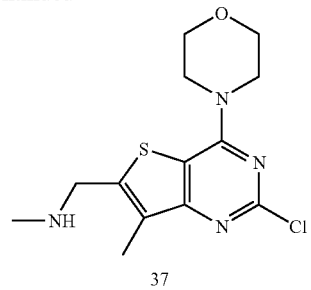

2-Chloro-7-methyl-4-morpholinothieno-[3,2-d]pyrimidine-6-carbaldehyde 36 was dissolved in 20 mL toluene and 20 mL THF followed by the addition of 15 mL 40% methylamine in H$_2$O and the reaction was stirred for 24 hours. The reaction mixture was concentrated in vacuo and the residue dissolved in 30 mL methanol and 30 mL THF followed by the addition of NaBH$_4$. The reaction was stirred at room temp for at least 24 hours and product formation was confirmed by LCMS. The solvents were removed in vacuo and the crude product purified by flash chromatography to give 2.53 g (2-chloro-7-methyl-4-morpholinothieno[3,2-d]pyrimidin-6-yl)-N-methylmethanamine 37 (70% yield) MS (Q1) 314 (M)+

Example 8

4-(2-Chloro-6-((4-(methylsulfonyl)piperazin-1-yl)methyl)thieno[3,2-d]pyrimidin-4-yl)morpholine 31

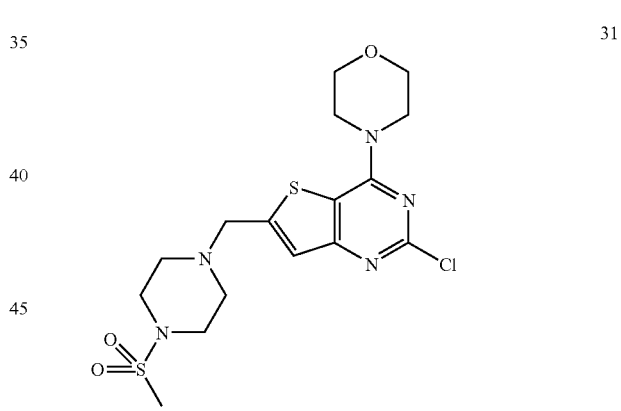

Reaction between N—BOC-piperazine and methane sulfonyl chloride in dichloromethane and triethylamine yielded 4-methanesulfonyl-piperazine-1-carboxylic acid tert-butyl ester. Cleavage of the BOC protecting group using HCl (2M) in dichloromethane yielded 1-methanesulfonyl-piperazine HCl salt.

A mixture of 2-chloro-4-morpholin-4-yl-thieno[3,2-d]pyrimidine-6-carbaldehyde 10 (1.00 g), 1-methanesulfonyl-piperazine (750 mg) and trimethylorthoformate (3.80 mL) was stirred in 1,2-dichloroethane (30 mL) for 6 hrs at room temperature. To this was added sodium triacetoxyborohydride (900 mg) and the reaction mixture was stirred for 24 hours at room temperature. The mixture was then quenched with brine, extracted with dichloromethane, dried (MgSO$_4$) and the solvent removed in vacuo. The residue was triturated with hot ethyl acetate to yield 4-(2-chloro-6-((4-(methylsulfonyl)piperazin-1-yl)methyl)thieno[3,2-d]pyrimidin-4-yl)morpholine 31 as a white solid (1.01 g).

Example 9

4-(4,4,5,5-Tetramethyl-[1,3,2]dioxaborolan-2-yl)-1H-indazole 7-route 1

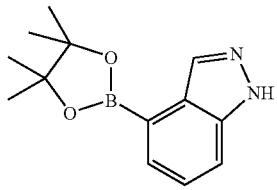

Intermediate 7 was prepared according to the methods of US 2008/0076768; US 2008/0076758; WO 2006/046031, incorporated by reference herein.

Example 10

1-(Tetrahydro-2H-pyran-2-yl)-4-(4,4,5,5-tetramethyl-1,3,2-dioxaborolan-2-yl)-1H-indazole 40

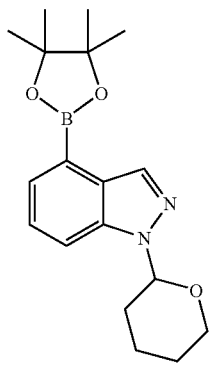

Intermediate 40 was prepared according to the methods of US 2008/0039459; US 2008/0076768; US 2008/0076758; US 2008/0207611, incorporated by reference herein.

Example 11

2-(1H-Indazol-4-yl)-4-morpholin-4-yl-thieno[3,2-d]pyrimidine-6-carbaldehyde 11

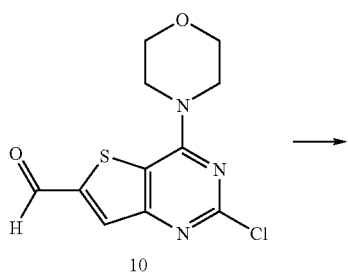

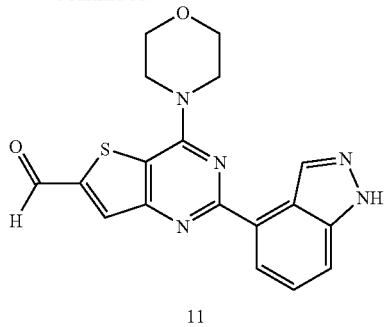

A mixture of 2-chloro-4-morpholin-4-yl-thieno[3,2-d]pyrimidine-6-carbaldehyde 10 (100 mg, 0.35 mmol), 4-(4,4,5,5-tetramethyl-[1,3,2]dioxaborolan-2-yl)-1H-indazole (70) (95 mg, 0.39 mmol) and sodium carbonate (112 mg) were suspended in toluene (2.5 mL), ethanol (1.5 mL) and water (0.7 mL). To this was added bis(triphenylphosphine)palladium(II) chloride (13.5 mg) and the reaction vessel was flushed with argon. The reaction mixture was microwaved at 120° C. for 1 h and then partitioned between DCM and water, the organic layer was washed with brine, dried over magnesium sulfate, filtered and evaporated in vacuo. The resulting residue was purified using flash chromatography to yield 2-(1H-indazol-4-yl)-4-morpholin-4-yl-thieno[3,2-d]pyrimidine-6-carbaldehyde 11 (97 mg).

Example 12

4-(2-(1H-Indazol-4-yl)-6-((4-(methylsulfonyl)piperazin-1-yl)methyl)thieno[3,2-d]pyrimidin-4-yl)morpholine (Formula Ia, GDC-0941)

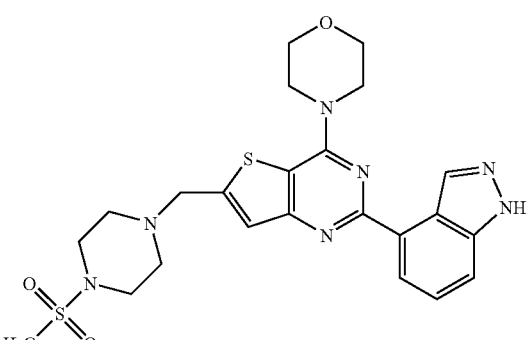

A mixture of 4-(2-chloro-6-((4-(methylsulfonyl)piperazin-1-yl)methyl)thieno[3,2-d]pyrimidin-4-yl)morpholine 31 from Example 4 (2.00 g), 4-(4,4,5,5-tetramethyl-[1,3,2]dioxaborolan-2-yl)-1H-indazole 7 (2.26 g), toluene (24 mL), ethanol (12 mL), water (6 mL), sodium carbonate (1.72 g) and PdCl$_2$(PPh$_3$)$_2$ (325 mg) was heated to 130° C. in the microwave for 90 minutes (US 2008/0076768; WO 2006/046031, incorporated by reference herein).

The reaction mixture was cooled, diluted with chloroform, washed with brine, dried (MgSO$_4$) and the solvent removed in vacuo. The residue was purified using flash chromatography (ethyl acetate then 5% ethyl acetate/methanol) and then trituration with ether yielded Formula Ia compound, GDC-0941 (1.4 g). MS data: (ESI+): MH+ 514. NMR data: (CDCl$_3$):

2.67-2.71 (4H, m), 2.81 (3H, s), 3.29-3.33 (4H, m), 3.89 (2H, s), 3.89-3.93 (4H, m), 4.08-4.12 (4H, m), 7.41 (1H, s), 7.51 (1H, t, J=7.2), 7.60 (1H, d, J=8.3), 8.28 (1H, d, J=7.5), 9.02 (1H, s), 10.10 (1H, br)

Example 13

(S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (Formula Ib)

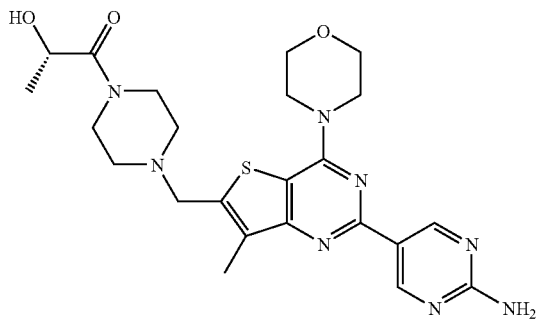

Ib

2-Chloro-7-methyl-4-morpholinothieno[3,2-d]pyrimidine-6-carbaldehyde 36 (495 mg) was reacted with Boc-piperazine via General Procedure B-3 to give tert-butyl 4-((2-chloro-7-methyl-4-morpholinothieno[3,2-d]pyrimidin-6-yl)methyl)piperazine-1-carboxylate.

Tert-butyl 4-((2-chloro-7-methyl-4-morpholinothieno[3,2-d]pyrimidin-6-yl)methyl)piperazine-1-carboxylate (777 mg) was subjected to General Procedure E to give the HCl salt of 2-chloro-7-methyl-4-morpholino-6-((piperazin-1-yl)methyl)thieno[3,2-d]pyrimidine. The HCl salt of 2-chloro-7-methyl-4-morpholino-6-((piperazin-1-yl)methyl)thieno[3,2-d]pyrimidine (590 mg) was reacted with lactic acid via General Procedure B-2 to give (S)-1-(4-((2-chloro-7-methyl-4-morpholinothieno[3,2-d]pyrimidin-6-yl)methyl)piperazin-1-yl)-2-hydroxypropan-1-one.

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 50 mg of 5-(4,4,5,5-tetramethyl-1,3,2-dioxaborolan-2-yl)pyrimidin-2-amine via General Procedure A-2 to give 10 mg of Formula Ib (US 2008/0242665, incorporated by reference). MS (Q1) 499.3 (M)$^+$.

Example 14 p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM MgCl$_2$, 0.05% Chaps, and 1 mM DTT) to 10 mM PIP$_2$ (Echelon-Inc., Salt Lake City, Utah.) final concentration. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore (λex=530 nm; λem=590 nm) in 384-well black low volume Proxiplates (PerkinElmer, Wellesley, Mass.) Fluorescence polarization values were plotted as a function of the protein concentration, and the EC$_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110alpha PI3K (final concentration) combined with PIP$_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore (λex=530 nm; λem=590 nm) in 384-well black low volume proxi plates (PerkinElmer, Wellesley, Mass.) Fluorescence polarization values were plotted as a function of the antagonist concentration, and the IC$_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The compound was serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope).

Example 15

In Vitro Cell Proliferation Assay

Efficacy of Formula I or II compounds were measured by a cell proliferation assay employing the following protocol (Mendoza et al (2002) Cancer Res. 62:5485-5488). The Cell-Titer-Glo® Luminescent Cell Viability Assay, including reagents and protocol are commercially available (Promega Corp., Madison, Wis., Technical Bulletin TB288). The assay assesses the ability of compounds to enter cells and inhibit cell proliferation. The assay principle is based on the determination of the number of viable cells present by quantitating the ATP present in a homogenous assay where addition of the Cell-Titer Glo reagent results in cell lysis and generation of a luminescent signal through the luciferase reaction. The luminescent signal is proportional to the amount of ATP present.

Procedure: Day 1—Seed Cell Plates (384-well black, clear bottom, microclear, TC plates with lid from Falcon #353962), Harvest cells, Seed cells at 1000 cells per 54 μl per well into 384 well Cell Plates for 3 days assay. Cell Culture Medium: RPMI or DMEM high glucose, 10% Fetal Bovine Serum, 2 mM L-Glutamine, P/S. Incubate 0/N at 37 C, 5% CO2.

Day 2—Add Drug to Cells, Compound Dilution, DMSO Plates (serial 1:2 for 9 points), Add 20 ul compounds at 10 mM in the 2nd column of 96 well plate. Perform serial 1:2 across the plate (10 μl+20 μl 100% DMSO) for a total of 9 points using Precision. Media Plates 96-well conical bottom polypropylene plates from Nunc (cat.#249946) (1:50 dilution) Add 147 μl of Media into all wells. Transfer 3 μl of DMSO+compound from each well in the DMSO Plate to each corresponding well on Media Plate using Rapidplate.

For 2 drug combo studies, transfer one drug 1.5 μl of DMSO+ compound from each well in the DMSO Plate to each corresponding well on Media Plate using Rapidplate. Then, transfer another 1.5 ul to the medium plate.

Drug Addition to Cells, Cell Plate (1:10 dilution), Add 6 μl of media+compound directly to cells (54 μl of media on the cells already). Incubate 3 days at 37 C, 5% CO2 in an incubator that will not be opened often.

Day 5—Develop Plates, Thaw Cell Titer Glo Buffer at room temperature. Remove Cell Plates from 37° C. and equilibrate to room temperature. for about 30 minutes. Add Cell Titer Glo Buffer to Cell Titer Glo Substrate (bottle to bottle). Add 30 μl Cell Titer Glo Reagent (Promega cat.# G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate robot (Zymark Corp., Hopkinton, Mass.). The diluted compounds were then added to quadruplicate wells in 384-well cell plates and incubated at 37 C and 5% CO2. After 4 days, relative numbers of viable cells were measured by luminescence using Cell-Titer Glo (Promega) according to the manufacturer's instructions and read on a Wallac Multilabel Reader (PerkinElmer, Foster City). EC50 values were calculated using Prism 4.0 software (GraphPad, San Diego). Drugs in combination assays were dosed starting at 4×EC50 concentrations. If cases where the EC50 of the drug was >2.5 μM, the highest concentration used was 10 μM. PI3K inhibitors and chemotherapeutic agents were added simultaneously or separated by 4 hours (one before the other) in all assays.

An additional exemplary in vitro cell proliferation assay includes the following steps:

1. An aliquot of 100 μl of cell culture containing about $10^4$ cells (see FIGS. 1A-C for cell lines and tumor type) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.
9. Analyze using the Chou and Talalay combination method and Dose-Effect Analysis with CalcuSyn software (Biosoft, Cambridge, UK) in order to obtain a Combination Index.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Alternatively, Proliferation/Viability was analyzed after 48 hr of drug treatment using Cell Titer glo reagent (Promega Inc., Madison, Wis.). DMSO treatment was used as control in all viability assays. $IC_{50}$ values were calculated using XL fit software (IDBS, Alameda, Calif.)

The AML cell lines AP-1060, EOL-1, FKH-1, GF-D8, HEL, HL-60, HNT-34, Kasumi-1, KG-1, ME-1, ML-2, MOLM-13, MOLM-16, MV4-11, NOMO-1, OCI-AML2, OCI-AML3, OCI-AML5, OCI-M1, OCI-M2, PL-21, SET-2, SIG-M5, SKM-1, THP-1, UKE-1, and UT-7 were obtained from either ATCC or DSMZ. Cells are maintained in RPMI 1640 media with 10% heat-inactivated FBS (Sigman-Aldrich) and 2 mol/L Lglutamine. Antibodies for Western blotting were purchased from Cell Signal Technology, with the exception of p110δ antibody which was obtained from Epitomics Inhibitor GDC-0941 was synthesized at Genentech. Rapamycin, Ara-C, and daunorubicin were purchased from Sigma. All compounds were prepared as stock solutions in DMSO, and diluted in assay buffer upon use. Blast cells were isolated from AML patient peripheral blood or bone marrow samples by Ficoll separation. After wash in PBS, isolated cells were cultured in RPMI 1640 media with 10% FBS and a cytokine cocktail as indicated (IGF-1, SCF, GMCSF, and IL-3 at 10 ng/ml each).

Human multiple myeloma cell lines were all obtained from the American Type Culture Collection (ATCC, Manassas, Va.) and also mentioned in earlier studies ( ). Cells were cultured in RPMI 1640 medium supplemented with 10% fetal bovine serum, 100 units/ml penicillin, 2 mM L-glutamine, and 100 mg/ml streptomycin (Life Technology, Grand Island, N.Y.) at 37° C. under 5% $CO_2$.

Example 16

In Vivo Mouse Tumor Xenograft Efficacy

Mice: Female severe combined immunodeficiency mice (Fox Chase SCID®, C.B-17/IcrHsd, Harlan) were 8 to 9 weeks old and had a BW range of 15.1 to 21.4 grams on Day 0 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-Dri® Bed-o'Cobs® Laboratory Animal Bedding in static microisolators on a 12-hour light cycle at 21-22° C. (70-72° F.) and 40-60% humidity. PRC specifically complies with the recommendations of the Guide for Care and Use of Laboratory Animals with respect to restraint, husbandry, surgical procedures, feed and fluid regulation, and veterinary care. The animal care and use program at PRC is accredited by the Association for Assessment and Accreditation of Laboratory Animal Care International (AAALAC), which assures compliance with accepted standards for the care and use of laboratory animals.

Tumor Implantation:

Xenografts were initiated with cancer cells. Cells were cultured in RPMI 1640 medium supplemented with 10% fetal bovine serum, 2 mM glutamine, 100 units/mL penicillin, 100 g/mL streptomycin sulfate and 25 g/mL gentamicin. The cells were harvested during exponential growth and resuspended in phosphate buffered saline (PBS) at a concentration of $5 \times 10^7$ cells/mL. On the day of tumor implant, each test mouse received 1×10^7 cells (0.2 mL) implanted subcutaneously in the right flank, and tumor growth was monitored as the average size approached the target range of 100 to 150 mm3. Twenty-one days after tumor implantation, designated as Day 0 of the study, the mice were placed into four groups each consisting of ten mice with individual tumor volumes ranging from 75-172 mm3 and group mean tumor volumes from 120-121 mm3 (see Appendix A). Volume was calculated using the formula:

$$\text{Tumor Volume (mm}^3\text{)}=(w^2 \times l)/2$$

where w=width and l=length in mm of a tumor. Tumor weight may be estimated with the assumption that 1 mg is equivalent to 1 mm3 of tumor volume.

Therapeutic Agents:

Formula Ia compound (GDC-0941, Genentech, Inc.) was supplied as a dry powder in salt form, which contained 73% active agent, and was stored at room temperature protected from light. Drug doses were prepared weekly in 0.5% methylcellulose: 0.2% Tween 80 in deionized water (MC/Tw80, "Vehicle") and stored at 4° C. The salt form containing 73% active agent was accounted for in the formulation of G-033829 doses. Rituximab (Rituxan® 10 mg/mL for injection, Genentech, Lot #M79901) was purchased as the clinical drug. Doses of rituximab were prepared on each day of dosing by diluting an aliquot of the stock with sterile saline (0.9% NaCl). All doses were formulated to deliver the stated mg/kg dosage in a volume of 0.2 mL per 20 grams of body weight (10 mL/kg).

Treatment:

All doses were scaled to the body weights of the individual animals and were provided by the route indicated in each of the figures.

Endpoint:

Tumors were measured twice each week using calipers. Mice were monitored individually, and each animal was euthanized when its tumor reached a volume of 1500 mm3 or at the end of the study on Day 40, whichever came first. However, due to the self-limiting growth of control tumors, the endpoint was reduced to 1000 mm3 for analysis. The time to endpoint (TTE) for each mouse was calculated from the following equation:

$$\text{TTE (days)}=[\log_{10}(\text{endpoint volume, mm}^3)-b]/m$$

where b is the intercept and m is the slope of the line obtained by linear regression of a log-transformed tumor growth data set. The data set was comprised of the first observation that exceeded the study endpoint volume and the three consecutive observations that immediately preceded the attainment of the endpoint volume. Animals that do not reach the endpoint are assigned a TTE value equal to the last day of the study. Animals classified as NTR (non-treatment-related) deaths due to accident (NTRa) or due unknown causes (NTRu) are excluded from TTE calculations (and all further analyses). Animals classified as TR (treatment-related) deaths or NTRm (non-treatment-related death due to metastasis) are assigned a TTE value equal to the day of death. Treatment outcome was evaluated by tumor growth delay (TGD), which is defined as the increase in the median time to endpoint (TTE) in a treatment group compared to the control group:

$$\text{TGD}=T-C$$

expressed in days, or as a percentage of the median TTE of the control group:

$$\% \text{ TGD}=(T-C)/C \times 100$$

where: T=median TTE for a treatment group, C=median TTE for the control group (Group 1). Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm3 for one or more of these three measurements. In a CR response, the tumor volume is less than 13.5 mm3 for three consecutive measurements during the course of the study. An animal with a CR response at the termination of a study is additionally classified as a tumor-free survivor (TFS). Animals were monitored for regression responses.

Toxicity:

Animals were weighed daily for the first five days of the study and twice weekly thereafter. The mice were observed frequently for overt signs of any adverse, treatment-related side effects, and clinical signs of toxicity were recorded when observed. Acceptable toxicity is defined as a group mean body weight (BW) loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 10 days of the last dose. A death is classified as NTR if there is no evidence that death was related to treatment side effects.

Example 17

Western Blotting for Detection of p-Akt, p-BAD and p-S6 Ribosomal Protein Post GDC-0941 Treatment of B Cell and Myeloma Cell Lines Materials: All reagents for electrophoresis and blotting buffer stocks are from Invitrogen.

B cell lines (DoHH2 and WSU-DLCL2) and Myeloma cell lines (OPM2 and U266) were maintained in RPMI-1640/10% FBS in the presence of Pen/Strep and Glutamine.

Protocol:
1. Seed $10^7$ cells of each cell line in 10 mL culture media in 10 cm Petri dish, 2 dishes for each cell line.
2. Add 5 uL of 10 mM GDC-0941 stock (in DMSO) to one dish of 10 mL culture for final 5 uM drug and add 5 uL DMSO to the other dish as control.
3. Keep cells at 37° C., 5% CO2 incubator for 4 hours before harvesting.
4. Harvest 9 mL culture (equivalent to $9 \times 10^6$ cells) to 15 mL conical tube and pellet and make cell lysates with 1×SDS sample buffer. Transfer the other 1 mL of each condition (equivalent to $1 \times 10^6$ cells) to 5 mL FACS tube (BD) for FACS.
5. Wash cells once with cold PBS.
6. Measure the OD of the protein samples and prepare the samples with NuPAGE electrophoresis system reagents to load 20 ug of each.
7. Mix each protein sample for electrophoresis with appropriate amount of NuPAGE LDS sample buffer and Reducing Agent and apply 70° C. heat for 10 min.
8. Load 10 uL of SeeBlue Plus2 Pre-stained standard and 20 ug of each sample into 4-12% NuPAGE Norvex Bis-Tris Gel and run with MES-SDS buffer in the presence of antioxidant (135 volts for 1 hour in the XCell SureLock Mini-Cell apparatus).
9. Transfer gels to the blotting membrane using iBlot apparatus.
10. Wash 1× with 1×TBST buffer.
11. Block the membrane with 20 mL 1×TBST 5% non-fat milk for 2 hours.
12. Wash 3× with 1×TBST buffer.

13. Incubate membrane in 10 mL 1×TBST 5% BSA and primary abs (p-Akt, clone 193H12, p-BAD, clone 185D10 and p-S6RP, clone D57.2.2D, beta-actin, clone 13E5, Cell Signaling) at appropriate dilution at 4C O/N. p-Akt and p-6SRP and beta-actin rabbit abs are added to the same membrane and others each on a separate membrane (multiple gels are generated early).
14. Wash 3× with 1×TBST buffer.
15. Incubate membrane with HRP-conjugated Goat anti-rabbit ab at appropriate dilution in 10 mL 1×TBST buffer/5% non-fat milk at room temperature for 2 hours.
16. Wash 3× with 1×TBST buffer.
17. Incubate membrane with 3 mL LumiGLO for 3 min, drain the excess solution and expose to x-ray film.

Alternatively, $10 \times 10^6$ cells for each condition were plated in 10 cm$^2$ plate, and cells were treated using GDC-0941, dexamethasone, or lenalidomide, and or in combinations. DMSO treatment was used as control. Cells were washed once with cold PBS and lysed using 1 X cell lysis buffer (Cell Signaling Technology, Beverly, Mass.). An equal amount of protein was resolved using Nupage Bis-Tris gels (Invitrogen, Carlsbad, Calif.). Western blot analysis was performed using anti-phospho-Akt (Serine 473), anti-PTEN, anti-phospho-BAD (serine136), anti-phospho-FoXO 1/3a, Bim, cleaved caspase 9, cleaved caspase 3, p27, and cleaved PARP antibodies (Cell Signaling Technology, Beverly, Mass.). Total AKT, total BAD, total Foxo3a and β-actin (Sigma) levels were used as loading controls.

Example 18

FACS Protocol for Intracellular Detection of p-Akt and p-S6 Ribosomal Protein Post GDC-0941 Treatment B cell lines (DoHH2 and WSU-DLCL2) and Myeloma cell lines (OPM2 and U266) were maintained in RPMI-1640/10% FBS in the presence of Pen/Strep and Glutamine.

Protocol:
1. Seed $10^7$ cells of each cell line in 10 mL culture media in 10 cm Petri dish, 2 dishes for each cell line.
2. Add 5 uL of 10 mM GDC-0941 stock (in DMSO) to 10 mL culture for final 5 uM drug and add 5 uL DMSO to the other dish as control.
3. Keep cells at 37° C., 5% CO$_2$ incubator for 4 hours before harvesting.
4. Transfer 1 mL of each condition (equivalent to $10^6$ cells) to 5 mL FACS tube (BD) and spin at 1200 rpm for 5 min prior to fixation (harvest the other 9 mL culture-9×10$^6$ cells to 15 mL conical tube for Western).
5. Aspirate the supernatant and fix the cells at room temperature with Fix/Perm Medium A (CAT# GAS001S-100) for 15 min.
6. Wash the cells with PBS/2% FBS 1×
7. Aspirate the supernatant and permeablize the cells at room temperature with Fix/Perm Medium B (CAT# GAS002S-100) for 15 min.
8. Wash the cells with PBS/2% FBS 1×
9. Resuspend cells with 300 uL PBS/2% BSA and divide cells into 3 tubes 100 uL each (one for isotype-Rabbit IgG Alexa Fluor-647 and one for p-Akt Alexa Fluor-647 clone 193H12 and one for p-S6RP Alexa Fluor-647 clone D57.2.2E, all rabbit abs are from Cell Signaling).
10. Add 50 ng of each Ab to corresponding tube and incubate at room temperature for 30 min.
11. Wash the cells with PBS/2% FBS 1×
12. Resuspend cells with 300 uL PBS/2% BSA and acquire data on FACSCalibur (BD) using CellQuest program.
13. Analyze data using FlowJo program and display data in histograms.

Example 19

FACS Protocol for Measuring Quantitative Fluorescence of Apoptotic and Viable Cells Post GDC-0941 Treatment Apoptotic and viable cells were measured by quantitative fluorescence analysis using fluorescence-activated cell sorting (FACS) assay with minor modifications (Munugalavadla et al (2008) Mol. Cell. Biol. 28(23):7182-7198). Various multiple myeloma cell lines (1×10$^6$) were treated with DMSO or various concentrations of Figure Ia GDC-0941 for 24 hr, cells were then stained using Annexin-V-APC/PI kit (BD Biosciences, San Jose, Calif.) according to the manufacturers instructions and analyzed by flow cytometry. In case of primary multiple myeloma patient sample, 2 million nucleated BM cells were seeded in a 6 well plate in 2 ml advanced-RPMI (Invitrogen, Carlsbad, Calif.) supplemented with 2% heat inactivated bovine growth serum (Hyclone, Waltham, Mass.) and 2 ng/ml recombinant IL6 (R&D Systems Inc., Minneapolis, Minn.). Cells were treated with vehicle (DMSO), 1 μM or 10 μM GDC-0941 for 72 hrs and then analyzed by flow cytometry to evaluate drug-induced apoptosis. The following reagents were used: CD45RA-FITC, CD38-APC and Propidium Iodide (all from BD Pharmingen, San Jose, Calif.). Data was acquired on a CyanADP instrument, (Dako Cytomation) and analyzed using FlowJo software (Tree Star). Live plasma cells were identified as CD38hiCD45RA- and PI-.

Example 20

Cell Cycle Analysis

Cell cycle analysis was done using Click-iT™ Edu Cytometry Assay Kit (Invitrogen, Carlsbad, Calif.) according to manufactures instructions. Fluorescence was measured on BD LSR-II and data was analyzed using FlowJo software (Becton Dickinson).

Example 21 pAKT Measurement in Primary MM Bone Marrow Mononuclear Cells using Meso Scale Discovery (MSD) Assay Bone marrow mononuclear cells (BM-MNC) from MM donors were cultured overnight in 10 ml RPMI supplemented with 10% FBS. After incubation, the cells were washed once with growth media and resuspended in 1 ml of media. For each donor, the cells were split into 500 mL aliquots and were treated with either DMSO or GDC-0941 at 1 mM for 1 hour at 37° C. After treatment, the cell pellets were collected at 1200 rpm for five minutes and pellets were washed once with cold PBS. The cell pellets were re-suspended with 60 ml 1× Mesoscale Discovery (MSD, Gaithersburg, Md.) lysis buffer and lysates were cleared by centrifugation at 4° C. at 14000 rpm for 10 minutes. The cleared cell lysates were used to evaluate phospho-Akt (Ser473) and total Akt using MSD kit according to manufactures instructions with minor modifications.

We claim:
1. A method for the treatment of a hematopoietic malignancy comprising administering a therapeutic combination as a combined formulation or by alternation to a mammal in need thereof, wherein the therapeutic combination comprises a synergistically effective amount of a compound having Formula I or pharmaceutically acceptable salt thereof, and a synergistically effective amount of one or more chemotherapeutic agents selected from dexamethasone, doxorubicin, rituximab, prednisone, lenalidomide, bortezomib, and rapamycin;

wherein the Formula I compound is 4-(2-(1H-indazol-4-yl)-6-((4-(methylsulfonyl)piperazin-1-yl)methyl)thieno[3,2-d]pyrimidin-4-yl)morpholine having Formula Ia:

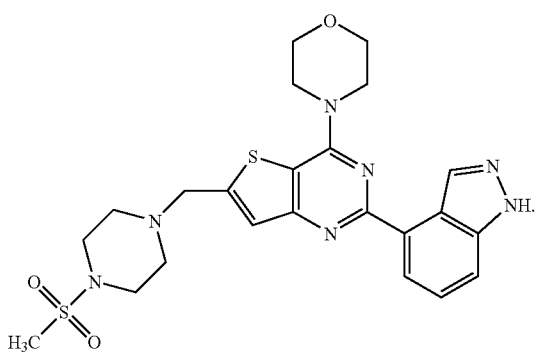

2. The method of claim 1 wherein the chemotherapeutic agent is dexamethasone.
3. The method of claim 1 wherein the chemotherapeutic agent is doxorubicin.
4. The method of claim 1 wherein the chemotherapeutic agent is rituximab.
5. The method of claim 1 wherein the chemotherapeutic agent is prednisone.
6. The method of claim 1 wherein the chemotherapeutic agent is lenalidomide.
7. The method of claim 1 wherein the chemotherapeutic agent is bortezomib.
8. The method of claim 1 wherein the chemotherapeutic agent is rapamycin.
9. The method of claim 1 wherein the therapeutic combination further comprises cyclophosphamide and vincristine.
10. The method of claim 1 wherein the pharmaceutically acceptable salt of the Formula I compound is selected from a salt formed with hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.
11. The method of claim 1 wherein the synergistically effective amount of a compound having Formula I, and the synergistically effective amount of the chemotherapeutic agent are administered as a combined formulation.
12. The method of claim 1 wherein the synergistically effective amount of a compound having Formula I, and the synergistically effective amount of the chemotherapeutic agent are administered to a mammal by alternation.
13. The method of claim 12 wherein the mammal is administered with the chemotherapeutic agent and subsequently administered with the Formula I compound.
14. The method of claim 12 wherein the therapeutic combination is administered by a dosing regimen where the synergistically effective amount of a compound having Formula I is administered in a range from twice daily to once every three weeks, and the synergistically effective amount of the chemotherapeutic agent is administered in a range from twice daily to once every three weeks.
15. The method of claim 14 wherein the dosing regimen is repeated one or more times.
16. The method of claim 1 wherein administration of the therapeutic combination results in a synergistic effect.
17. The method of claim 1 wherein the hematopoietic malignancy is selected from non-Hodgkin's lymphoma, diffuse large hematopoietic lymphoma, follicular lymphoma, mantle cell lymphoma, chronic lymphocytic leukemia, multiple myeloma, AML, and MCL.
18. The method of claim 1 wherein the Formula I compound and the chemotherapeutic agent are each administered in an amount from about 1 mg to about 1000 mg per unit dosage form.
19. The method of claim 1 wherein the Formula I compound and the chemotherapeutic agent are administered in a ratio of about 1:50 to about 50:1 by weight.

* * * * *